(12) United States Patent
Mayo et al.

(10) Patent No.: US 8,207,228 B2
(45) Date of Patent: Jun. 26, 2012

(54) CALIXARENE-BASED PEPTIDE CONFORMATION MIMETICS, METHODS OF USE, AND METHODS OF MAKING

(75) Inventors: Kevin H. Mayo, Minneapolis, MN (US); Thomas R. Hoye, St. Paul, MN (US); Xuemei Cheri, Voorheesville, NY (US)

(73) Assignee: Regents of the University of Minnesota, St. Paul, MN (US)

( * ) Notice: Subject to any disclaimer, the term of this patent is extended or adjusted under 35 U.S.C. 154(b) by 1042 days.

(21) Appl. No.: 11/664,641

(22) PCT Filed: Oct. 4, 2005

(86) PCT No.: PCT/US2005/036128
§ 371 (c)(1),
(2), (4) Date: Dec. 17, 2007

(87) PCT Pub. No.: WO2006/042104
PCT Pub. Date: Apr. 20, 2006

(65) Prior Publication Data
US 2008/0300164 A1 Dec. 4, 2008

Related U.S. Application Data

(60) Provisional application No. 60/616,133, filed on Oct. 4, 2004.

(51) Int. Cl.
*A61K 31/195* (2006.01)
*A61K 31/015* (2006.01)

(52) U.S. Cl. ........ 514/569; 514/617; 514/616; 514/618; 514/709; 514/577; 562/88

(58) Field of Classification Search .................. 514/569, 514/577, 618, 709, 616, 617; 562/88
See application file for complete search history.

(56) References Cited

U.S. PATENT DOCUMENTS

| 5,409,959 | A | 4/1995 | Hwang et al. |
|---|---|---|---|
| 5,441,983 | A | 8/1995 | Hwang et al. |
| 5,489,612 | A | 2/1996 | Atwood et al. |
| 5,786,324 | A | 7/1998 | Gray et al. |
| 5,830,860 | A | 11/1998 | Gray et al. |
| 5,955,577 | A | 9/1999 | Mayo |
| 6,319,367 | B1 | 11/2001 | Coates et al. |
| 6,486,125 | B1 | 11/2002 | Mayo et al. |
| 7,030,087 | B2 | 4/2006 | Gray et al. |
| 7,056,514 | B2 | 6/2006 | Mayo et al. |

(Continued)

FOREIGN PATENT DOCUMENTS

WO   WO 95/19974 A2   7/1995

(Continued)

OTHER PUBLICATIONS

Jain et al. (Nature Medicine, vol. 3 (11), 1997, pp. 1203-1208).*

(Continued)

*Primary Examiner* — Savitha Rao
(74) *Attorney, Agent, or Firm* — Mueting Raasch & Gebhardt, P.A.

(57) ABSTRACT

A class of topomimetic calixarene-based peptide mimetics is described. Calixarene-based peptide mimetics have various biological activities such as, for example, bactericidal activity, antiangiogenic activity, and/or antitumor activity. Methods of use and methods of designing calixarene-based peptide mimetics are described.

34 Claims, 9 Drawing Sheets

U.S. PATENT DOCUMENTS

| | | |
|---|---|---|
| 7,144,982 B2 | 12/2006 | Mayo |
| 2002/0146406 A1 | 10/2002 | Mayo |
| 2004/0053828 A1 | 3/2004 | Mayo et al. |
| 2005/0118678 A1 | 6/2005 | Mayo |
| 2005/0266575 A1 | 12/2005 | Mayo et al. |
| 2006/0128629 A1 | 6/2006 | Mayo et al. |
| 2006/0183191 A1 | 8/2006 | Gray et al. |
| 2007/0010438 A1 | 1/2007 | Mayo et al. |

FOREIGN PATENT DOCUMENTS

| | | |
|---|---|---|
| WO | WO 99/00394 A1 | 1/1999 |
| WO | WO 01/70930 A2 | 9/2001 |
| WO | WO 2005/072779 A2 | 8/2005 |
| WO | WO 2005/123660 A2 | 12/2005 |
| WO | WO 2006/010138 A1 | 1/2006 |

OTHER PUBLICATIONS

Tarboletti et al. (European Journal of Cancer, 40, 2004 pp. 884-889).*

Castermans et al., "Angiostatic compounds stimulate tumor immunity," Meeting Abstract #5701. *American Association for Cancer Research Annual Meeting; Tumor Biology 39: Tumor Angiogenesis and Antiangiogenic Therapeutics.* Washington, D. C.: Apr. 1-5, 2006. Published in the *Proc. Amer. Assoc. Cancer Res.* 47(2006):1341. Available online [retrieved on Aug. 4, 2009]. Retrieved from the Internet: <http://www.aacrmeetingabstracts.org/cgi/content/abstract/2006/1/1341-a?maxto show=&HITS=10&hits=10 &RESULTFORMAT=1&author1=Castermans &andorexacttitle=and&andorexacttitleabs=and&searchid=1 &FIRSTINDEX=0&sortspec=relevance&fdate=1/1/2004 &tdate=12/31/ 2008&resourcetype=HWCIT>; 2 pgs.

Dings and Mayo, "A journey in structure-based drug design discovery: from designed peptides to protein surface topomimetics as antibiotic and antiangiogenic agents," Oct. 2007 *Acc. Chem. Res.* 40(10):1057-1065. Available online on Jul. 28, 2007.

Dings et al., "Ovarian tumor growth regression using a combination of vascular targeting agents anginex or topomimetic 0118 and the chemotherapeutic irofulven," Jul. 8, 2008 *Cancer Lett.* 265(2):270-280. Available online on Apr. 1, 2008.

Dings et al., "Enhanced in vivo antitumor activity for the combination of irofulven and the antiangiogenic compounds, anginex or KM0118," Meeting Abstract #4986. *American Association for Cancer Research Annual Meeting; Experimental and Molecular Therapeutics 41: Combination Chemotherapy and Chemosensitization.* Washington, D. C.: Apr. 1-5, 2006. Published in the *Proc. Amer. Assoc. Cancer Res.* 46(2005):1177-1178. Available online [retrieved on Aug. 4, 2009]. Retrieved from the Internet: <http://www. aacrmeetingabstracts.org/cgi/content/abstract/2005/1/1177-c?maxto show=&HITS=10&hits=10&RESULTFORMAT= &author1=Dings&andorexactfulltext=and&searchid=1 &FIRSTINDEX=0&sortspec=relevance&resourcetype=HWCIT>; 2 pgs.

Griffoen et al., "A topomimetic of anginex: a potent anti-angiogenic and anti-tumor agent," Poster Abstract p.702. *3rd International Symposium in Targeted Anticancer Therapies.* Amsterdam, Netherlands: Mar. 3-5, 2005. Published in May 2005 *Annals of Oncology* 16 (Supplement 3):iii45.

Griffoen, "Anti-angiogenesis agents; the interface between the immune system and the tumor," Slides presented at *ESMO International Symposium Immunology*; European Society for Medical Oncology. Athens, Greece: Nov. 15-17, 2007. Available online [retrieved on Aug. 4, 2009]. Retrieved from the Internet: <http://www.esmo.org/education/abstracts-and-virtual-meetings/eis-on-immunol ogy-2007.html>; 43 pgs.

Abad et al., "The X-ray crystallographic structure of the angiogenesis inhibitor angiostatin." *J. Mol. Biol.*, 318; 1009-17 (2002).

Agerberth et al., "Amino acid sequence of PR-39. Isolation from Pig intestine of a new member of the finally proline-arginine-rich antibacterial peptides." *Eur. J. Biochem.* 1991, 202, 849-854.

Andreu et al., "N-terminal analogues of cecropin A: synthesis, antibacterial activity, and conformational properties." *Biochemistry* 1985, 24, 1683-1688.

Andreu et al., "Animal antimicrobial peptides: an overview." *Biopolymers*, 47; 415-33 (1998).

Arnaud-Neu, et al., "Synthesis, x-ray crystal structures, and cation-binding properties of alkyl calixaryl esters and ketones, a new family of macrocyclic molecular receptors." *J. Am. Chem. Soc.* 111, 8681-8691 (1989).

Barbieri, Joseph T. "Vaccines and Therapies for Botulism," Grant Abstract, Grant No. 1U54AI057153-010002 [online]. National Institute of Allergy and Infectious Diseases, project dates Sep. 4, 2003 to Feb. 29, 2008 [retrieved on Sep. 27, 2007]. Retrieved from the Internet: <http://crisp.cit.nih.gov/crisp/CRISP_LIB. getdoc?textkey=6802935&p_grant_num=1U54AI057153-010002 &p_query=&ticket=46353958&p_audit_session_id=266626278 &p_keywords=>; 2 pgs.

Barendsz-Janson et al., "In vitro angiogenesis assays: plasminogen lysine binding site 1 inhibits in vitro tumor-induced angiogenesis." *J.Vasc.Res.* 35, 109-114 (1998).

Battafarano et al., "Peptide derivatives of three distinct lipopolysaccharide-induced tumor necrosis factor-alpha secretion in vitro," *Surgery*, 118, 318-324 (1995).

Beven et al., "The antibiotic activity of cationic linear ampihpathic peptides: lessons from the action of luecine/lysine copolymers on bacteria of the class *Mollicutes*." *Eur. J. Biochem.* 2003, 270, 2207-2217.

Blaskovich et al., "Design of GFB-111, a platelet-derived growth factor binding molecule with antiangiogenic and anticancer activity against human tumors in mice." *Nat. Biotechnol*, 18; 1065-1070 (2000).

Blondelle et al., "Synthetic combinatorial libraries: novel discovery strategy for identification of antimicrobial agents." *Antimicrob. Agents Chemother*. 1996, 40, 1067-1071.

Boehm et al., "Antiangiogenic therapy of experimental cancer does not induce acquired drug resistance." *Nature*, 390; 404-7 (1997).

Bohach et al., "Analysis of toxic shock syndrome isolates producing staphylococcal enterotoxins B and C1 with use of southern hybridization and immunologic assays." *Rev. Infect. Diseases 11*, S75-82 (1989).

Bryant, Jr. et al, *Angew. Chem. Int. Ed*. 39, 1641-1643 (2000).

Budson et al., "The angiogenesis inhibitor AGM-1470 selectively increases E-selectin." *Biochem. Biophys. Res. Comm.*, 225, 141-145 (1996).

Casnati et al., "Synthesis, antimicrobial activity and binding properties of calix[4]arene based vancomycin mimics," *Bio. & Med. Chem. Letters*, 1996;6(22):2699-2704.

Chen et al., Abstract No. 371, 229th National Meeting of Am. Chem. Soc., San Diego, CA, Mar. 13-17, 2005.

Cody et al. "Protective anti-lipopolysaccharide monoclonal antibodies inhibit tumor necrosis factor production." *J. Surg. Res.*, 52:314-319 (1992).

Cohen, "Epidemiology of Drug Resistance: Implications for a post-antimicrobial era," *Science* 1992, 257, 1050-55.

Dathe et al., "Structural features of helical antimicrobial peptides: their potential to modulate activity on model membranes and biological cells." *Biochim. Biophys. Acta* 1999, 1462, 71-87.

Dings et al., "Anti-tumor activity of the novel angiogenesis inhibitor anginex." *Cancer Lett* 194, 55-66 (2003).

Dings et al., "The designed angiostatic peptide anginex synergistically improves chemotherapy and antiangiogenesis therapy with angiostatin." *Cancer Res.*, 63, 382-385 (2003).

Dings et al., "Discovery and development of anti-angiogenic peptides: A structural link." *Angiogenesis*, 6; 83-91 (2003).

Dings et al. "Design of non-peptidic topomimetics of antiangiogenic proteins with antitumor activities." Jul. 5, 2006 *J Natl Cancer Inst.* 98(13):932-936.

Dunn et al. "Efficacy of type-specific and cross-reactive murine monoclonal antibodies directed against endotoxin during experimental sepsis." *Surgery*, 98:283, 1985.

Eguchi & Kahn, "Design, synthesis, and application of peptide secondary structure mimetics." *Mini Rev. Med. Chem.* 2, 447-462 (2002).

Eguchi et al., "Chemogenomics with peptide secondary structure mimetics." *Comb. Chem. High Throughput Screen.* 6, 611-621 (2003).

Eisenfuhr et al., "A ribozyme with michaelase activity: synthesis of the substrate precursors." *Bioorg. Med. Chem.* 2003, 11, 235-249.

Elsbach et al., "Bactericidal/permeability increasing protein and host defense against gram-negative bacteria and endotoxin." *J. Curr. Opinion in Immuno.* 1993, 5, 103-107.

Ferguson et al., "Siderophore-mediated iron transport: crystal structure of FhuA with bound lipopolysaccharide." *Science*, 282; 2215-20 (1998).

Folkman "What is the evidence that tumors are angiogenesis dependent?" *J. Natl. Cancer. Inst.*, 82, 4-6 (1990).

Folkman et al., "Angiogenesis." *J Biol. Chem.*, 267, 10931-10934 (1992).

Ganz, "Antimicrobial proteins and peptides in host defense." *Semin. Respir. Infect.* 2001, 16, 4-10.

Giangaspero et al., "Amphipathic alpha helical antimicrobial peptides." *Eur. J. Biochem.* 2001, 268, 5589-5600.

Glenn & Fairlie, "Mimetics of the peptide beta-strand." *Mini Rev. Med. Chem.* 2, 433-445 (2002).

Golebiowski et al., "High-throughput organic synthesis of peptide mimetics." *Curr. Opin. Drug Discov.Devel.* 4, 428-434 (2001).

Gray et al., "B/PI-derived synthetic peptides: synergistic effects in tethered bactericidal and endotoxin neutralizing peptides." *Biochim. Biophys. Acta* 1995, 1244, 185-190.

Griffioen et al., "Endothelial intercellular adhesion molecule-1 expression is suppressed in human malignancies: the role of angiogenic factors." *Cancer Res.*, 56, 1111-1117 (1996).

Griffioen et al., "Tumor angiogenesis is accompanied by a decreased inflammatory response of tumor-associated endothelium." *Blood*, 88, 667-673 (1996).

Griffioen et al., "Angiogenesis: potentials for pharmacologic intervention in the treatment of cancer, cardiovascular diseases, and chronic inflammation." *Pharmacol. Rev.*, 52; 237-68 (2000).

Griffioen et al., "Anginex, a designed peptide that inhibits angiogenesis." *Biochem. J.*, 354, 233-242 (2001).

Groenewegen et al., "Supernatants of human leukocytes contain mediator, different from interferon gamma, which induces expression of MHC class II antigens," *J. Exp. Med.* 164, 131-143 (1986).

Gutsche et al., "Calixarenes. 6. Synthesis of a functionalizable calix[4]arene in a conformationally rigid cone conformation," *J. Am. Chem. Soc.* 104, 2652-2653 (1982).

Gutsche et al., "Calixarenes 9: Conformational isomers of the ethers and esters of calix[4]arenes," *Tetrahedron* 1983, 39, 409-426.

Hancock et al., "Cationic bactericidal peptides." in *Advances in Microbial Physiology* Edited by Poole. Academic Press; Harcourt Brace & Company, Publishers: San Diego, CA. 1995 vol. 37, 135-175.

Hancock, "Peptide antibiotics." *Lancet* 1997, 349, 418-422.

Hill et al., "Crystal structure of defensin HNP-3, an amphiphilic dimer: mechanisms of membrane permeabilization." *Science* 1991, 251, 1481-1485.

Hohenester et al., "Crystal structure of the angiogenesis inhibitor endostatin at 1.5 A resolution," *EMBO J.*, 17; 1656-1664 (1998).

Hoess et al., "Crystal structure of an endotoxin-neutralizing protein from the horseshoe crab, Limulus anti-LPS factor, at 1.5 A resolution," *EMBO J.* 1993, 12,3351-3356.

Homma et al., "A New Antigenic Schema and Live-cell Slide-agglutination Procedure for the Infrasubspecific, Serologic Classification of *Pseudomonas aeruginosa*," *Japan. J. Exp. Med.* 46, 329-336 (1976).

Japelj et al., "Structural origin of endotoxin neutralization and antimicrobial activity of a lactoferrin-based peptide." *J. Biol. Chem.*, 280; 16955-16961 (2005).

Johnson, J.R. et al., "Defining inoculation conditions for the mouse model of ascending urinary tract infection that avoid immediate vesicoureteral reflux yet produce renal and bladder infection." *J. Infect. Disease 173*, 746-749 (1996).

Johnson, J.R. et al., "A novel multiply primed polymerase chain reaction assay for identification of variant papG genes encoding the Gal)alpha 1-4)Gal-binding PapG adhesins of *Escherichia coli*." *J. Infect. Disease 173*, 920-926 (1996).

Kawano et al., "Antimicrobial peptide, tachyplesin I, isolated from hemocytes of the horseshoe crab (*Tachypleus tridentatus*). NMR determination of the beta-sheet structure." *J. Bio. Chem.* 1990, 265, 15365-15367.

Kee & Jois, "Design of beta-turn based therapeutic agents." *Curr. Pharm. Des.* 9, 1209-1224 (2003).

Kitayama et al., "Suppressive effect of basic fibroblast growth factor on transendothelial emigration of CD4(+) T-lymphocyte." *Cancer. Res.*, 54 4729-4733 (1994).

Lamartine et al., "Antimicrobial activity of calixarenes," *C.R. Chimie*, 2002;5(3):163-169.

Laskowski et al., "PDBsum more: new summaries and analyses of the known 3D structure of proteins and nucleic acids." *Nucleic Acids Research 33*, D266-268 (2005).

Lehrer et al., "Defensins: endogenous antibiotic peptides of animal cells." *Cell* 1991, 64, 229-230.

Liekens et al., "Angiogenesis: regulators and clinical applications." *Biochem. Pharm.*, 61, 253-270 (2001).

Little et al., "Functional domains fo recombinant bactericidal/permeability increasing protein (rBPI23)." *J. Biol. Chem.* 1994, 269, 1865-1872.

Liu et al., "Synthesis of Calix[4]arene derivatives with alkyl guanidinium or chiral bicyclic guanidinium," *Synthesis*, 2001, 4, 607.

Lockwood et al., "The future for antibiotics: Bacterial membrane disintegrators," *Drugs of the Future* 2003, 28, 911-923.

Matsuzaki et al., "Membrane permeabilization mechanisms of a cyclic antimicrobial peptide, tachyplesin I, and its linear analog." *Biochemistry* 1997, 36, 9799-9806.

Mayo et al., "A recipe for designing water-soluble, beta-sheet-forming peptides," *Protein Sci.*, 5; 13001-1315 (1996).

Mayo et al., "Designed beta-sheet-forming peptide 33mers with potent human bactericidal/permeability increasing protein-like bactericidal and endotoxin neutralizing activities." *Biochem. Biophys. Acta*, 1425; 81-92 (1998).

Mayo et al., "Structure-function relationships in novel peptide dodecamers with braod-spectrum bactericidal and endotoxin-neutralizing activities." *Biochem. J.* 2000, 349, 717-728.

Mayo et al., "Designed beta-sheet peptides that inhibit proliferation and induce apoptosis in endothelial cells." *Angiogenesis*, 4, 45-51 (2001).

Mayo et al., "Design of a partial peptide mimetic of anginex with antiangiogenic and anticancer activity." *Journal of Biological Chemistry* 278, 45746-52 (2003).

Mayo, Kevin H. "Peptide Based Antiangiogenic Antitumor Agent," Grant Abstract, Grant No. 1R01CA09609-01 [online]. National Cancer Institute, project dates Apr. 1, 2002 to Mar. 28, 2006 [retrieved on Sep. 27, 2007]. Retrieved from the Internet: <http://crisp.cit.nih.gov/crisp/CR1SP_LIB.getdoc?textkey=6460869&p_grant_num=1R01CA096090-01&p_query=&ticket=46353569&p_audit_session_id=2666 26278&p_keywords=>; 2 pgs.

Mayo, Kevin H. "Peptide Based Antiangiogenic Antitumor Agent," Grant Abstract, Grant No. 5R01CA09609-02 [online]. National Cancer Institute, project dates Apr. 1, 2002 to Mar. 28, 2006 [retrieved on Sep. 27, 2007]. Retrieved from the Internet: <http://crisp.cit.nih.gov/crisp/CRISP_LIB.getdoc?textkey=6619648&p_grant_num=5R01CA096090-02&p_query=&ticket=46353569&p_audit_session_id=266626278&p_keywords=>; 2 pgs.

Mayo, Kevin H. "Peptide Based Antiangiogenic Antitumor Agent," Grant Abstract, Grant No. 5R01CA09609-03 [online]. National Cancer Institute, project dates Apr. 1, 2002 to Mar. 28, 2006 [retrieved on Sep. 27, 2007]. Retrieved from the Internet: <http://crisp.cit.nih.gov/crisp/CRISP_LIB.getdoc?textkey=6710598&p_grant_num=5R01CA096090-03&p_query=&ticket=46353569&p_audit_session_id=266626278&p_keywords=>; 2 pgs.

Mayo, Kevin H. "Peptide Based Antiangiogenic Antitumor Agent," Grant Abstract, Grant No. 5R01CA09609-04 [online]. National Cancer Institute, project dates Apr. 1, 2002 to Mar. 31, 2006 [retrieved on Sep. 27, 2007]. Retrieved from the Internet: <http://crisp.cit.nih.gov/erisp/CRISP_LIB.getdoc?textkey=6873740&p_grant_num=5R0ICA096090-04&p_query=&ticket=46353569&p_audit_session_id=266626278&p_keywords=>; 2 pgs.

Mayo, Kevin H. "Dibenzofuran-based Anginex Mimetics that Target Galectin-1," Grant Abstract, Grant No. 2R01CA09609-05A2

[online]. National Cancer Institute, project dates Apr. 1, 2002 to May 12, 2012 [retrieved on Sep. 27, 2007]. Retrieved from the Internet: <http://crisp.cit.nih.gov/crisp/CRISP_LIB. getdoc?textkey=7322753&p_grant_num=2R01CA096090-05A2 &p_query=&ticket=46353569&p_audit session_id=26 6626278 &p_keywords=>; 2 pgs.

Melder et al., "During angiogenesis, vascular endothelial growth factor and basic fibroblast growth factor regulate natural killer cell adhesion to tumor endothelium." *Nature Med.*, 2, 992-997 (1996).

Moore et al. "Squalamine: an aminosterol antibiotic from the shark," *Proc Natl. Acad. Sci. USA* 1993, 90, 1354-1358.

Otvos, Jr., "Antibacterial peptides isolated from insects." *J. Pept. Sci.* 2000, 6, 497-511.

Piali et al., "Endothelial vascular cell adhesion molecule 1 expression is suppressed by melanoma and carcinoma." *J. Exp. Med.*, 181, 811-816 (1995).

Pristovsek et al., "Solution structure of polymyxins B and E and effect of binding to lipopolysaccharide: an NMR and molecular modeling study." *J. Med. Chem.*, 42; 4604-13 (1999).

Ramakrishnan, Sundaram "Role of Angiogenesis in the Etiology and Prevention of Ovarian Cancer. Project 1: Effect of Angiogenesis Inhibitors in Preventing Ovarian Cancer Growth," Grant Abstract, Grant No. DAMD 17-99-1-9564 [online]. U.S. Army Medical Research and Material Command, project report date Oct. 2002 [retrieved on Oct. 9, 2007]. Retrieved from the Internet: <http://stinet. dtic.mil/stinet/jsp/docread. jsp?K2DocKey=http%3A%2F%2Fstinet. dtic. mil%2Fstinet%2FXSLTServlet%3Fad%3DADA413335%40trA-search&Format=1F&Custom=&querytext=9564 &AD=ADA413335 &TI=Role+of+Angiogenesis+in+the+Etiology+ and+Prevention+of+Ovarian+Cancer.+Project+1%3A+Effect+of+ Angiogenesis+Inhibitors+in+Preventing+Ovarian+Cancer+Growth &RD =Oct.+01%2C+2002 &DC=%26nbsp%3B+%26nbsp%3B+%26nbsp%3B+% 26nbsp%3B+%26nbsp%3B+01+-+APPROVED+FOR+PUBLIC+ RELEASE&XPC=&PAG=259+Pages%28s%29&MC=&PE=>; 2 pgs.

Ramakrishnan, Sundaram "Role of Angiogenesis in the Etiology and Prevention of Ovarian Cancer. 2: Angiogenesis Factors in the Malignant Transformation of Ovarian Surface Epithelium," Grant Abstract, Grant No. DAMD 17-99-1-9564 [online]. U.S. Army Medical Research and Material Command, project report date Oct. 2003 [retrieved on Oct. 9, 2007]. Retrieved from the Internet: <http://stinet. dtic.mil/stinet/jsp/docread. jsp?K2DocKey=http%3A%2F%2Fstinet. dtic. mil%2Fstinet%2FXSLTServlet%3Fad%3DADA421997%40trA-search&Format=1F&Custom=&querytext=9564 &AD=ADA421997 &TI=Role+of+Angiogenesis+in+the+Etiology+and+Prevention+ of+Ovarian+Cancer.+2. +Angiogenesis+Factors+in+the+Malignant+Transformation+of+ Ovarian+Surface+Epithelium& RD=October+01%2C+2003 &DC=%26nbsp%3B+%26nbsp%3B+%26nbsp%3B+%26nbsp% 3B+%26nbsp%3B+01+-+APPROVED+FOR+PUBLIC+RELEAS E&XPC=&PAG=7+Pages%28s%29&MC=&PE=>; 2 pgs.

Ramakrishnan, Sundaram "Role of Angiogenesis in the Etiology and Prevention of Ovarian Cancer. 3: Rational Antiangiogenic Peptide Design-Effect on Ovarian Cancer Growth," Grant Abstract, Grant No. DAMD 17-99-1-9564 [online]. U.S. Army Medical Research and Material Command, project report date Oct. 2003 [retrieved on Oct. 9, 2007]. Retrieved from the Internet: <http://stinet.dtic.mil/ stinet/jsp/docread.jsp?K2DocKey=http%3A%2F%2Fstinet. dtic. mil%2Fstinet%2FXSLTServlet%3Fad%3DADA421996%40trA-search&Format=1F&Custom=&querytext=9564 &AD=ADA421996 &TI=Role+of+Angiogenesis+in+the+Etiology+and+Prevention+ of+Ovarian+Cancer.+3. +Rational+Antiangiogenic+Peptide+Design- Effect+on+Ovarian+Cancer+Growth&RD=October+01%2C+2003 &DC=%26nbsp%3B+%26nbsp%3B+%26nbsp%3B+%26nbsp%3 B+%26nbsp%3B+01+-+APPROVED+FOR+PUBLIC+RELEASE &XPC=&PAG=49+Pages%28s%29&MC=&PE=>; 2 pgs.

Ramakrishnan, Sundaram "Role of Angiogenesis in the Etiology and Prevention of Ovarian Cancer. 4: Prevention of Ovarian Carcinoma Dissemination by Inhibiting Cell Adhesion," Grant Abstract, Grant No. DAMD 17-99-1-9564 [online]. U.S. Army Medical Research and Material Command, project report date Oct. 2003 [retrieved on Oct. 9, 2007]. Retrieved from the Internet: <http://stinet.dtic.mil/ stinet/jsp/docread.jsp?K2DocKey=http%3A%2F%2Fstinet. dtic. mil%2Fstinet%2FXSLTServlet%3Fad%3DADA421995%40trA-search&Format=1F&Custom=&querytext=9564 &AD=ADA421995 &TI=Role+of+Angiogenesis+in+the+Etiology+and+Prevention+ of+Ovarian+Cancer.+4.+Prevention+of+Ovarian +Carcinoma+Dissemination+by+Inhibiting+Cell+Adhesion &Rd=October+01%2C+2003 &DC=%26nbsp%3B+%26nbsp%3B+%26nbsp%3B+%26nbsp %3B+%26nbsp%3B+01+-+APPROVED+FOR+PUBLIC+ RELEASE&XPC=&PAG=125+Pages%28s%29&MC=&PE=>; 2 pgs.

Ramakrishnan, Sundaram "Role of Angiogenesis in the Etiology and Prevention of Ovarian Cancer. 1: Effect of Angiogenesis Inhibitors in Preventing Ovarian Cancer Growth," Grant Abstract, Grant No. DAMD 17-99-1-9564 [online]. U.S. Army Medical Research and Material Command, project report date Oct. 2003 [retrieved on Oct. 9, 2007]. Retrieved from the Internet: http://stinet.dtic.mil/stinet/jsp/ docread.jsp?K2DocKey=http%3A%2F%2Fstinet.dtic. mil%2Fstinet%2FXSLTServlet%3Fad%3DADA421998%40trA-search&Format=1F&Custom=&querytext=9564 &Ad=ADA421998&TI=Role+of+Angiogen esis+in+the+Etiology+and+Prevention+of+Ovarian+Cancer.+1. +Effect+of+Angi ogenesis+Inhibitors+in+Preventing+%26nbsp%3B+%26nbsp% 3B+%26nbsp%3B+%26nbsp%3B+%26nbsp%3B+01+-+APPRO-VED+FOR+PUBLIC+RELEASE&XPC=&PAG=1 07+Pages%28s%29&MC=&PE=>; 2 pgs.

Ramakrishnan, Sundaram "Role of Angiogenesis in the Etiology and Prevention of Ovarian Cancer," Grant Abstract, Grant No. DAMD 17-99-1-9564 [online]. U.S. Army Medical Research and Material Command, project report date Oct. 2004 [retrieved on Oct. 9, 2007]. Retrieved from the Internet: <http://stinet.dtic.mil/stinet/jsp/ docread.jsp?K2DocKey=http%3A%2F%2Fstinet. dtic. mil%2Fstinet%2FXSLTServlet%3Fad%3DADA435700%40trOt her-search &Format=1F&Custom=&querytext=9564 &AD=ADA435700&TI=Role+of+Angiogenesis+in+the+ Etiology+and+Prevention+of+Ovarian+Cancer&RD=Oct. +01%2C+2004 &DC=%26nbsp%3B+%26nbsp%3B+%26nbsp%3B+%26nbsp% 3B+%26nbsp%3B+01+-+APPROVED+FOR+PUBLIC+ RELEASE+%26nbsp% 3B+%26nbsp%3B+%26nbsp%3B+%26nbsp% 3B+%26nbsp%3B+26+-+NOT+A VAILABLE+IN+MICROFICHE&XPC= &PAG=383+Pages%28s%29&MC=&PE=>; 2 pgs.

Rietschel et al., "Bacterial endotoxin: Chemical constitution, biological recognition, host response, and immunological detoxification." *Curr Top Microbiol Immunol* 216, 39-81 (1996).

Rifkind, "Prevention by polymyxin B of endotoxin lethality in mice." *J. Bacteriol.*, 93; 1463-4 (1967).

Saberwal et al., "A synthetic peptide corresponding to the hydrophobic amino terminal region of paradaxin can perturb model membranes of phosphatidyl choline and serine." *Biochim. Biophys. Acta* 1989, 984, 360-364.

Schlievert et al., "Production of *Staphylococcal pyrogenic* exotoxin type C: influence of physical and chemical factors." *J. Infect. Diseases* 147, 236-242 (1983).

Selinsky et al., "The aminosterol antibiotic squalamine permeabilizes large unilamellar phospholipid vesicles." *Biochim. Biophys. Acta* 1998, 1370, 218-234.

Selinsky et al., "Squalamine is not a proton ionophore." *Biochim. Biophys. Acta* 2000, 1464, 135-141.

Selsted et al., "Determination of the disulfide array in the human defensin HNP-2. A covalently cyclized peptide." *J. Biol. Chem.* 1989, 264, 4003-4007.

Selsted et al., "Indolicidin, a novel bactericidal tridecapeptide amide from neutrophils." *J. Biol. Chem.* 1992, 267, 4292-4295.

Simmaco et al., "Antimicrobial peptides from amphibian skin: what do they tell us?" *Biopolymers* 1998, 47, 435-450.

Sitaram et al., "Structural and charge requirements for antimicrobial and hemolytic activity in the peptide PKLLETFLSKWIG, corresponding to the hydrophobic region of the antimicrobial protein bovine seminalplasmin." *Int. J. Pept. Protein Res.* 1995, 46, 166-173.

Sun et al., "Blocking angiogenesis and tumorigenesis with GFA-116, a synthetic molecule that inhibits binding of vascular endothelial growth factor to its receptor," *Cancer Research* May 15, 2004 64:3586-3592.

Toniolo et al., "Effect of N(alpha)-Acyl chain length on the membrane-modifying properties of synthetic analogs of the lipopeptaibol trichogin GA IV," *J. Am. Chem. Soc.* 1996, 118, 4952-4958.

Tossi et al., "Design of synthetic antimicrobial peptides based on sequence analogy and amphipathicity." *Eur. J. Biochem.* 1997, 250, 549-558.

Tossi, Department of Biochemistry, Biophysics, and Macromolecular Chemistry, University of Trieste, Trieste, Italy "Antimicrobial Sequences Database" last updated Mar. 10, 2003. Available online [retrieved Oct. 4, 2007]. Retrieved from the Internet: <http://www.bbcm.units.it/~tossi/pag1.htm>; 1 pg.

Tsubery et al., "N-terminal modification of polymyxin B nonapeptides and their effect on antibacterial activity." *Peptides* 2001, 22, 1675-1681.

Van der Schaft et al., "The designer anti-angiogenic peptide anginex targets tumor endothelial cells and inhibits tumor growth in animal models." *Faseb J.*, 16, 1991-2013 (2002).

Van Vliet et al., "Lithium amides: Intra-aggregate complexation of lithium and entropy control of basicity." *Angew. Chem. Int. Ed.* 2000, 39, 1643-1645.

Virk et al., "Clinical aspects of antimicrobial resistance." *Mayo Clinic Proc.* 2000, 75, 200-214.

Wade et al., Haartman Institute and the National Library of Health Sciences, Helsinki University, Helsinki, Finland. SAPD—Synthetic Antibiotic Peptide Database. 2003. Available online [retrieved Oct. 4, 2007]. Retrieved from the Internet: <http://oma.terkko.helsinki.fi:8080/~SAPD/>; 1 pg.

Warren et al., "Endotoxin neutralization with rabbit antisera to *Escherichia coli* J5 and other gram-negative bacteria." *Infect. Immunity 55*, 1668-1673 (1987).

Weiss et al., "Purification and characterization of a potent bactericidal and membrane active protein from the granules of human polymorphonuclear leukocytes." *J. Biol. Chem.* 1978, 253, 2664-2672.

Whitmore et al., School of Crystallography, Birkbeck College, University of London, London, U.K. "Peptaibol Database," Available online [retrieved Oct. 4, 2007]. Retrieved from the Internet: <http://www.cryst.bbk.ac.uk/peptaibol/home.shtml>; 1 pg.

Wright, Jr. et al., "Thromboxane synthetase inhibitors and antihypertensive agents. 1. N-[(1H-imidazol-1-yl)alkyl]aryl amines and N-[(1H-1,2,4-triazol-1- yl)alkyl]aryl amides." *J. Med. Chem.* 1986, 29, 523-530.

Wu et al., "Efficience and fidelity in a click-chemistry route to triazol dendrimers by the copper(i)-catalyzed ligation of azides and alkynes." *Angew. Chem. Int. Ed.* 43, 3928-3932 (2004).

Zasloff et al., "Antimicrobial activity of synthetic magainin peptides and several analogues." *Proc. Natl. Acad. Sci. USA* 1988, 85, 910-913.

Wang et al., "Cytotoxicity of Poly(Phenolic)Sulfonates and their Sodium Salts in L1210 Lymphoid Leukemia Cells," *Metal-Based Drugs*, Freund Publishing House, Tel Aviv, IL 1998;5(3):147-160.

Liu et al. "Molecular Recognition of Nucleotides by a calix[4]arene derivative with two alkyl guanidinium groups at the air-water interface", 2002. New Journal of Chemistry. 26(5):601-606.

Roy et al. "Amphiphilic p-tert-Butylcalix[4]arene Scaffolds Containing Exposed Carbohydrate Dendrons". 1999. Angewandte Chemie International Edition. 38(3):369-372.

Extended European Search Report. Dated Dec. 14, 2011. Application No. 11173181.6-1211/2404895. 7 pgs. Total.

* cited by examiner

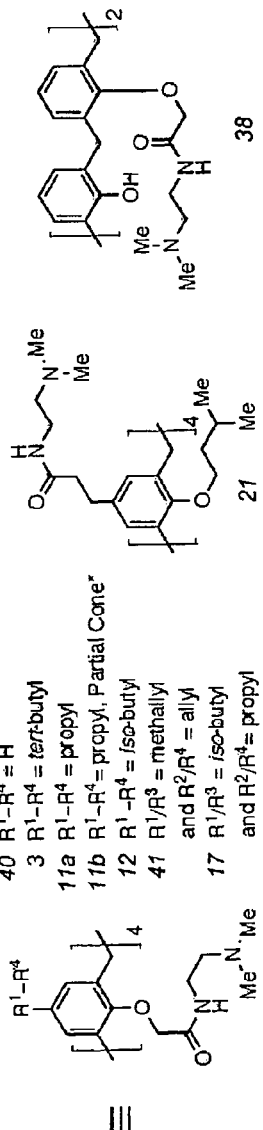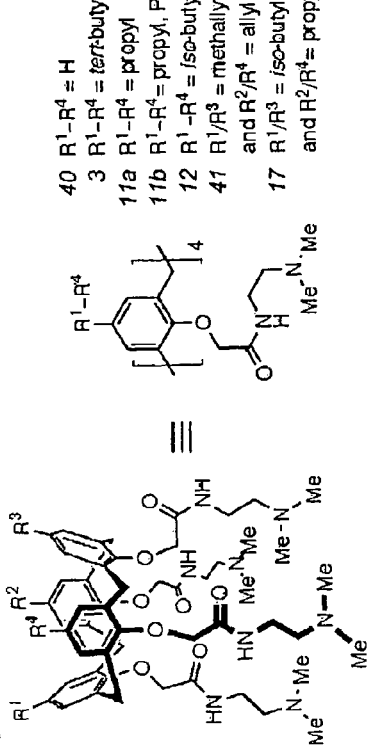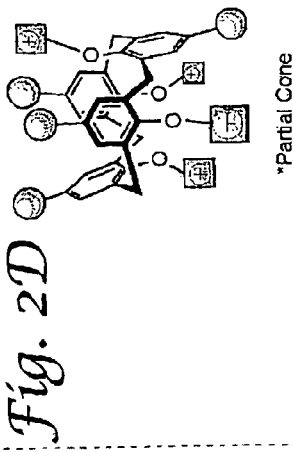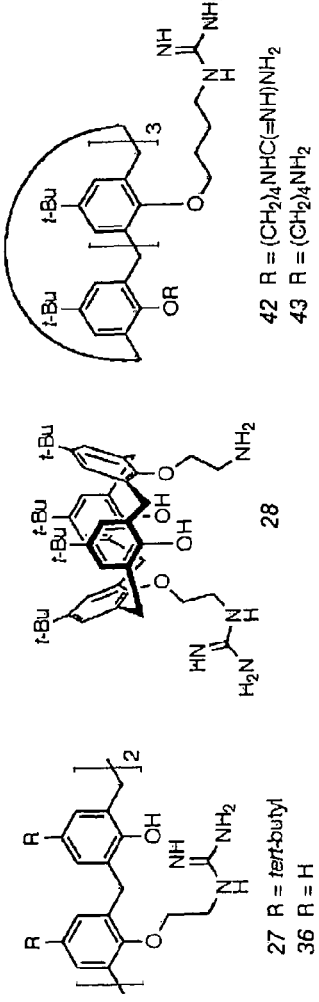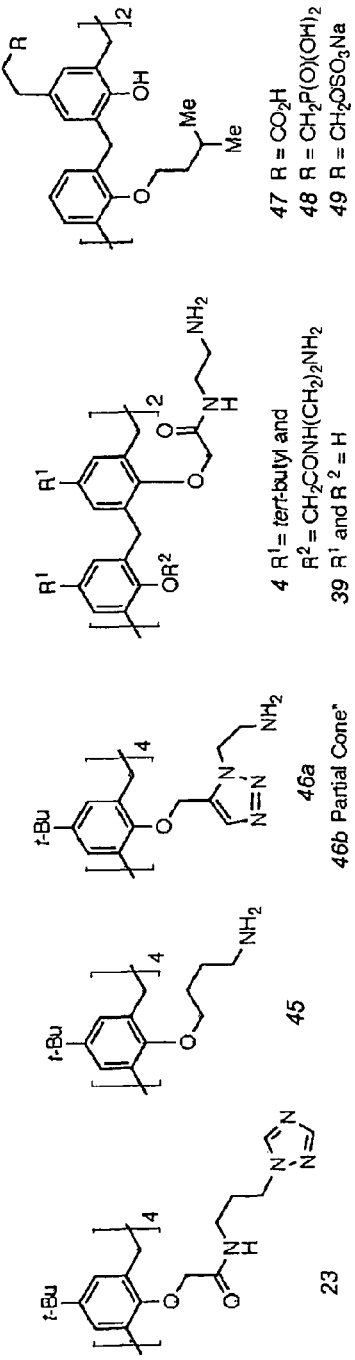
Fig. 2A  Fig. 2B  Fig. 2C  Fig. 2D

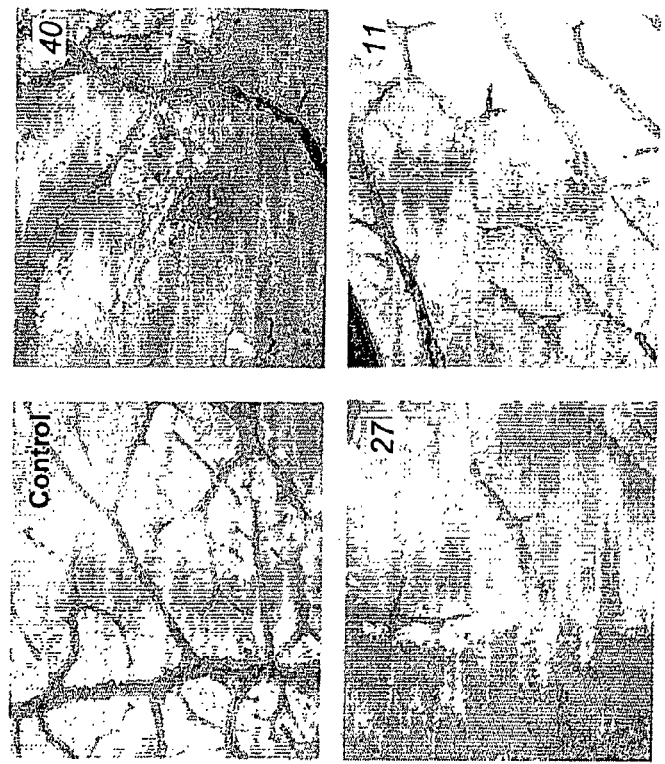
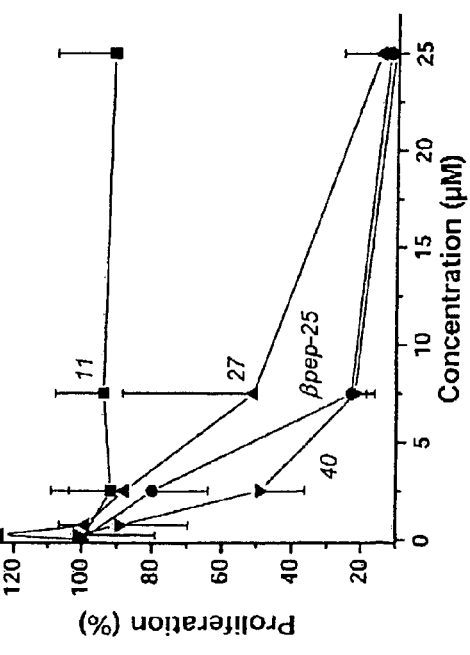
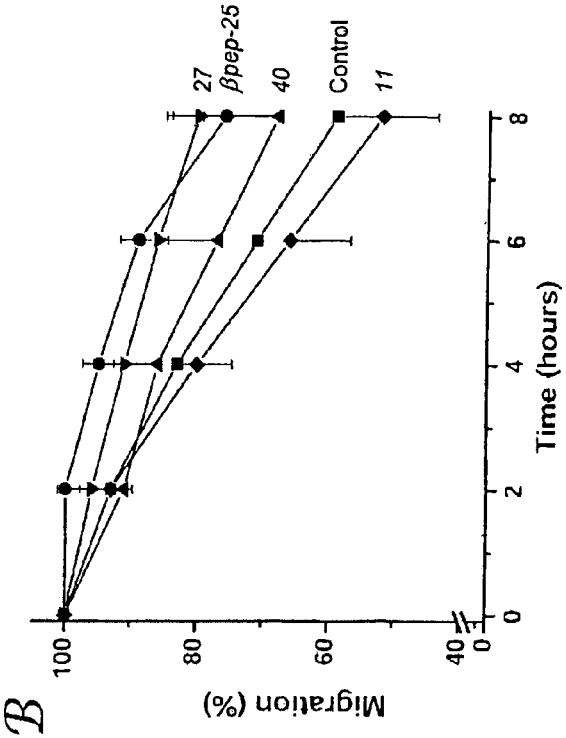
Fig. 6A
Fig. 6B
Fig. 6C

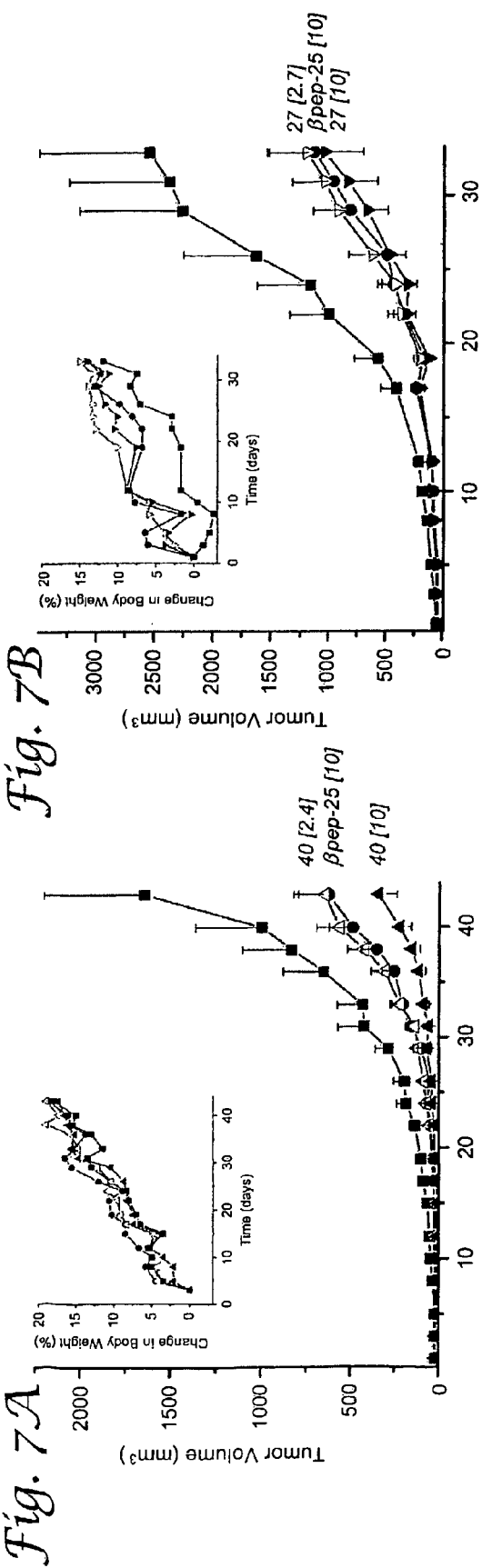
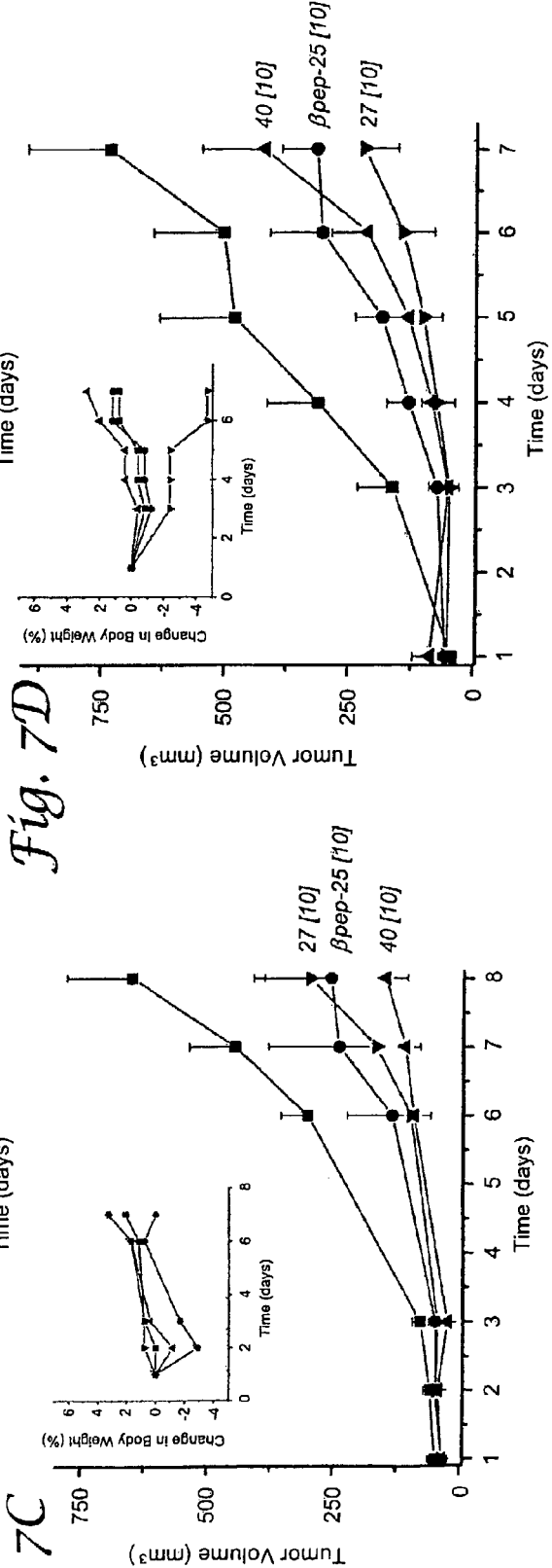
Fig. 7A  Fig. 7B  Fig. 7C  Fig. 7D

CALIXARENE-BASED PEPTIDE CONFORMATION MIMETICS, METHODS OF USE, AND METHODS OF MAKING

CONTINUING APPLICATION DATA

This application is the §371 U.S. National Stage of International Application No. PCT/US2005/036128, filed Oct. 4, 2005, which claims the benefit of U.S. Provisional Application Ser. No. 60/616,133, filed Oct. 4, 2004, both of which are incorporated by reference herein.

GOVERNMENT FUNDING

The present invention was made with government support under Grant No. R01 CA-96090, awarded by the National Cancer Institute, and Grant No. U54 AI057153, awarded by the National Institute of Allergy and Infectious Diseases. The Government may have certain rights in this invention.

BACKGROUND

Bacterial membrane-disintegrating peptides, which have their origin in naturally occurring cationic peptides, offer promising alternatives as antibiotics of the future. These novel agents generally demonstrate a broad spectrum of antibacterial activity and act by disrupting the integrity of the entire bacterial cell membrane, thereby reducing the risk of drug resistance (M. L. Cohen, Science 257, 1050-55 (1992); and A. M. D. Virk et al., Mayo Clinic Proc. 75, 200-214 (2000). Antibacterial peptides have two major distinguishing features: a net positive charge, typically of +2 to +6, and an overall amphipathic fold imparting polar and hydrophobic faces to the molecule (A. Giangaspero et al., Eur. J. Biochem. 268, 5589-5600 (2001). The cationic nature of antibacterial peptides apparently promotes selective interaction with the negatively charged surface of bacterial membranes relative to the more neutral surface of eukaryotic membranes (K. Matsuzaki et al., Biochemistry 36, 9799-9806 (1997). Once attracted to the surface, the peptide, with its amphipathic topology, triggers bacterial cell lysis (D. Andreu et al., Biochemistry 24, 1683-1688 (1985).

Sepsis and septic shock are systemic complications normally associated with increased levels of lipopolysaccharide (LPS) endotoxin in the blood stream. Many bactericidal peptides are known in vitro to bind to and to neutralize LPS (e.g., cecropins, magainins, proline-arginine-rich peptides, sapecin, tachyplesin, and defensins) (Andreu et al., Biopolymers, 47; 415-33 (1998)) as well as, more recently, βpep peptides, (Mayo et al., Protein Sci., 5; 13001-1315 (1996); Mayo et al., Biochem. Biophys. Acta, 1425; 81-92 (1998)). SC4 (Mayo et al., Biochem. J., 349(3); 717-28 (2000)), and lactoferrin-based peptide LF11 (Japelj et al., J. Biol. Chem., 280; 16955-61 (2005)). Perhaps the most prototypic is polymyxin B (PmxB), a small cyclic lipopeptide (Rifkind, J. Bacteriol., 93; 1463-4 (1967)). However, due to its high neuro- and nephrotoxicity, PmxB is limited to topical application, and most other bactericidal agents are not very effective against LPS in vivo.

Some naturally occurring bactericidal proteins also possess endotoxin-neutralizing properties. Several non-peptidic membrane disruptors have also been identified (Lockwood et al., Drugs of the Future 28, 911-923 (2003). Most prominent of these is squalamine, which is amphipathic not by the nature of its folded structure, but by the presence of charged appendages (including the polycationic triamine) on a steroid core (Moore et al. Proc Natl. Acad. Sci. USA 90, 1354-1358 (1993). The bactericidal mechanism of squalamine, despite its small size, is similar to that of membrane-disintegrating peptides (Selinsky et al., Biochim. Biophys. Acta 1370, 218-234 (1998); Selinsky et al., Biochim. Biophys. Acta 1464, 135-141 (2000).

A structural survey of these peptides reveals that regardless of their folded conformation, two trails stand out that are important for binding LPS: amphipathic character and a net positive charge (Lockwood et al., Drugs of the Future, 28; 911-923 (2003)). Presumably, positively charged residues from the peptide promote interaction with negatively charged groups on LPS, i.e., phosphates on the lipid A glucosamines and/or those in the inner core polysaccharide unit, while hydrophobic residues from the peptide interact with acyl chains on lipid A. Structural studies of peptides in complex with LPS support this notion and have provided additional insight into the molecular origins of peptide-mediated LPS neutralization (Japelj et al., J. Biol. Chem., 280; 16955-61 (2005); Ferguson et al., Science, 282; 2215-20 (1998); Pristovsek et al., J. Med. Chem., 42; 4604-13 (1999)).

Interestingly, the motif of a positively charged, amphipathic structure (primarily anti-parallel β-sheet) is also found in a number of proteins and peptides that function as antiangiogenic agents (Dings et al., Angiogenesis, 6; 83-91 (2003)). For example, angiostatin folds into an anti-parallel β-sheet structure with a highly electropositive lysine-rich binding site (Abad, J. Mol. Biol., 318; 1009-17 (2002)). Endostatin has a predominantly anti-parallel β-sheet structure (Hohenester et al., EMBO J., 17; 1656-1664 (1998)) and is highly positively charged, particularly due to the presence of multiple arginine residues. Angiogenesis, the process of new blood vessel formation, is key to normal organ development, as well as to various pathological disorders like cancer, arthritis, endometriosis, diabetic retinopathy, and restenosis (Griffioen et al., Pharmacol. Rev., 52; 237-68 (2000)). The use of agents that can inhibit angiogenesis, particularly in anti-tumor research, has indicated that anti-angiogenic therapy is a promising therapeutic modality (Boehm et al., Nature, 390; 404-7 (1997).

In the last decade or so, researchers have begun to develop modified or totally synthetic peptides (Sitaram et al., Int. J. Pept. Protein Res. 46, 166-173 (1995); Saberwal et al., Biochim. Biophys. Acta 984, 360-364 (1989); Tossi et al., Eur. J. Biochem. 250, 549-558 (1997); Blondelle et al., Antimicrob. Agents Chemother. 40, 1067-1071 (1996); Dathe et al., Biochim. Biophys. Acta 1462, 71-87 (1999); and Beven et al., Eur. J. Biochem. 270, 2207-2217 (2003)). Some resultant amphipathic peptides show promising broad bactericidal activity and specificity for bacterial rather than eukaryotic cells (R. E. Hancock, Lancet 349, 418-422 (1997); Hancock et al., Adv. Microb. Physiol. 37, 135-175 (1995). Little has been done to design non-peptidic topomimetic compounds that mimic a portion of the surface of a protein or peptide. Additional topomimetic compounds are still needed.

SUMMARY

The present invention is directed to a class of topomimetic compounds that provide a variety of biological activities. These topomimetic compounds include peptide mimetics that use an organic scaffold and particular groups to model the surface characteristics of existing bioactive molecules. Use of an organic scaffold enables preparation of compounds that have a variety of biological activities and potentially superior pharmacokinetic properties. This class of compounds includes calixarene-based peptide mimetics. A library of calixarene-based peptide mimetics have been prepared and are shown herein to possess biological activity (e.g., bactericidal activity; antiangiogenic activity; and/or antitumor activity).

One aspect of the present invention rests in the ability to capture more fully the folded conformations of small segments of protein topography (e.g., helix and beta-sheet), exemplified in two peptides (βpep-25 and SC4) with somewhat different biological activities, using calixarene in a scaffold-based approach method. Advantageously, a calixarene-based library of analogous compounds can be employed to search for activities in other systems whereby the biological activity can be mimicked.

Accordingly, in one aspect, the present invention provides methods of use for calixarene-based peptide mimetics of Formula I or II:

tacting cells with an amount of a composition effective to inhibit endothelial cell proliferation. In another embodiment, a method for inhibiting angiogenic-factor mediated inter-cellular adhesion molecule expression down-regulation is provided that includes contacting cells with an amount of a composition effective to inhibit angiogenic-factor mediated inter-cellular adhesion molecule expression down-regulation. In a further embodiment, a method for promoting angiogenic-factor mediated inter-cellular adhesion molecule expression is provided that includes contacting cells with an amount of a composition effective to promote angiogenic-factor mediated inter-cellular adhesion molecule expression. In yet another embodiment, a method for inhibiting angiogenesis is provided that includes contacting cells with an

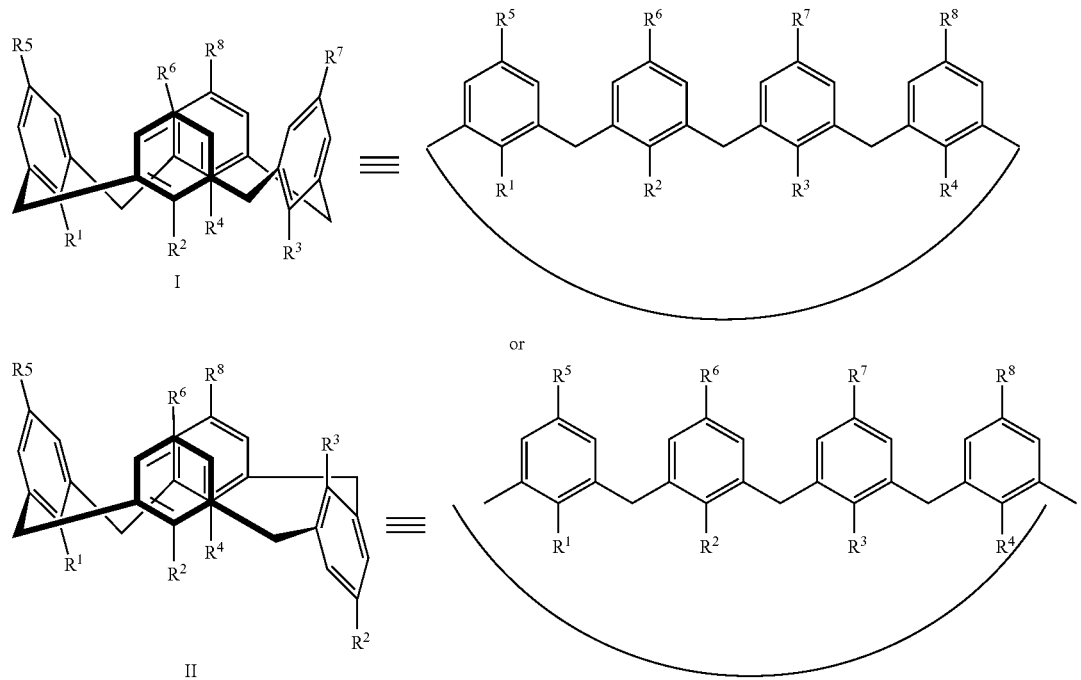

wherein, each $R^1$ through $R^8$ group is independently hydrogen or an organic group, wherein $R^1$ through $R^4$ are each independently hydrogen or an organic group of like polarity and $R^5$ through $R^8$ are each independently hydrogen or an organic group of like polarity that is of opposite polarity than those of $R^1$ through $R^4$.

In various embodiments, the calixarene-based peptide mimetics may be used to treat a variety of diseases and disorders. In one embodiment, the calixarene-based peptide mimetics may be used in a method for inhibiting bacterial infection and/or endotoxemia, the method including contacting cells with an amount of a composition effective to inhibit the bacterial infection and/or to neutralize endotoxin. In a further embodiment, the calixarene-based peptide mimetic neutralizes endotoxin, is bactericidal, or is both bactericidal and neutralizes endotoxin. In another embodiment, a method for decreasing the amount of TNF-α is provided that includes contacting cells with an amount of a composition including a calixarene-based peptide mimetic effective to decrease the amount of TNF-α. Such compositions include one or more calixarene-based peptide mimetics.

In a further embodiment, the invention provides a method for inhibiting endothelial cell proliferation that includes conamount of a composition effective to inhibit angiogenesis. Such compositions include one or more calixarene-based peptide mimetics.

In an additional embodiment, the invention provides a method for inhibiting tumorigenesis in a patient that includes administering to the patient a therapeutically effective amount of a composition that includes a calixarene-based peptide mimetic. An addition embodiment provides a method for increasing the infiltration of leukocytes into tumor tissue in a patient by administering to a patient an amount of a composition that includes a calixarene-based peptide mimetic, wherein the composition is effective to increase the amount of leukocytes (i.e. white blood cells) that can infiltrate into the tumor tissue.

In another embodiment, the invention provides a method for inhibiting atherosclerosis in a patient that includes administering to the patient a therapeutically effective amount of a composition that includes a calixarene-based peptide mimetic. In yet another embodiment, the invention provides a method for inhibiting restenosis in a patient that includes administering to the patient a therapeutically effective amount of a composition that includes a calixarene-based peptide mimetic.

A further embodiment of the invention provides a method for inhibiting diabetic retinopathy in a patient that includes administering to the patient a therapeutically effective amount of a composition that includes a calixarene-based peptide mimetic. In additional embodiments, a therapeutically effective amount of a composition that includes a calixarene-based peptide mimetic is used for a method of inhibiting neovascular glaucoma in a patient, a method for inhibiting rheumatoid arthritis in a patient, and/or a method for inhibiting endometriosis in a patient.

In the various embodiments described, a variety of calixarene-based peptide mimetics may be used.

For instance, in any of the methods described, the calixarene-based peptide mimetic may include groups $R^1$ through $R^8$ are each independently hydrogen, alkyl, cycloalkyl, aryl, aralkyl, alkoxy, thioalkoxy, cycloalkylalkoxy, heterocycloalkyl, aralkyloxy, or heteroaryl, optionally including ester, amide, amine, hydroxyl, halogen, sulfonate, phosphonate, guanidine, and/or heteroaryl groups. In further embodiments, groups $R^1$ through $R^4$ are each independently hydrogen, halogen, alkyl, cycloalkyl, aryl, aralkyl, alkoxy, thioalkoxy, cycloalkylalkoxy, heterocycloalkyl, aralkyloxy, or heteroaryl, and $R^5$ through $R^8$ are each independently any of these groups incorporating ester, amide, amine, hydroxyl, halogen, sulfonate, phosphonate, guanidine, and/or heteroaryl groups. In an alternate embodiment, groups $R^5$ through $R^8$ are each independently hydrogen, halogen, alkyl, cycloalkyl, aryl, aralkyl, alkoxy, thioalkoxy, cycloalkylalkoxy, heterocycloalkyl, aralkyloxy, or heteroaryl, amide $R^1$ through $R^4$ are each independently any of these groups incorporating ester, amide, amine, hydroxyl, halogen, sulfonate, phosphonate, guanidine, and/or heteroaryl groups In further embodiments of any of the methods described, the calixarene-based peptide mimetic may include groups $R^1$ through $R^8$ that are each independently hydrogen, alkyl, cycloalkyl, aralkyl, alkoxy, cycloalkylalkoxy, or aralkyloxy optionally including ester, amide, amine, hydroxyl, sulfonate, phosphonate, guanidine and/or heteroaryl groups. In further embodiments, groups $R^1$ through $R^4$ may be each independently alkyl, cycloalkyl, aralkyl, alkoxy, cycloalkylalkoxy, or aralkyloxy, and $R^5$ through $R^8$ may be each independently any of these groups incorporating ester, amide, amine, hydroxyl, sulfonate, phosphonate, guanidine and/or heteroaryl groups. In an alternate embodiment, $R^5$ through $R^8$ may be each independently alkyl, cycloalkyl, aralkyl, alkoxy, cycloalkylalkoxy, or aralkyloxy, and $R^1$ through $R^4$ may be each independently any of these groups incorporating ester, amide, amine, hydroxyl, sulfonate, phosphonate, guanidine and/or heteroaryl groups.

In further embodiments of the methods described, the calixarene-based peptide mimetic may be provided as a pharmaceutically acceptable salt. In an additional embodiment, the ionic form of the calixarene-based peptide mimetic salt is positively charged.

In further embodiments of the methods described that include contact a cell, the contacting step may occur in vitro. In alternate embodiments, the contacting step occurs in vivo. In additional embodiments, the contacted cells are present in a cell culture, a tissue, an organ, or an organism. In some embodiments, the cells are mammalian cells, while in further embodiments the cells are human cells.

In another aspect, the present invention provides a method of making a peptide mimetic that includes identifying a folded structured peptide of interest; determining a biologically active region of the peptide; determining the key functional groups within the biologically active region responsible for the biological activity of that region of the peptide; identifying all organic scaffold for presenting the key functional groups or analogs thereof in a spatial orientation equivalent to that in the biologically active region; and synthesizing a compound comprising the scaffold and key functional groups or analogs thereof to form a peptide mimetic of the peptide of interest.

In one embodiment of the method of making a peptide mimetic, the peptide of interest is βpep-25. In another embodiment, the organic scaffold is calixarene and the peptide mimetic is a calixarene-based peptide mimetic. In a further embodiment, the calixarene-based peptide mimetic has a structure according to Formula I or II:

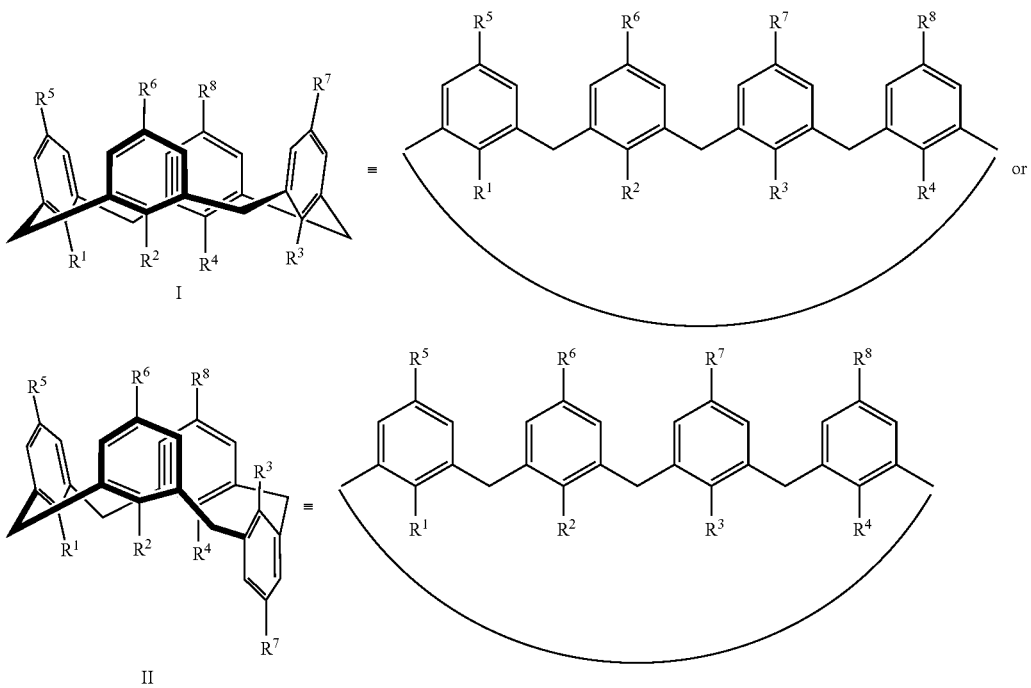

wherein each $R^1$ through $R^8$ group is independently hydrogen or an organic group, wherein $R^1$ through $R^4$ are each independently hydrogen or an organic group of like polarity and $R^5$ through $R^8$ are each independently hydrogen or an organic group of like polarity that is of opposite polarity than those of $R^1$ through $R^4$.

In an additional embodiment, the calixarene-based peptide mimetic has the structure described, and groups $R^1$ through $R^8$ are each independently hydrogen, halogen, alkyl, cycloalkyl, aryl, aralkyl, alkoxy, thioalkoxy, cycloalkylalkoxy, heterocycloalkyl, aralkyloxy, or heteroaryl, optionally including ester, amide, amine, hydroxyl, sulfonate, phosphonate, guanidine, heteroaryl, heteroarylalkyl, and/or thioalkoxy groups. In further embodiments, groups $R^1$ through $R^4$ are each independently hydrogen, halogen, alkyl, cycloalkyl, aryl, aralkyl, alkoxy, thioalkoxy, cycloalkylalkoxy, heterocycloalkyl, aralkyloxy, or heteroaryl, and $R^5$ through $R^8$ are each independently any of these groups incorporating ester, amide, amine, hydroxyl, halogen, sulfonate, phosphonate, guanidine, and/or heteroaryl groups. In an alternate embodiment: groups $R^5$ through $R^8$ are each independently hydrogen, halogen, alkyl, cycloalkyl, aryl, aralkyl, alkoxy, thioalkoxy, cycloalkylalkoxy, heterocycloalkyl, aralkyloxy, or heteroaryl, and $R^1$ through $R^4$ are each independently any of these groups incorporating ester, amide, amine, hydroxyl, halogen, sulfonate, phosphonate, guanidine, and/or heteroaryl groups.

In an additional embodiment, the calixarene-based peptide mimetic has the structure described, and groups $R^1$ through $R^8$ are each independently hydrogen, alkyl, cycloalkyl, aralkyl, alkoxy, cycloalkylalkoxy, or aralkyloxy optionally including ester, amide, amine, hydroxyl, sulfonate, phosphonate, guanidine and/or heteroaryl groups. In a further embodiment, $R^1$ through $R^4$ are each independently alkyl, cycloalkyl, aralkyl, alkoxy, cycloalkylalkoxy, or aralkyloxy, and $R^5$ through $R^8$ are each independently any of these groups incorporating ester, amide, amine, hydroxyl, sulfonate, phosphonate, guanidine and/or heteroaryl groups. In a further, alternate, embodiment, $R^5$ through $R^8$ are each independently alkyl, cycloalkyl, aralkyl, alkoxy, cycloalkylalkoxy, or aralkyloxy, and $R^1$ through $R^4$ are each independently any of these groups incorporating ester, amide, amine, hydroxyl, sulfonate, phosphonate, guanidine and/or heteroaryl groups.

The terms "comprises" and variations thereof do not have a limiting meaning where these terms appear in the description and claims.

As used herein, "a," "an," "the," "at least one," and "one or more" are used interchangeably. Thus, for example, a composition comprising "a" calixarene-based peptide mimetic can be interpreted to mean that the composition includes "one or more" calixarene-based peptide mimetic. Furthermore, a "composition" as used herein can consist of just one calixarene-based peptide mimetic without any other components (e.g., a pharmaceutically acceptable carrier).

"Treat", "treating", and "treatment", etc., as used herein, refer to any action providing a benefit to a patient afflicted with a disease, including improvement in the condition through lessening or suppression of at least one symptom, delay in progression of the disease, prevention or delay in the onset of the disease, etc.

The invention is inclusive of the compounds described herein (including intermediates) in any of their pharmaceutically acceptable forms, including isomers (e.g., diastereomers and enantiomers), tautomers, salts, solvates, polymorphs, prodrugs, and the like. It should be understood that the term "compound" includes any or all of such forms, whether explicitly stated or not (although at times, "salts" are explicitly stated).

Also, the term "compound" includes the ionic form of the calixarene-based peptide mimetic (e.g., a positively charged calixarene-based peptide mimetic). As would be understood by those skilled in the art, the ionic forms of peptides are generally found associated with an appropriate counter-ion to result in a compound that has a neutral charge overall. However, an ionic calixarene-based peptide mimetic itself retains a charge (albeit a charge that is complemented by the opposite charge of the corresponding counter-ion), and will generally be found in a charged form when the salt is dissociated, as will occur when the salt form of the calixarene-based peptide mimetic is placed in an aqueous environment, such as when it is administered and released into an in vivo environment.

"Pharmaceutically acceptable" as used herein means that the compound or composition is suitable for administration to a subject to achieve the treatments described herein.

Room temperature, as defined herein, is the ambient temperature that a room used for human habitation is generally maintained at, and is generally a temperature from 20 to 25° C., with 22.5° C. being particularly preferred.

A group, as defined herein, is a group of elements that are traditionally referred to as a collective entity, either based on functionality or organizational convenience. An organic group, as defined herein, is a group that includes at least one carbon atom.

As used herein, the terms "alkyl", and the prefix "alk-" are inclusive of both straight chain and branched chain groups and of cyclic groups, e.g., cycloalkyl. Preferably, these groups contain from 1 to 20 carbon atoms. In some embodiments, these groups have a total of up to 10 carbon atoms, up to 8 carbon atoms, up to 6 carbon atoms, or up to 4 carbon atoms. The preferred size of the group will vary depending on the desired topography of the structure being mimicked. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "aryl" as used herein includes carbocyclic aromatic rings or ring systems. Examples of aryl groups include phenyl, naphtyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The terms ester, amide, amine, hydroxyl, halide, sulfonate, phosphonate, and guanidine refer to various different optional functional groups that may be included on groups attached to the topomimetic substrates of the invention. The functional groups are further described by the following chemical formulas: ester=—(CO)—O—; amide=—(CO)—NH—; amine=—$NH_2$, hydroxyl=—OH—; halogen is an element selected from the group consisting of F, Cl, Br, and I; sulfonate=—O—$SO_3^-$; phosphonate=—P(O)$(OH)_2$; and guanidine=—NH—C(=NH)—$NH_2$. An example of a group used in an embodiment of the invention that includes a halogen functional group is a trifluoromethyl group.

As used herein, the terms "alkoxy" and "thioalkoxy" refer to groups wherein two hydrocarbon alkyl groups are bonded to an oxygen or a sulfur atom, respectively. For example, a group represented by the formula —O—R is an alkoxy group, whereas a group represented by the formula —S—R is a thioalkoxy group. For example, a cycloalkylalkoxy group is an alkoxy group attached to a cycloalkyl group, whereas an aralkyloxy group is an alkoxy group attached to an aralkyl group, as defined herein. The R within an alkoxy or thioalkoxy group, described above, may be any aryl or alkyl group, as described herein.

When a group is present more than once in any formula described herein, each group is independently selected, whether explicitly stated or not.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 2 shows the chemical structures for the calixarene analogs in the helix/sheet topomimetic library. (a) Agents containing tertiary amine groups; (b) Agents containing guanidine groups; (c) Agents containing other basic and acidic groups; (d) Topology of a generic partial cone structure.

FIG. 4 shows tumor tissue cross-sections, stained with anti-CD45 and anti-CD8 antibodies, showing the effect of calixarene compounds 40 and 27 on general leukocyte and helper T-cell, respectively, infiltration into tumors. FIG. 4A shows the results with anti-CD8 antibodies and MA148 human ovarian carcinoma, while

FIG. 6 provides graphs and illustrations showing the bioactivity of topomimetics in in vitro and in vivo angiogenesis assays. (A) Proliferation of bFGF-stimulated HUVEC cultures was measured using a [$^3$H]-thymidine incorporation assay. Dose response curves up to 25 μM compound were performed for the calixarene derivatives and control βpep-25. Results are expressed as mean counts per minute (±SD) of three independent experiments from triplicate cultures. (B) The inhibitory effect on migration was determined using, the wound healing assay. A confluent layer of HUVECs was wounded and subsequently cultured with or without compounds (25 μM). Results are expressed as mean wound widths of duplicate cultures from three independent experiments. (C) In vivo angiogenesis inhibition in the chorioallantoic membrane assay (CAM). On day 10, compounds were added (25 μM) daily, and on day 14, photographs were taken on the CAM.

FIG. 7 provides graphs showing that topomimetics inhibit tumor growth in mice. MA148 tumor bearing mice were treated with βpep-25 (10 mg/kg/day), as well as the pharmacological and molar equivalent doses of 40 and 27. In all experiments, treatment was initiated after tumors were established. (A) Dose response for inhibition of MA148 tumor growth by 40. (B) 27 inhibits MA148 tumor growth. (C) B16 melanoma tumor growth is inhibited by 40 and 27 when continuously and systemically administered (osmotic minipump). (D) B16 melanoma tumor growth is inhibited by 40 and 27 when administered twice daily by intraperitoneal injections. In all studies, control animals were treated with PBS containing an equivalent amount of DMSO (30% v/v). Tumor volumes (±SEM) are plotted in $mm^3$ vs. days post inoculation. For the MA148 model, n=5-7 mice in each group; for the B16 model, n=6-10 in each group. All treatment groups inhibited tumor growth significantly compared to the control treated mice (p=0.001 using the two-way ANOVA analysis). In all panels, symbols are defined as: control ■, βpep-25 (βpep-25, 10 mg/kg) ●, 40 (2.4 mg/kg) Δ, 40 (10 mg/kg) ▲, 27 (2.7 mg/kg) ▽, and 27 (10 mg/kg) ▼.

DETAILED DESCRIPTION OF ILLUSTRATIVE EMBODIMENTS

Figure 1:
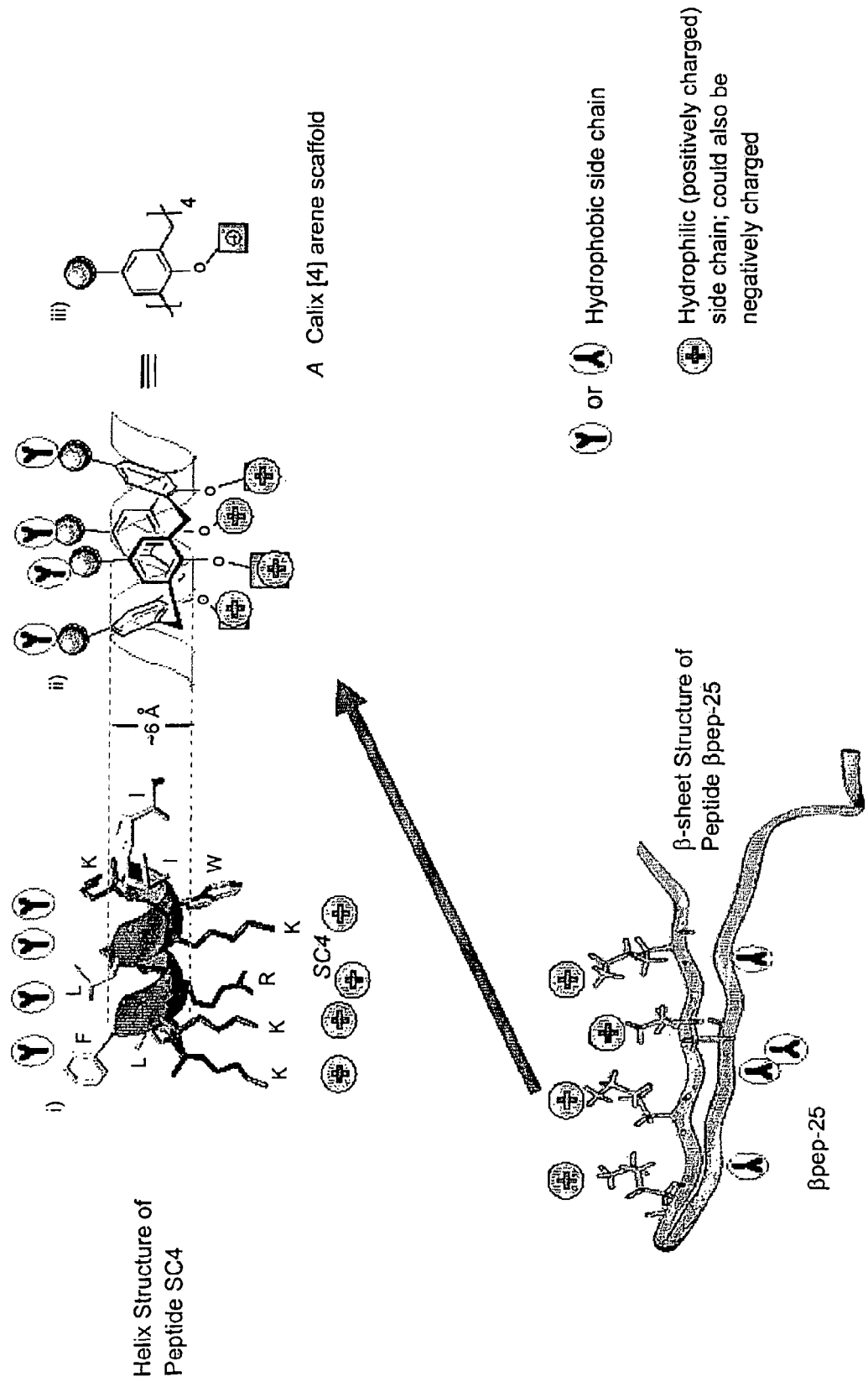
FIG. 1 shows the topological design features influencing the choice of the calix[4]arene scaffold for arraying hydrophobic and hydrophilic groups that mimic the structural and compositional characteristics of amphipathic helixes and sheets. The folded structures of SC4 and βpep-25 are shown at the top and bottom left, respectively, with hydrophobic and hydrophilic amino acid residues indicated.

The present invention is directed to a class of topomimetic compounds that provide a variety of biological activities. A topomimetic compound, as defined herein, is an organic compound that provides a surface topography that resembles that of an existing bioactive molecule. Topomimetic compounds of the present invention include peptide mimetics that use all organic scaffold together with particular groups to model the surface characteristics of peptides such as βpep-25 and SC4.

Topomimetic compounds of the present invention include calixarene-based peptide mimetics. A library of calixarene-based peptide mimetics have been prepared, and are shown herein to possess one or more biological activities. These biological activities include, for example, antibacterial activity, anti-angiogenic activity, and antitumor activity.

One aspect of the present invention relates to the ability to more fully mimic the folded conformations of small segments of helix and beta-sheet secondary protein structure, exemplified in two peptides (βpep-25 and SC4) with somewhat different biological activities, using calixarene in a scaffold-based approach method. βpep-25, is a designed cytokine-like β-sheet-forming peptide 33 mer (K. H. Mayo et al., Angiogenesis, 4, 45-51 (2001); and S. Liekens et al., J. Biochem. Pharm., 61, 253-270 (2001)). The other peptide, SC4, is a designed 12 mer that forms an amphipathic helix conformation, disrupts bacterial membranes selectively, and displays bactericidal activity (K. H. Mayo et al., Biochem. J. 2000, 349, 717-728). Although these examples provide proof of principle, the invention and approach itself has broader applications. In this regard, a fuller calixarene-based library of analogous compounds could be employed to search for activities in other systems whereby the biological activity can be mimicked.

The NMR-derived solution structures of designed βpep (e.g., βpep-25) and SC (e.g., SC4) peptides provided molecular dimensions from which to design an appropriate presentation scaffold. Although a number of potential scaffolds were considered, calix[4]arene chosen, based in part on the results of in silico molecular modeling, primarily because it represented most of the appropriate molecular dimensions of a small peptide in helix or beta-sheet conformation, as judged by NMR or X-ray crystallography. Furthermore, calix[4]arene is commercial available and can be readily used for the preparation of derivatives.

To exemplify the present invention'topomimetic design approach using the calixarene-based presentation scaffold, the peptides βpep-25 and SC4 were used. For the smart design of smaller compounds, the identification of specific amino acid residues and their spatial relationships provided the basic input for choosing appropriate calixarene-based peptide mimetics to be synthesized and tested. In solution, βpep-25 forms a beta-sheet, whereas SC4 forms a helical conformation. Based on amphipathic surface topology and rough molecular dimensions of these NMR-derived conformations (3-dimensional structures) of SC4 and βpep-25, mimetic design using a calixarene scaffold (see design scheme in FIG. 1) proved successful. These mimetics are non-peptidic (structures listed in FIG. 2), potentially orally active, and exhibit bactericidal, anti-angiogenic, and other biological activities in the μM to sub-μM range.

Note that the molecular dimensions of both folded peptides and the calixarene molecule are reasonably similar, being on the order of 5 Å to 10 Å in either one of 3 dimensions. The about 3-turn helix is a cylinder about 12 Å long ($\alpha$-$C_{N\text{-}term}$ to $\alpha$-$C_{C\text{-}term}$) and about 6 Å in diameter, similar to that of a small beta-sheet. The calixarene core is cone-shaped with the upper rim (as drawn) wider than the lower rim (about 8-10 vs. about 4-5 Å). The height of the calixarene core (from O to the first attachment atom of the para group) is about 6 Å. This 3D characteristic differentiates such calixarene-based mimetics from others known in the art. The calixarene skeleton constitutes an excellent template upon which to array sets of polar (cationic and anionic) and non-polar (hydrophobic) groups. For example, a calixarene skeleton can be provided with polar and non-polar groups in order to mimic the two surfaces of SC4, which include a hydrophilic surface presenting positively charged lysine and arginine residues and a hydrophobic surface including leucine, isoleucine, tryptophan, and phenylalanine residues.

While one embodiment of the invention uses a calixarene cone-shaped structure as a scaffold, an additional embodiment of the invention uses a partial cone structure as a scaffold, as shown in FIG. 2d. The partial cone structure decreases the difference between the two sides of the structure by reversing the orientation of one of the aryl groups of the calixarene ring, providing an alternative structure that may be useful for mimicking different polypeptide structures.

In particular embodiments, the calixarene-based peptide mimetics can be based on the structure-function relationships of peptides SC-4 and/or βpep-25 (preferably, of βpep-25). In particular, because these peptides fold as amphipathic structures, they can be mimicked by a chemical compound scaffold that includes one hydrophobic side to the molecule and another hydrophilic, positively charged side. By knowing the structure-activity relationships in these two peptides, the spatial relationships of key functional groups in both peptides, as well as the molecular dimensions present in these folded peptides, an organic scaffold can be identified. Herein, calixarene provides an appropriate chemical scaffold. The calixarene scaffold itself provides much of the appropriate molecular dimensions of a helix or beta-sheet backbone when in the folded state.

Calix[4]arenes-bis-rings are macrocyclic compounds often used in metal extractions. They have also been described as useful as antithrombotic agents in U.S. Pat. No. 5,409,959. Calixarene has been used only in one study as a scaffold to present and constrain small looped peptides that bind platelet-derived growth factor (Blaskovich et al., Nat. Biotechnol, 18; 1065-1070 (2000)), but not in the context of fully non-peptidic compounds as described herein.

Suitable calixarene-based peptide mimetics for use in the present invention include those having the following general structures, represented by Formula I and II:

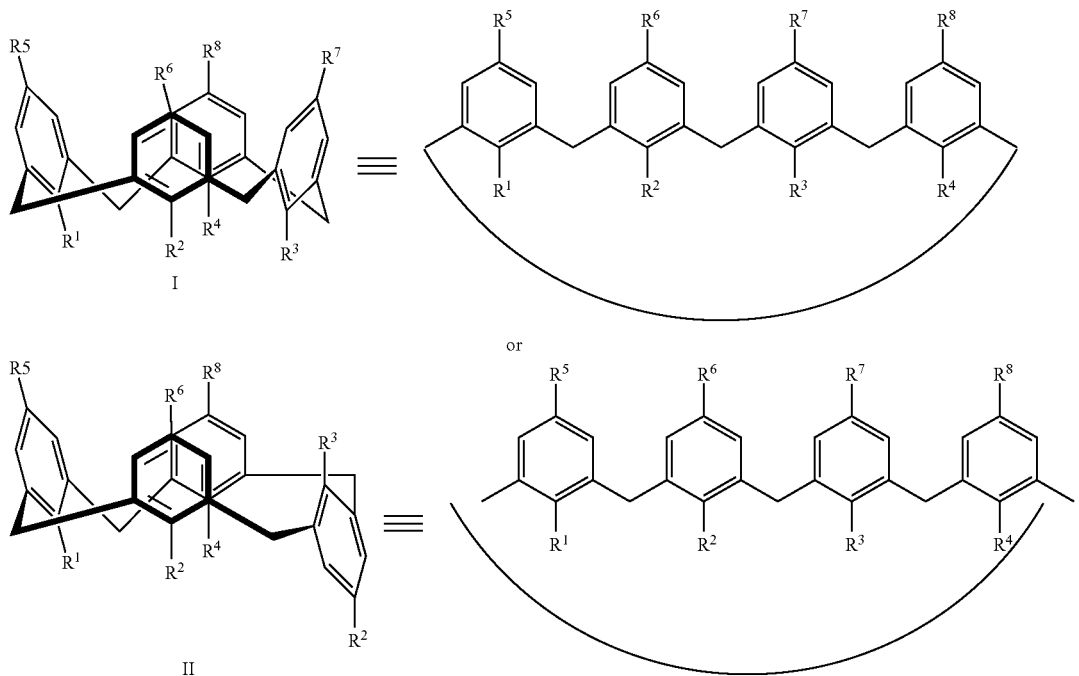

It should be noted that Formula I and Formula II represent different conformations of the calixarene-based peptide mimetics, but are otherwise the same. In the above structure, each $R^1$ through $R^8$ group is independently hydrogen or an organic group, wherein $R^1$ through $R^4$ are each independently hydrogen or an organic group of like polarity and $R^5$ through $R^8$ are each independently hydrogen or an organic group of like polarity that is of opposite polarity than those of $R^1$ through $R^4$. Preferably, $R^1$ through $R^8$ are each independently hydrogen, alkyl, cycloalkyl, aryl, aralkyl, alkoxy, cycloalkylalkoxy, heterocycloalkyl, aralkyloxy, trifluoromethyl, or halide, optionally including ester, amide, amine, hydroxyl, sulfonate, phosphonate, guanidine, heteroaryl, heteroarylalkyl, and/or thioalkoxy groups.

For example, $R^1$ through $R^4$ could be alkyl, cycloalkyl, aryl, aralkyl, alkoxy, cycloalkylalkoxy, heterocycloalkyl, aralkyloxy, heterocycloalkyl, aralkyloxy, trifluoromethyl, or halide and $R^5$ through $R^8$ could be any of these groups incorporating ester, amide, amine, hydroxyl, sulfonate, phosphonate, guanidine, heteroaryl, heteroarylalkyl, and/or thioalkoxy groups. Likewise, $R^5$ through $R^8$ could be alkyl, cycloalkyl, aryl, aralkyl, alkoxy, cycloalkylalkoxy, heterocycloalkyl, aralkyloxy, heterocycloalkyl, aralkyloxy, trifluoromethyl, or halide and $R^1$ through $R^4$ could be any of these groups incorporating ester, amide, amine, hydroxyl, sulfonate, phosphonate, guanidine, heteroaryl, heteroarylalkyl, and/or thioalkoxy groups.

Such calixarene-based peptide mimetics are active with respect to at least one of a number of biological activities. This is exemplified by the data shown herein. They can be as effective as, or more effective than, βpep-25 at one or more of its biological activities (for example, at inhibiting endothelial cell proliferation and angiogenesis in vitro). However, even if a calixarene-based peptide mimetic is not as effective as, or is not more effective than, βpep-25 at one or more of its biological activities, the compound can be useful. This is particularly true if the compound is more bioavailable than βpep-25, has fewer side effects than βpep-25, and/or is cheaper to produce than βpep-25, for example.

Compounds such as the calixarene-based peptide mimetics described herein can be identified and prepared using a method of the present invention for designing peptide mimetics. Herein, such peptide mimetics possess surface properties and topology that substantially mimic at least a portion of the peptide and have at least one of the biological functions of the peptide.

A method of preparing a peptide mimetic is illustrated in FIG. 1 and involves the following steps: identifying a folded structured peptide of interest (e.g., βpep-25 (β-sheet peptide) and SC4 (helix peptide) in FIG. 1); determining a biologically active region of the peptide and key functional groups within the biologically active region responsible for the biological activity of that region of the peptide (amphipathic elements, i.e., one primarily hydrophobic surface, and one primarily hydrophilic, in this case positively charged, surface); identifying an organic scaffold for presenting the key functional groups or analogs thereof in a spatial orientation equivalent to that in the biologically active region (calix[4]arene as shown in FIG. 1 with generic functional groups (hydrophobic and positively charged hydrophilic groups) that vary as shown in FIG. 2, or the like; and synthesizing a compound comprising the scaffold and key functional groups or analogs thereof to form a peptide mimetic of the peptide of interest (see FIG. 2). Examples of preferred calixarene-based peptide mimetics are illustrated in FIG. 2.

The biologically active region is preferably the smallest region of the peptide that can elicit a biological response. The key functional groups within this region are those functional groups of the amino acid side chains primarily responsible for the biological response elicited by the identified region. The biologically active region and key functional groups can be identified using standard structure-activity methods, such as truncating the peptide, using alanine scanning, and the like. These key functional groups or analogs thereof are hydrophobic groups, aliphatic and/or aromatic and hydrophilic groups, positively or negatively charged or non-charged. Analogous organic groups can be used as groups to the calixarene ring to mimic various amino acid side chains. For example, an alkyl group can be used to mimic the side chains of valine, isoleucine, and leucine; alkyl amine groups mimic the side chains of lysine; alkyl guanidine groups mimic the side chains of arginine; alkyl ester groups mimic the side chains of aspartate and glutamate, alkyl amide groups mimic the side chains of asparagines and glutamine, and heteroaryl groups mimic the side chains of histidine and tryptamine.

These group organic groups are then combined with an organic scaffold. In order to mimic an amphiphilic molecule, the groups can be placed such that they present hydrophobic groups primarily on one face of an organic scaffold and hydrophilic groups primarily on the opposite face of an organic scaffold. An organic scaffold provided with hydrophobic and hydrophilic groups should have a similar molecular dimension to the biologically active region of the peptide of interest and have key functional groups or analogs thereof in a spatial orientation that is substantially the same as that of the functional groups in the biologically active region of the peptide of interest. In this context "equivalent" does not mean that functional groups or analogs thereof have to be in precisely the same spatial orientation as in the peptide of interest, but they should be in a substantially similar orientation such that the resultant peptide mimetic possesses at least one of the same biological functions as that of the peptide of interest (although it does not have to be at the same level of activity).

The organic scaffold can be of a wide variety of structures, which can be in a wide variety of shapes. It is particularly desirable that the shape of the scaffold be disc-shaped. Preferably, the thickness or height of such a disc is up to 10 Angstroms (and typically, within a range of 5-7.5 Angstroms). Preferably, the longest dimension (typically, the diameter) of the disc is up to 20 Angstroms (and typically, within a range of 10-15 Angstroms (Å)). In a typical peptide mimetic, at least two surfaces (typically, the surfaces having the largest areas, and more typically, the opposite faces of a disc) are modified to include the key functional groups or analogs thereof. Typically, regardless of the size of the core of the scaffold, the surface "skin" of the scaffold (formed by the functional groups on the surface(s)) is typically substantially similar to βpep-25 and/or SC4.

In certain embodiments of this method, the organic scaffold is calixarene and the peptide mimetic is a calixarene-based peptide mimetic (see FIG. 1). In certain embodiments of this method, the peptide of interest is βpep-25 or SC4.

Figure 3:
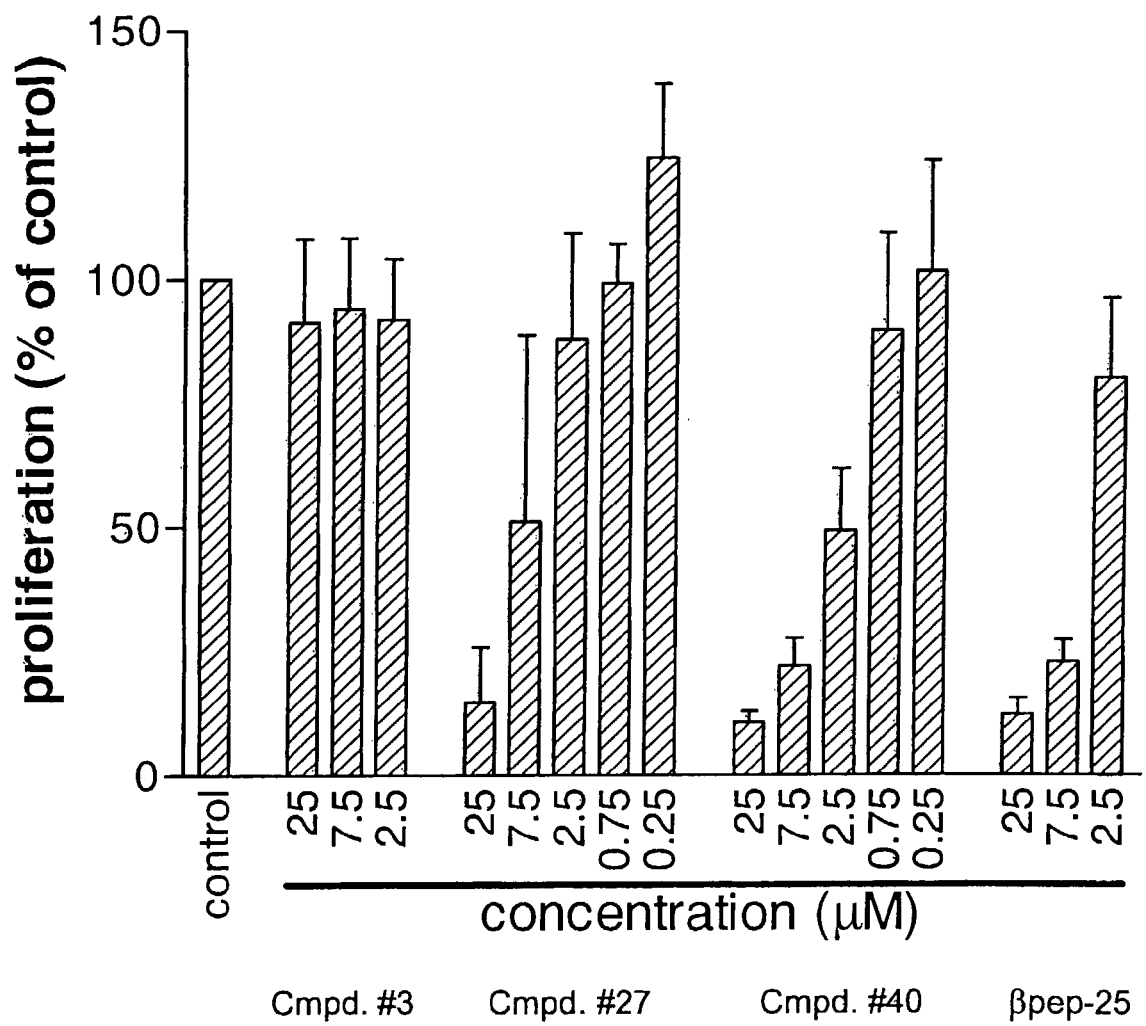
FIG. 3 shows inhibition of endothelial cell (EC) proliferation data for 3 calixarene derivatives (40, 11 and 27).

In an initial set of experiments, in vitro activities were assessed using primarily bactericidal and endothelial cell proliferation assays, as described in Example 36. This example used calixarene-based peptide mimetics prepared as described in Examples 1-35. From this small library, two of these compounds were found to have reasonably good bactericidal activity (Compounds 3 and 11) in the micromolar range (Table 1), and a different two were found to have exceptional antiangiogenic activity (Compound 27 and 40) (Table 1 and FIG. 3). Others shown in Table 1 were much less active in these assays, but could be active if assessed in other assays for different biological activities.

TABLE 1

| Compound | Structure | EC proliferation IC$_{50}$ (conc, μM) | EC % Apoptosis 25 μM | EC % total cell death 25 μM | Other cells 25 μM, | Bacterial activity on J96 IC$_{50}$ (conc, μM) | Hemolysis | Solubility |
|---|---|---|---|---|---|---|---|---|
| βpep-25 | 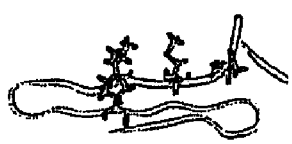 | 5.5 | 28% (75%, BJ) | 60% | Fibro 85% MA148 30% SCK 60% | | None at 10$^{-4}$M | 3 mM in 0.15M NaCl |
| 6DBF7 | 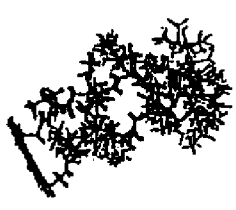 | 25 | No effect | | | | | DMSO H$_2$O |
| SC4 | 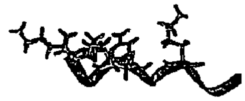 | None up to 100 | No effect | | | 0.5 | None at 10$^{-4}$M | 3 mM in 0.15M NaCl |
| 40 | 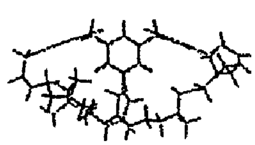 | 2.5 | No effect | No effect | Fibro 0% MA148 80% SCK 40% | None up to 3.8 | None at 10$^{-5}$M | H$_2$O up to 30 mg/ml at pH < 7.0, r.t. |

TABLE 1-continued

| Compound | Structure | EC proliferation IC$_{50}$ (conc, μM) | EC % Apoptosis 25 μM | EC % total cell death 25 μM | Other cells 25 μM, | Bacterial activity on J96 IC$_{50}$ (conc, μM) | Hemolysis | Solubility |
|---|---|---|---|---|---|---|---|---|
| 41 | 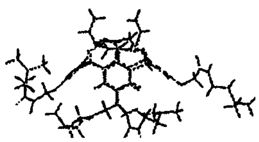 | None up to 25 | | | | 2.4 | 100% at 10$^{-5}$M | Goes into solution in H$_2$O after dissolving in DMSO |
| 7 | 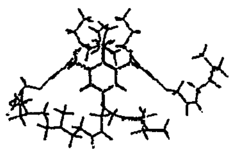 | None up to 25 | | | | 1.6 | 100% at 10$^{-6}$M | DMSO/H$_2$O |
| 3 | 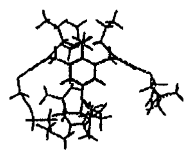 | None up to 25 | No effect | No effect | Fibro 100% | 1.3 | 100% at 10$^{-6}$M | DMSO/H$_2$O |
| 5 | 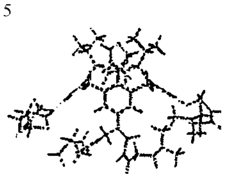 | None up to 25 | | | | 0.7 | 100% at 10$^{-6}$M | DMSO/H$_2$O |
| 2 | 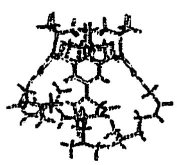 | None up to 25 | | | | 1.1 | 100% at 10$^{-6}$M | DMSO/H$_2$O |
| 23 | | None up to 25 | | | | None up to 3.8 | | DMSO/H$_2$O |
| 4 | | None up to 25 | | | | None up to 3.8 | | DMSO/H$_2$O |
| 4 + bridged derivatives | 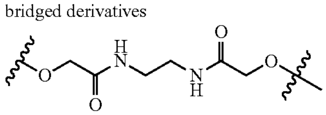 | 10 | | | | None up to 3.8 | | DMSO/H$_2$O |
| 45 | | None up to 25 | | | | None up to 3.8 | | Goes into solution in H$_2$O after dissolving in ethanol |
| 27 | 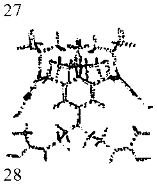 | 8.3 | No effect | 65% | Fibro 100% MA148 100% SCK 100% | None up to 3.8 | 100% at 10$^{-6}$M | DMSO/H$_2$O (30/70%) up to 30 mg/ml at >80 °C., no infl. of pH 2 ÷ 11 |
| 28 | 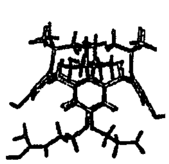 | None up to 25 | | | | 2.5 | | DMSO/H$_2$O |

TABLE 1-continued

| Compound | Structure | EC proliferation IC$_{50}$ (conc, μM) | EC % Apoptosis 25 μM | EC % total cell death 25 μM | Other cells 25 μM, | Bacterial activity on J96 IC$_{50}$ (conc, μM) | Hemolysis | Solubility |
|---|---|---|---|---|---|---|---|---|
| 43 | 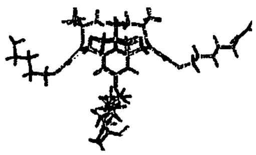 | None up to 25 | | | | 1.4 | | DMSO/H$_2$O |
| 32 | 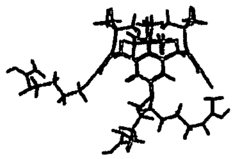 | None up to 25 | | | | 1.3 | | DMSO/H$_2$O |
| 21 38 39 36 | | None up to 25 | | | | 1.2 | | DMSO/H$_2$O |

Figure 4A:
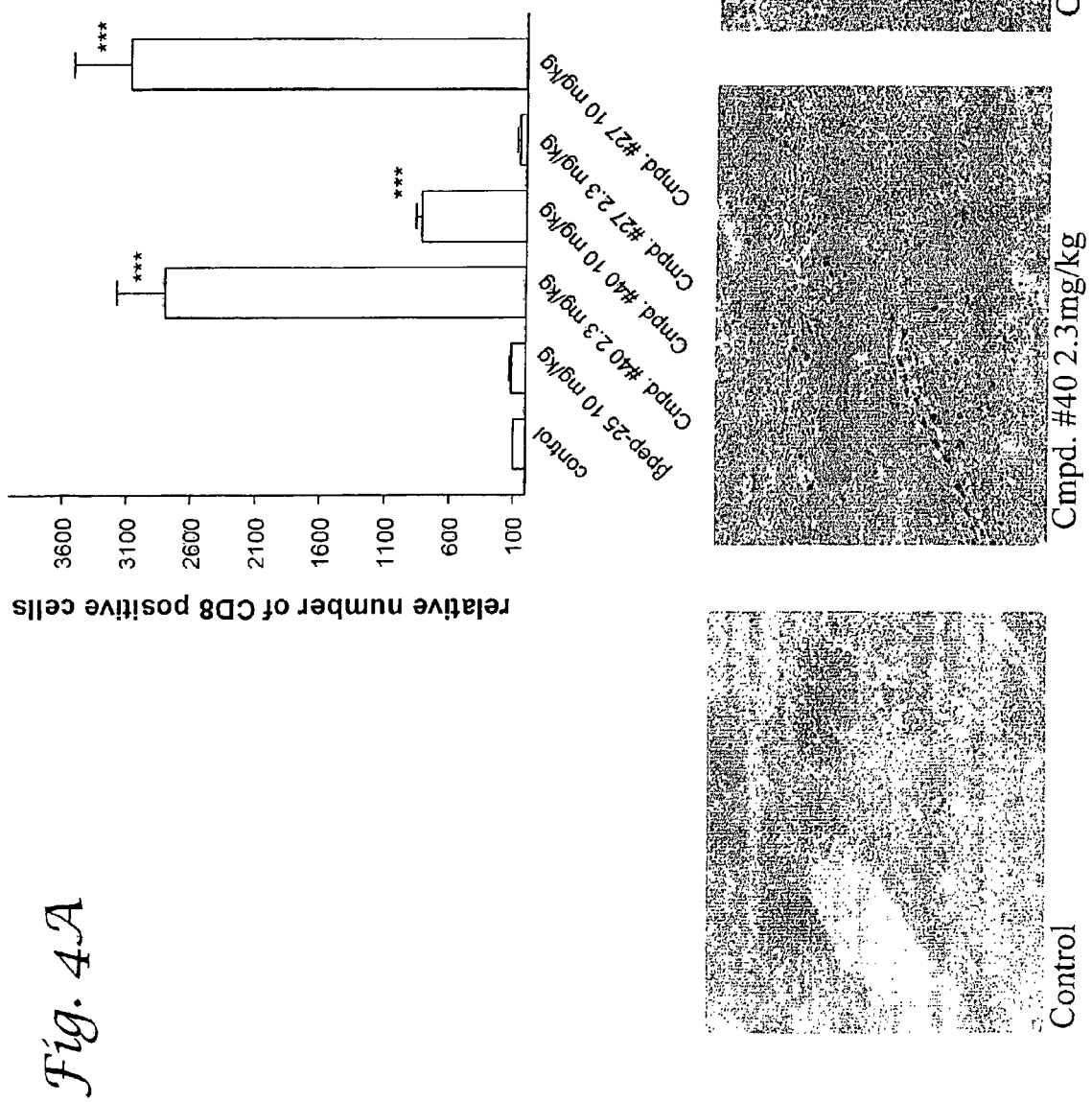
Figure 4B:
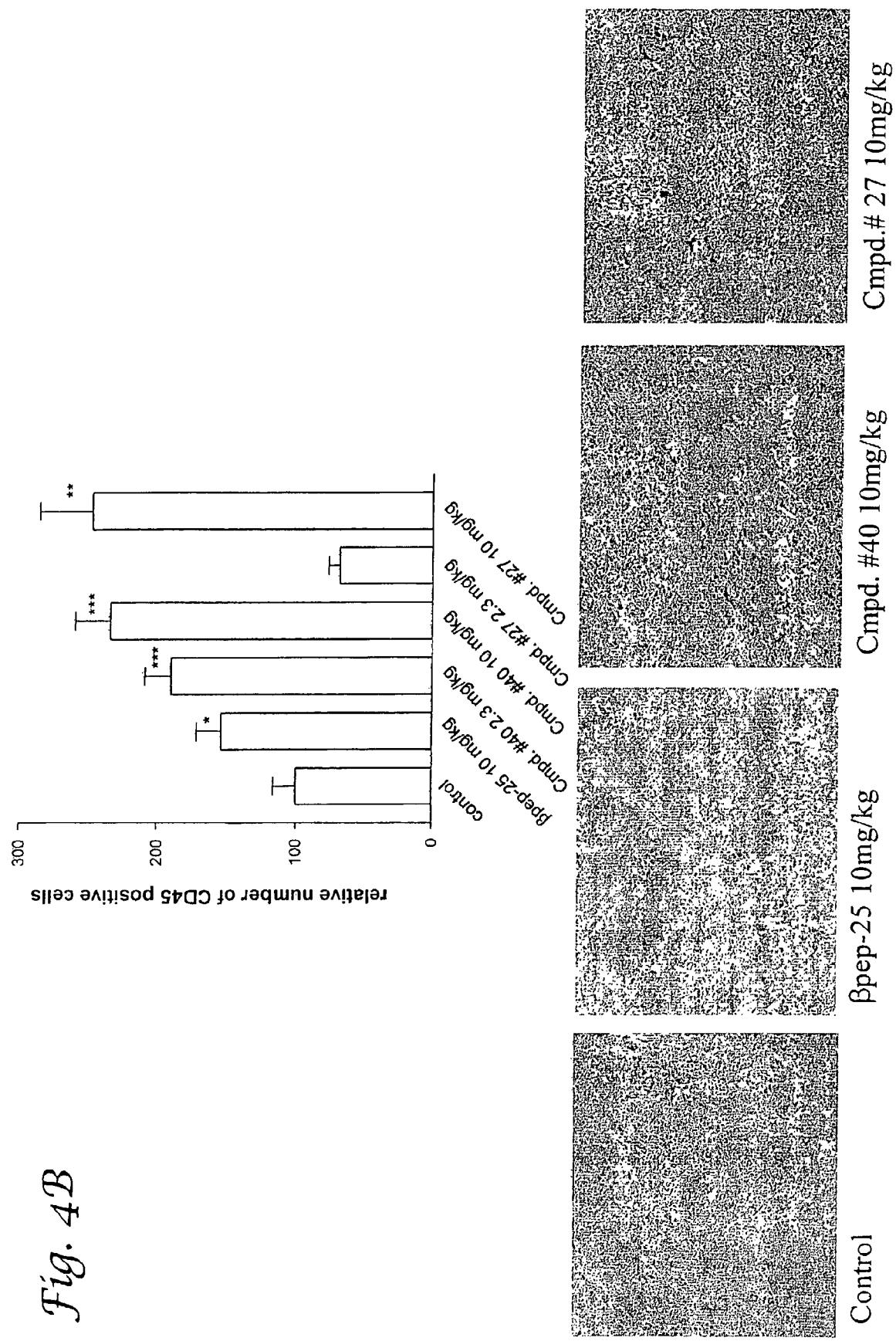
FIG. 4B shows the results with anti-CD45 antibodies and B16 mouse melanoma.

Tumor-bearing mice were treated with two of the compounds (KM0118 (40) and Compound 27), and tumor growth (MA148 human ovarian carcinoma, and B16 mouse melanoma) was found in each case to be significantly inhibited (FIG. 4A (MA148) and FIG. 4B (B16)), either the same as or better than with βpep-25.

In a further set of experiments, in vitro activities were assessed for their ability to neutralize LPS (i.e., endotoxin), their ability to inhibit endothelial cell proliferation and migration, their ability to inhibit tumor growth, and their antiangiogenic activity, as described in Example 47. The ability of various compounds to inhibit LPS binding is shown in Table 2. Further data on the ability of compounds to inhibit LPS binding is provided in Table 3 in the Examples section. These experiments used calixarene-based peptide mimetics prepared as described in Examples 1-35 and Examples 37-46. From this library of 23 compounds, which are shown in FIG. 2, compounds 12, 42, 43, 15, 46a, and 19 were shown to be most effective for neutralizing LPS, while compounds 27 and 40 were most active as anti-angiogenic agents. None of the compounds tested exhibited significant toxicity. Calixarene-based peptide mimics that presented hydrophobic and positively charged groups were particularly effective for neutralizing endotoxin. The highly effective antiangiogenic and antitumor compounds 27 and 40 have a net positive charge and amphipathic character as well.

TABLE 2

Calixarene Derivatives. IC$_{50}$ values (μM) for LPS binding

| Samples | E. coli 055:B4 | E. coli 0111:B4 | P.a. | Klebsiella | Salmonella | Serratia |
|---|---|---|---|---|---|---|
| Tertiary Amine Derivatives | | | | | | |
| | 3.4 | >5 | ND | 1.5 | ND | >5 |
| | >5 | 1.4 | >5 | 1.5 | 0.6 | 3.4 |
| | 4.4 | >5 | ND | 0.08 | 4.1 | ND |
| | 0.05 | 2.7 | ND | 0.4 | 0.8 | ND |
| | 0.006 | 3.1 | 4.2 | 1 | 0.4 | ND |

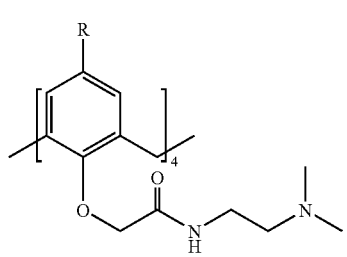

40 R = H
2 R = t-butyl
3 R = propyl
4 R = propyl
   Partial cone*
5 R = isobutyl

TABLE 2-continued
Calixarene Derivatives. IC$_{50}$ values (μM) for LPS binding
| Samples | E. coli 055:B4 | E. coli 0111:B4 | P.a. | Kleb-siella | Salmo-nella | Serra-tia |
|---|---|---|---|---|---|---|
| | 3.6 | 4.7 | >5 | ND | >5 | ND |
| | 3.8 | 3.7 | >5 | 2.1 | 3.1 | ND |
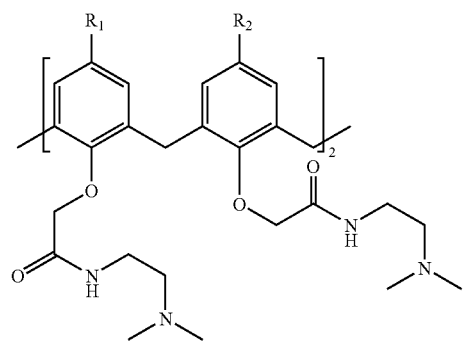
6 R$_1$ = methally
 R$_2$ = allyl
7 R$_1$ = isobutyl
 R$_2$ = propyl
| | >5 | >5 | ND | 2.4 | 3.2 | ND |
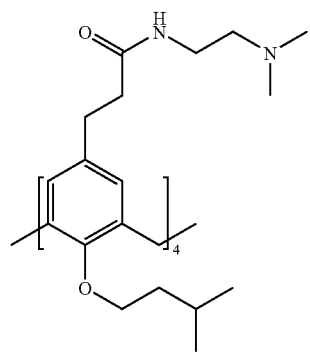
8
| | >5 | >5 | ND | ND | >5 | ND |
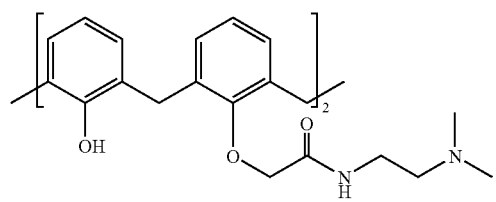
9

TABLE 2-continued
Calixarene Derivatives. IC$_{50}$ values (μM) for LPS binding
| Samples | E. coli 055:B4 | E. coli 0111:B4 | P.a. | Kleb-siella | Salmo-nella | Serra-tia |
|---|---|---|---|---|---|---|
| Guanidine Derivatives | | | | | | |
| | >5 | ND | ND | ND | 4.4 | ND |
| | 4.1 | 3.9 | ND | ND | >5 | ND |
| | 0.04 | 0.7 | 1.5 | 1 | 0.6 | ND |
| | 0.1 | 0.4 | 0.8 | 0.5 | 0.6 | 3.2 |
| | 4.1 | >5 | ND | ND | 2.6 | ND |
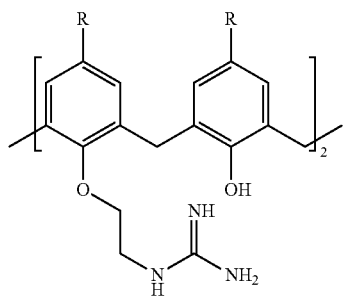
10 R = t-butyl
11 R = H
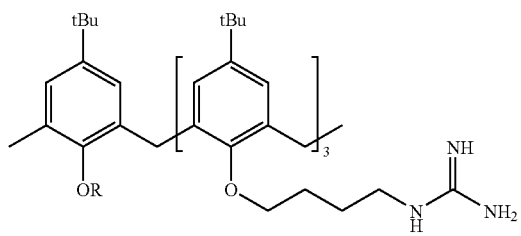
42 R = (CH$_2$)$_4$NHC(=NH)NH$_2$
43 R = (CH$_2$)$_4$NH$_2$
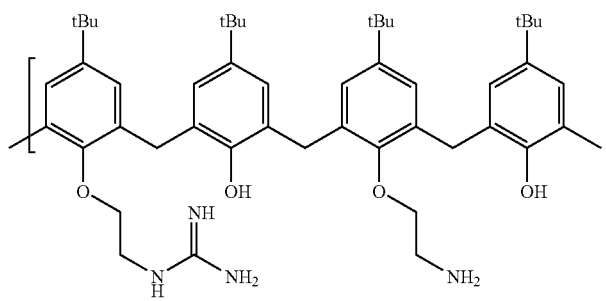

TABLE 2-continued

Calixarene Derivatives. IC$_{50}$ values (μM) for LPS binding

| Samples | E. coli 055:B4 | E. coli 0111:B4 | P.a. | Klebsiella | Salmonella | Serratia |
|---|---|---|---|---|---|---|
| Triazole Derivative | | | | | | |
| 15 | ND | ND | ND | ND | ND | ND |
| Primary Amine Derivative | | | | | | |
| 46a | 0.05 | 2.2 | 2.6 | 1 | 1.1 | >5 |
| 46b Partial Cone* | 0.6 | 1.5 | 1 | 0.9 | ND | ND |
| 19 | 0.9 | 1.6 | 0.8 | 0.3 | 0.6 | 1.5 |
| 45 | 1.3 | 0.1 | 0.5 | 1 | 0.2 | 4.5 |

TABLE 2-continued

Calixarene Derivatives. IC$_{50}$ values (μM) for LPS binding

| Samples | E. coli 055:B4 | E. coli 0111:B4 | P.a. | Kleb-siella | Salmo-nella | Serra-tia |
|---|---|---|---|---|---|---|
| 20 | >5 | >5 | ND | ND | 1.2 | ND |

Negatively Charged Derivatives

| | >5 | >5 | ND | ND | ND | ND |
|---|---|---|---|---|---|---|
| | >5 | ND | ND | ND | ND | ND |
| | 5 | 5 | ND | 2.1 | ND | 4.2 |

47 R = CO$_2$H
48 R = CH$_2$P(O)(OH)$_2$
49 R = CH$_2$OSO$_3$H

Peptides

| | | | | | | |
|---|---|---|---|---|---|---|
| SC4 | 4.2 | >5 | 4 | ND | 4 | >5 |
| β-pep-25 | 2.5 | 2 | 1.2 | 2 | 2.5 | 4.1 |
| PmxB | 0.03 | 0.03 | 0.003 | 0.01 | 0.1 | ND |

ND = no detectable activity at 5 × 10$^{-6}$ M
>5 = minimal activity at 5 × 10$^{-6}$ M; no IC$_{50}$ determined.
Values in sub-micro molar range are shown in bold.
* Generic Structure of Calixarene in Partial Cone Conformation

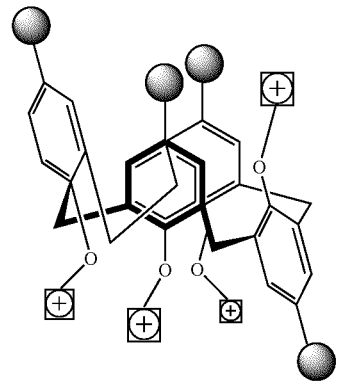

A preferred calixarene-based peptide mimetic is characterized by having at least one of the biological activities described herein. The biological activity of a compound can be determined, for example, as described herein or by methods well known to one of skill in the art.

Compositions that include one or more of the calixarene-based peptide mimetics of this invention with an optional carrier (e.g., a pharmaceutically acceptable carrier) can be added to cells in culture or used to treat patients, such as mammals. Where the calixarene-based peptide mimetics are used to treat a patient, the calixarene-based peptide mimetic is preferably combined in a pharmaceutical composition with a pharmaceutically acceptable carrier, such as a larger molecule to promote stability or a pharmaceutically acceptable buffer that serves as a carrier.

Treatment can be prophylactic or therapeutic. Thus, treatment can be initiated before, during, or after the development of the condition (e.g., bacterial infection or endotoxemia). As such, the phrases "inhibition of" or "effective to inhibit" a condition such as bacterial infection and/or endotoxemia, for example, includes both prophylactic and therapeutic treatment (i.e., prevention and/or reversal of the condition).

The calixarene-based peptide mimetics of the present invention can be administered alone or in a pharmaceutically acceptable buffer, as an antigen in association with another protein, such as an immunostimulatory protein or with a protein carrier such as, but not limited to, keyhole limpet hemocyanin (KLH), bovine serum albumin (BSA), ovalbumin, or the like. It can also be used in adjuvant therapy, in combination with, for example, a chemotherapeutic agent like carboplatin or others known to one skilled in the art.

The calixarene-based peptide mimetics can be combined with a variety of physiological acceptable carriers for delivery to a patient including a variety of diluents or excipients known to those of ordinary skill in the art. For example, for parenteral administration, isotonic saline is preferred. For topical administration a cream, including a carrier such as dimethylsulfoxide (DMSO), or other agents typically found in topical creams that do not block or inhibit activity of the peptide, can be used. Other suitable carriers include, but are not limited to alcohol, phosphate buffered saline, and other balanced salt solutions.

The calixarene-based peptide mimetics of this invention that demonstrate biological activity can be administered in a variety of ways, including intravenously, topically, orally, and intramuscularly to a variety of mammals, including humans, mice and rabbits. The calixarene-based peptide mimetics can be administered as a single dose or in multiple doses. Preferably the dose is an effective amount as determine by the standard methods described herein and includes about 1 microgram to about 1,000 micrograms pretreatment, more preferably about 50 to about 250 micrograms pretreatment. Those skilled in the art of clinical trials will be able to optimize dosages of particular calixarene-based peptide mimetics through standard trial studies.

In one embodiment, calixarene-based peptide mimetics are anti-angiogenic. Angiogenesis is involved in numerous biological functions in the body, from normal processes like embryogenesis and wound healing to abnormal processes like tumor growth, arthritis, restenosis, atherosclerosis, diabetic retinopathy, neovascular glaucoma, and endometriosis. The use of agents that can inhibit angiogenesis ill vitro and in vivo, particularly in anti-tumor research, has indicated that anti-angiogenic therapy is a promising therapeutic modality. The search for angiogenic inhibitors has been focused on controlling two of the processes that promote angiogenesis: endothelial cell (EC) growth and adhesion, primarily because ECs are more accessible than are other cells to pharmacologic agents delivered via the blood and ECs are genetically stable and are not easily mutated into drug resistant variants. Most anti-angiogenic agents have been discovered by identifying endogenous molecules, primarily proteins, which inhibit EC growth.

It has also been postulated that tumor growth can be controlled by deprivation of vascularization (Folkman J. Natl. Cancer. Inst. 82, 4-6 (1990); Folkman et al., J. Biol. Chem., 267, 10931-10934 (1992)). A growing number of endogenous inhibitors of angiogenesis such as platelet factor-4 (PF4), interferon-γ inducible protein-10 (IP-10), thrombospondin-1 (TSP-1), angiostatin, as well as synthetic agents, e.g., thalidomide, TNP-470, and metalloproteinase inhibitors have been described. Some of these agents are currently being tested in phase I/II clinical trials. Previous research described in Griffioen et al., Blood, 88, 667-673 (1996), and Griffioen et al., Cancer Res., 56, 1111-1117 (1996) has shown that pro-angiogenic factors in tumors induce down-regulation of adhesion molecules on endothelial cells in the tumor vasculature and induce anergy to inflammatory signals such as tumor necrosis factor α (TNF-α), interleukin-1, and interferon-γ. EC exposed to vascular endothelial cell growth factor (VEGF) (Griffioen et al., Blood, 88, 667-673 (1996)) and basic fibroblast growth factor (bFGF) (Griffioen et al., Blood, 88, 667-673 (1996); and Melder et al., Nature Med., 2, 992-997 (1996)) have a severely hampered up-regulation of intercellular adhesion molecule-1 (ICAM-1) and induction of vascular cell adhesion molecule-1 (VCAM-1) and E-selectin. This phenomenon, which was named tumor-induced EC anergy, is one way in which tumors with an angiogenic phenotype may escape infiltration by cytotoxic leukocytes.

Because angiogenesis-mediated down-regulation of endothelial adhesion molecules (EAM) may promote tumor outgrowth by avoiding the immune response (Griffioen et al., Blood, 88, 667-673 (1996); Kitayama et al., Cancer. Res., 54, 4729-4733 (1994); and Piali et al., J. Exp. Med., 181, 811-816 (1995)), it is believed that inhibition of angiogenesis would overcome the down-regulation of adhesion molecules and the unresponsiveness to inflammatory signals. In support of this hypothesis, a relation between E-selectin up-regulation and the angiostatic agent AGM-1470 has been reported (Budson et al., Biochem. Biophys. Res. Comm., 225, 141-145 (1996)). It has also been shown that inhibition of angiogenesis by PF-4 up-regulates ICAM-1 on bFGF-simulated EC. In addition, inhibition of angiogenesis by PF4 overcomes the angiogeniesis-associated EC anergy to inflammatory signals.

Thus, the present invention provides a method for inhibiting endothelial cell proliferation in a patient (e.g., a mammal such as a human). This involves administering to a patient an amount of a composition (typically a pharmaceutical composition) effective to inhibit the growth or endothelial cells, wherein the composition includes one or more calixarene-based peptide mimetics described herein. Analogously, the present invention provides a method for inhibiting endothelial cell proliferation in vitro (e.g., in a cell culture). This method involves contacting cells with an amount of a composition effective to prevent and/or reduce the growth of endothelial cells, wherein the composition includes one or more calixarene-based peptide mimetics described herein.

For determining the amount of endothelial cell proliferation in vivo, various methods known to one of skill in the art could be used. For example, for evaluation of endothelial cell growth in tumors, tissue sections can be appropriately stained to quantify vessel density. For determining the amount of endothelial cell proliferation in vitro, an EC Proliferation Assay can be used that involves the uptake of tritiated thymidine by cells in cell culture. A calixarene-based peptide mimetic that is "active" for inhibiting endothelial cell proliferation is preferably one that causes an at least 10% reduction in endothelial cell proliferation at a concentration lower than $10^{-4}$ M. Alternatively, inhibition of endothelial cell proliferation for an "active" calixarene-based peptide mimetic in vitro is preferably at an IC50 level of less than 80 µM (more preferably less than 50 µM, and even more preferably less than 25 µM) as determined using the assay described in the Examples Section.

The present invention also provides a method for inhibiting angiogenic-factor mediated inter-cellular adhesion molecule (ICAM) expression down-regulation (and/or promoting ICAM expression) in a patient (e.g., a mammal such as a human). This involves administering to a patient an amount of a composition effective to prevent and/or reduce the amount of ICAM expression down-regulation, wherein the composition includes one or more calixarene-based peptide mimetics described herein. Analogously, the present invention provides a method for inhibiting angiogenic-factor mediated inter-cellular adhesion molecule expression down-regulation (and/or promoting ICAM expression) in vitro (e.g., in a cell culture). This method involves contacting cells with an amount of a composition effective to prevent and/or reduce the amount of ICAM expression down-regulation, wherein the composition includes one or more calixarene-based peptide mimetics described herein.

The present invention also provides a method for increasing the infiltration of leukocytes into tumor tissue in a patient (e.g., a mammal such as a human). This involves administering to a patient an amount of a composition effective to increase the amount of white blood cells (leukocytes) that can infiltrate into the tumor tissue through blood vessels, wherein the composition includes one or more calixarene-based peptide mimetics described herein. The use of agents that can increase leukocyte infiltration into tumor tissue, particularly in anti-tumor research, has been sought for some time and in the general area of immunotherapy and will be a promising therapeutic modality in the future. This is exemplified in FIG. 4, which shows the effects of two of these agents (KM0118 (40) and Compound 27) at increasing leukocyte infiltration into tumors of tumor-bearing mice.

The present invention provides a method for inhibiting angiogenesis (i.e., new blood vessel formation) in a patient (e.g., a mammal such as a human). This involves administering to a patient an amount of a composition effective to prevent and/or reduce angiogenesis, wherein the composition includes one or more calixarene-based peptide mimetics described herein. Analogously, the present invention provides a method for inhibiting angiogenesis in vitro (e.g., in a cell culture). This method involves contacting cells with an amount of a composition effective to prevent and/or reduce angiogenesis, wherein the composition includes one or more calixarene-based peptide mimetics described herein.

For determining the amount of angiogenesis in vivo, various methods known to one of skill in the art could be used. For example, for evaluation of angiogenesis in tumors, tissue sections can be appropriately stained to quantify vessel density. For determining the amount of angiogenesis in vitro, an Angiogenesis Assay can be used that involves the disappearance of EC sprouting in cell culture. A polypeptide that is "active" for angiogenesis inhibition is preferably one that causes an at least 10% reduction in endothelial cell sprouting at a concentration lower than $10^{-4}$ M. Alternatively, inhibition of angiogenesis for a calixarene-based peptide mimetic in vitro is preferably at a level of less than 85% sprouting (more preferably less than 75% sprouting, even more preferably 50% sprouting, and even more preferably less than 35%) as determined using the collagen gel-based assay described in the Examples Section.

Similarly, such anti-angiogenic compositions can be used to control pathologic disorders such as atherosclerosis, restenosis, diabetic retinopathy, neovascular glaucoma, rheumatoid arthritis, and endometriosis. This can be demonstrated using standard techniques and models known to one of skill in the art.

The present invention provides a method for inhibiting tumorigenesis in a patient (e.g., a mammal such as a human). This involves administering to a patient an amount of a composition effective to prevent and/or reduce tumor growth, wherein the composition includes one or more calixarene-based peptide mimetics described herein. Methods of determining the inhibition of tumorigenesis are well known to those of skill in the art, including evaluation of tumor shrinkage, survival, etc.

The present invention provides a method for treating bacterial infection and/or endotoxemia in a patient (e.g., a mammal such as a human). This involves administering to a patient an amount of a composition effective to inhibit the bacterial infection and/or to neutralize endotoxin, wherein the pharmaceutical composition includes one or more calixarene-based peptide mimetics described herein. Analogously, the present invention provides a method for inhibiting bacterial infection and/or endotoxemia in vitro (e.g., in a cell culture). This method involves contacting cells with an amount of a composition effective to inhibit the bacterial infection and/or to neutralize endotoxin, wherein the composition includes one or more calixarene-based peptide mimetics described herein.

In both the in vivo and in vitro methods, "inhibiting" a bacterial infection includes preventing as well as reversing or reducing the growth of bacteria in a patient or a cellular sample, and "neutralizing" endotoxin includes binding LPS and thereby removing it from the system of a patient or a cellular sample. The level of bacterial infection can be determined according to known bactericidal assays. The level of endotoxemia can be determined according to known LPS neutralization assays. These assays can be used to determine the effectiveness of a polypeptide, whether used in vivo or in vitro. To determine the effectiveness of the treatment of a patient having a bacterial infection, a blood sample can be taken, a culture developed, and the amount of live bacteria determined. To determine the effectiveness of the treatment of a patient having endotoxemia, a blood sample can be taken, a culture developed, and the amount of cytokines (e.g., TNF-α, IL-1) can be determined using methods known to one of skill in the art. For example, the WEHI assay can be used for the detection of TNF-α (Battafarano et al., Surgery 118, 318-324 (1995)).

The effective amount of a calixarene-based peptide mimetic of the present invention will depend on the condition being treated and on the desired result. For example, treating a bacterial infection will depend on the bacterial infection, the location of the infection, and the calixarene-based peptide mimetic. An effective amount of the calixarene-based peptide mimetic for treating bacterial infection is that amount that diminishes the number of bacteria in the animal and that diminishes the symptoms associated with bacterial infection such as fever, pain, and other associated symptoms of the bacterial infection. The effective amount of a calixarene-based peptide mimetic can be determined by standard dose response methods.

Alternatively, an effective amount of a calixarene-based peptide mimetic for treating a bacterial infection can be determined in an animal system such as a mouse. Acute peritonitis can be induced in mice such as outbred Swiss webster mice by intraperitoneal injection with bacteria such as *P. aeruginosa* as described by Dunn et al. (Dunn et al. Surgery, 98, 283 (1985)); and Cody et al. (Cody et al. Int. Surg. Res., 52, 315 (1992)). Bactericidal activity can be evaluated against a variety of bacteria, preferably Gram-negative bacteria, but the types of bacteria can include *Pseudomonas* spp including *P. aeruginosa* and *P. cepacia*, *E. coli* strains, including *E. coli* B, *Salmonella*, *Proteus mirabilis* and *Staphylococcus* strains such as *Staphylococcus aureus*. Calixarene-based peptide mimetics with endotoxin neutralizing activity can be used to treat mammals infected with Gram-negative bacteria systemically and that exhibit symptoms of endotoxin shock such as fever, shock, and TNF-α release.

Endotoxin neutralizing activity can be measured by determining the molar concentration at which the peptide completely inhibits the action of lipopolysaccharide in an assay such as the *Limulus* amoebocyte lysate assay (LAL, Sigma Chemicals, St. Louis, Mo.) or the chromogenic LAL 1000 test (Biowhittacker, Walkersville, Md.). Endotoxin neutralizing activity can also be measured by calculating an inhibitory dose 50 ($LD_{50}$) using standard dose response methods. An inhibitory dose 50 is that amount of peptide that can inhibit 50% of the activity of endotoxin.

The present invention also provides a method for inhibiting the amount of TNF-α in a patient (e.g., a mammal such as a human). This involves administering to a patient an amount of a composition effective to inhibit the amount of TNF-α in a patient's system as determined by evaluating serum levels of TNF-α, wherein the composition includes one or more calixarene-based peptide mimetics described herein. Analogously, the present invention provides a method for inhibiting the amount of TNF-α in vitro (e.g., in a cell culture). This method involves incubating cells with an amount of a composition effective to decrease TNF-α amounts in the cell culture, wherein the composition includes one or more calixarene-based peptide mimetics described herein. For both in vivo and in vitro methods, the WEHI assay can be used for the detection of TNF-α (Battafarano et al., Surgery, 118, 318-324 (1995)) in cell culture or in serum from a patient. Alternatively, the amount of TNF-α in a sample can be assayed using an anti-TNF-α antibody. A calixarene-based peptide mimetic "active" for decreasing TNF-α can be evaluated using an in vitro test, and preferably shows an at least 10% decrease in the amount of TNF-α.

EXAMPLES

The invention will be further described by reference to the following detailed examples. These examples are offered to further illustrate the various specific and preferred embodiments and techniques. It should be understood, however, that many variations and modifications may be made while remaining within the scope of the present invention.

All reagents were obtained from Sigma-Aldrich Co. or Acros Organics except for N,N-dimethylethylenediamine, which was obtained from Lancaster Synthesis, Inc.

Examples 1-35

Preparation of Compounds

Exemplary calixarene derivatives can be made according to the following schemes and examples.

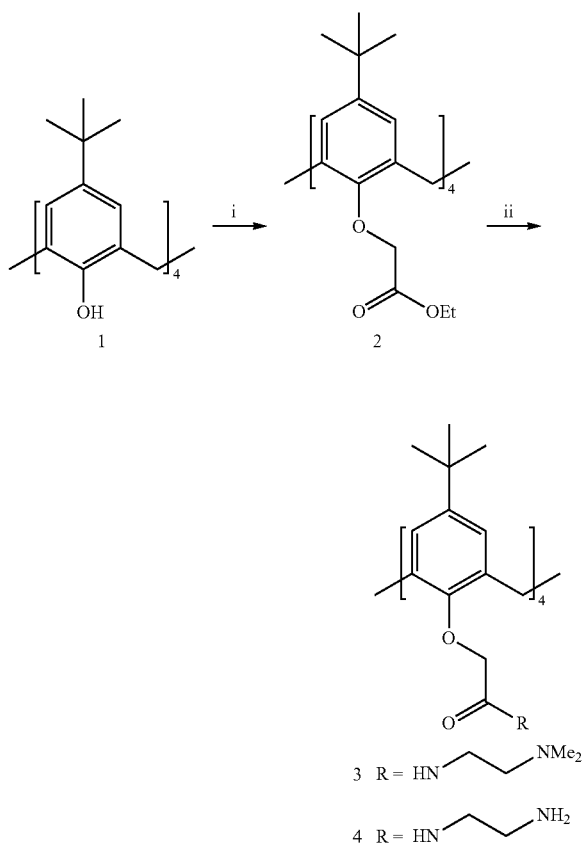

Scheme 1 i. ethyl bromoacetate, $K_2CO_3$, acetone, refluxed; ii. for 3, N,N-dimethylethylenediamine, toluene, refluxed; for 4, a) N-Boc ethylenediamine, toluene, refluxed; b) TFA, 5% anisole in $CH_2Cl_2$.

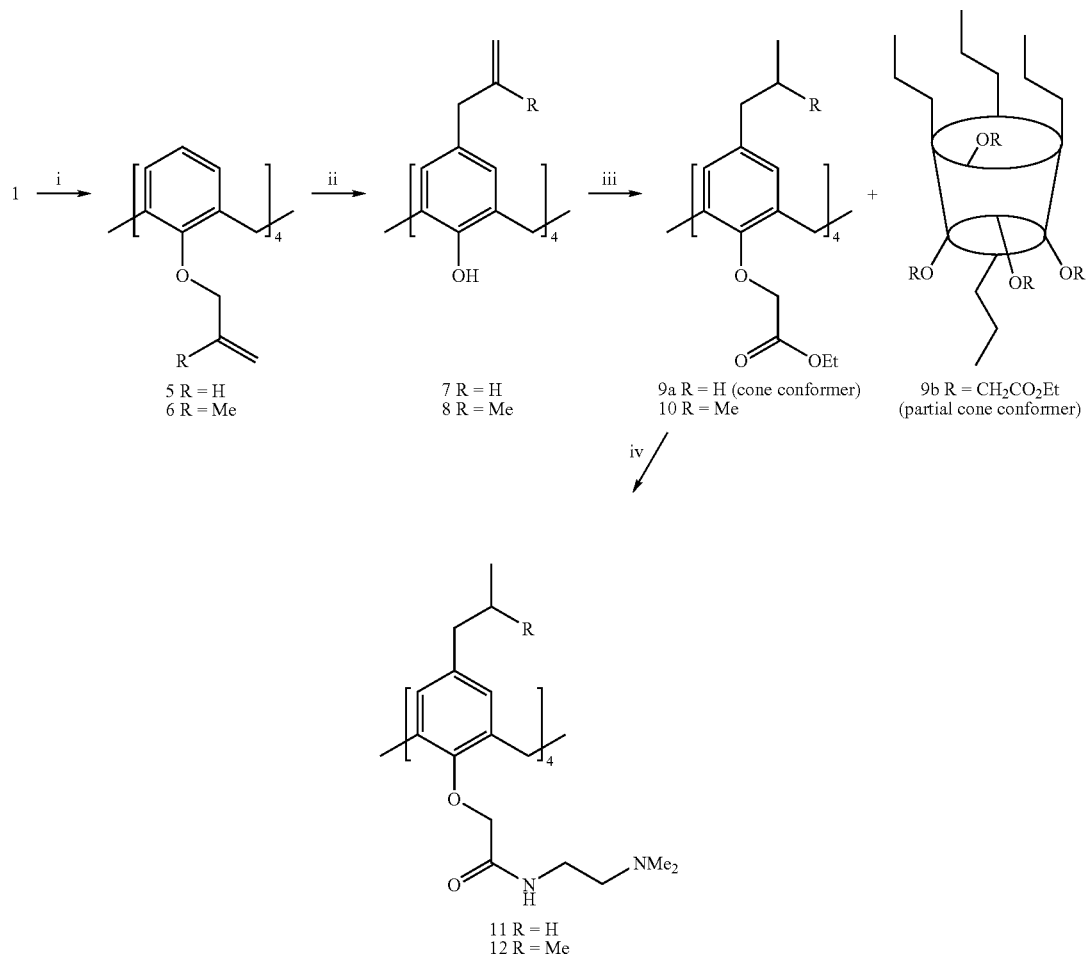
i. a) AlCl₃, PhOH, toluene, rt; b) for 5, NaH, allyl bromide, THF, DMF; for 6, NaH, methylallylchloride, THF, DMF; ii. N,N-dimethylaniline, 200° C.; iii. a) ethyl bromoacetate, K₂CO₃, acetone, refluxed; b) Pd/C, H₂, EtOAc; iv. for 11, AlMe₃, N,N-dimethyl-ethylenediamine, CH₂Cl₂, 40° C.; for 12, N,N-dimethyl-ethylenediamine, toluene, refluxed.
-continued
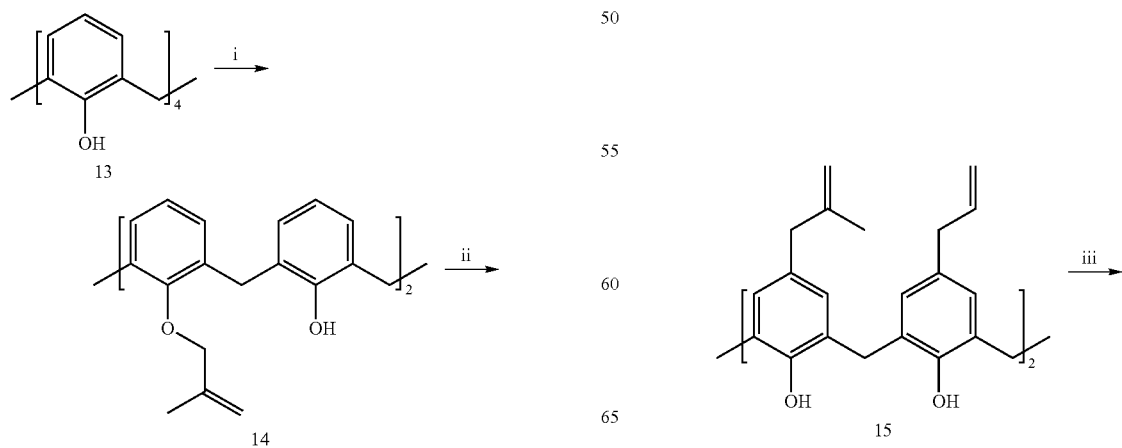

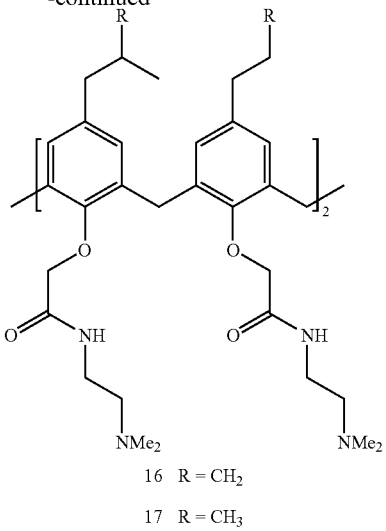

16 R = CH$_2$
17 R = CH$_3$ i. methylallylchloride, NaI, K$_2$CO$_3$, acetone, refluxed; ii. a) NaH, allylbromide, THF, DMF; b) bis-(trimethylsilyl)-urea, N,N-dimethylanaline, 200° C.; c) 3 N HCl; iii. a) ethyl bromoacetate, K$_2$CO$_3$, acetone, refluxed; b) for 16, N,N-dimethylethylenediamine, toluene, refluxed; for 17. i) Pd/C, H$_2$, EtOAC; ii) N,N-dimethylethylenediamine, toluene.

Scheme 5

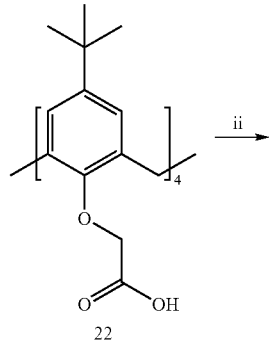

22

Scheme 4

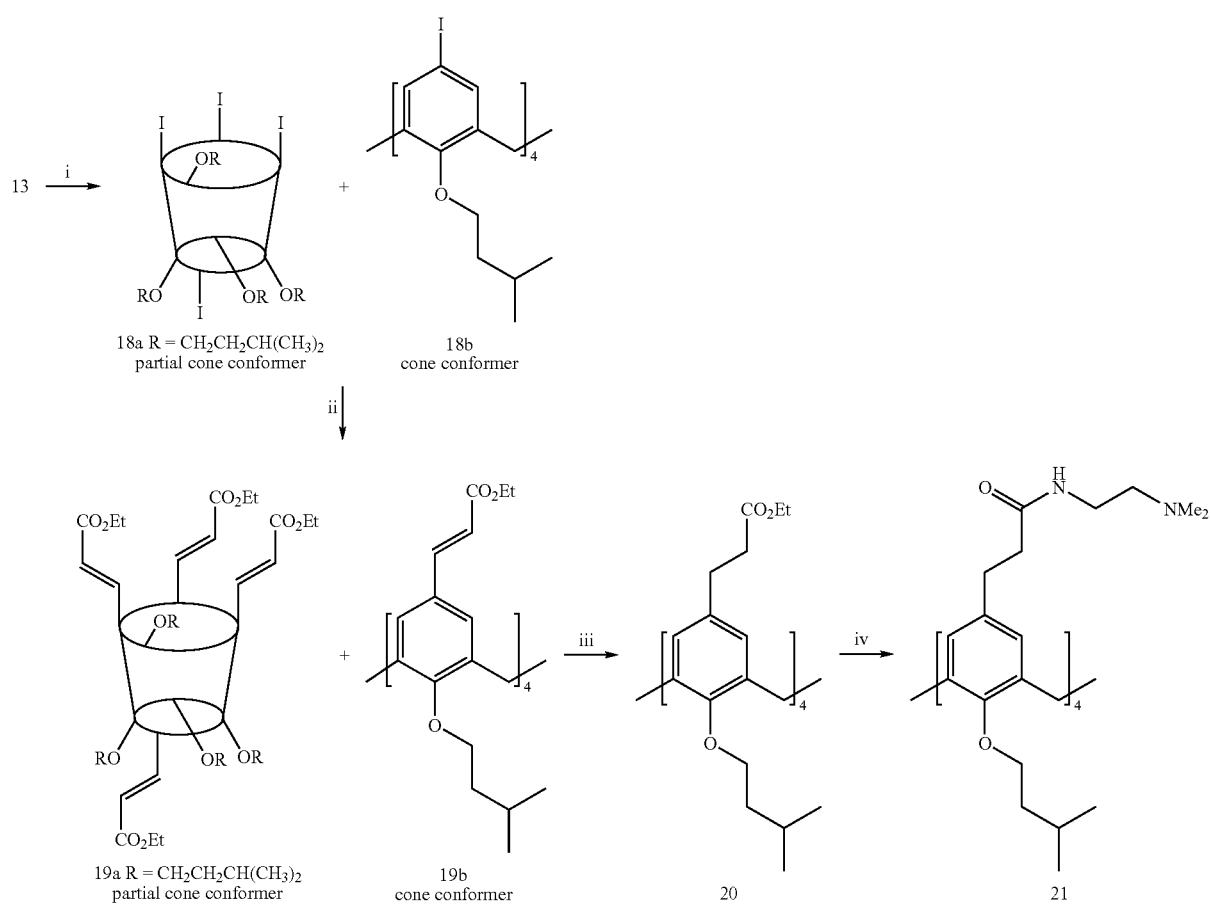

18a R = CH$_2$CH$_2$CH(CH$_3$)$_2$
partial cone conformer 18b
cone conformer

19a R = CH$_2$CH$_2$CH(CH$_3$)$_2$
partial cone conformer 19b
cone conformer

20

21 i. a) t-bromo-3-methylbutane, NaH, THF, DMF, refluxed; b) AgCO$_2$CF$_3$, I$_2$, CHCl$_3$, refluxed; ii. ethyl acrylate, Pd(OAc)$_2$, tri(O-toluene)phosphine, Et$_3$N, DMF, 80° C.; iii. Pd/C, HCO$_2$NH$_4$, EtOH, THF, 60° C.; iv. N,N-dimethylethylenediamine, 140° C., sealed tube.

39
-continued
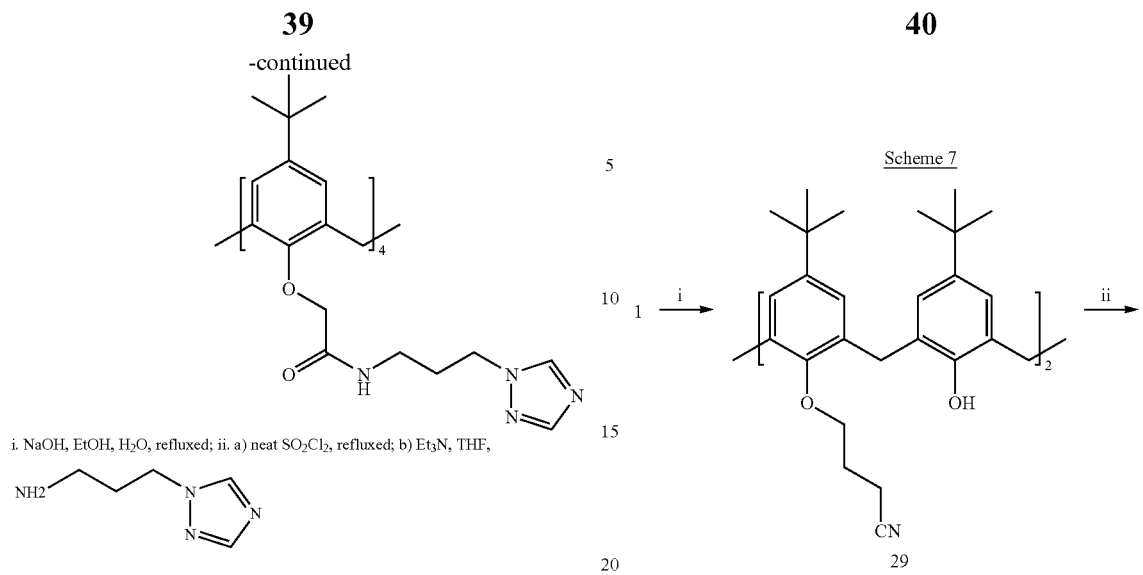
i. NaOH, EtOH, H₂O, refluxed; ii. a) neat SO₂Cl₂, refluxed; b) Et₃N, THF,
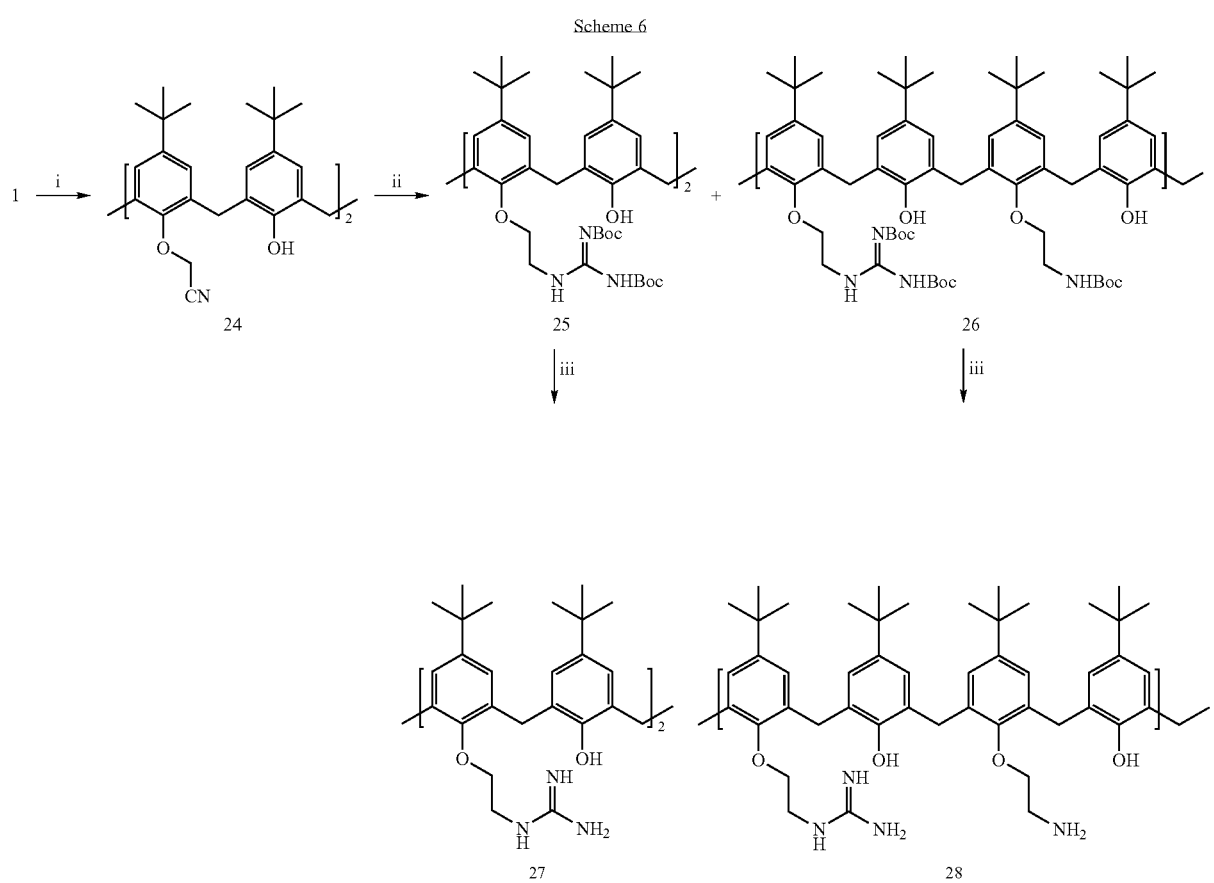
i. chloroacetonitrile, NaI, K₂CO₃, acetone, refluxed; ii. a) LiAlH₄, Et₂O,THF; b) 1,3-Bis(tert-butoxycarbonyl)-2-methyl-2-thiopseudourea, HgCl₂, Et₃N, CH₂Cl₂; iii. TFA, 5% anisole in CH₂Cl₂

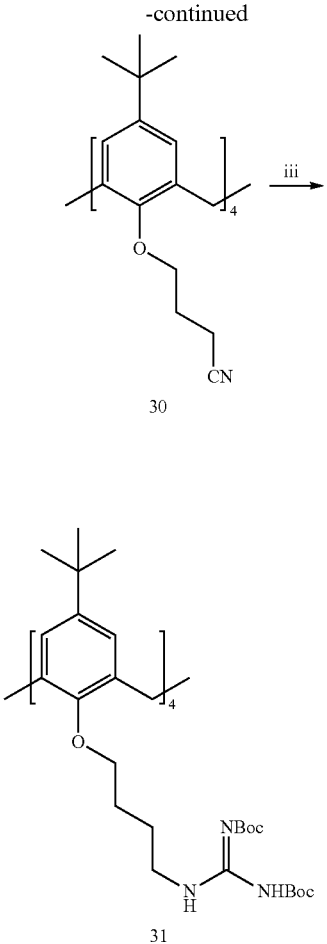
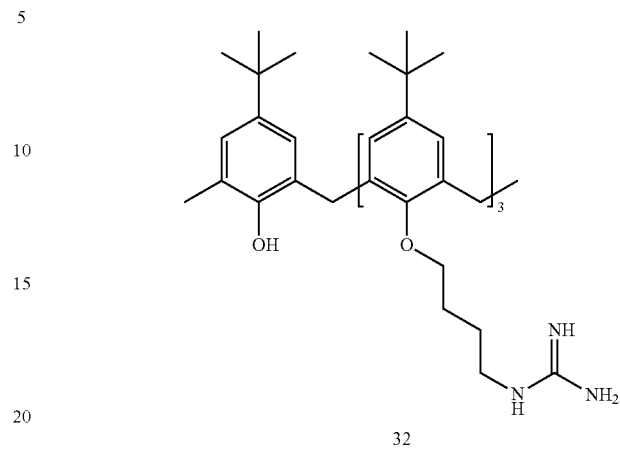
i. 4-bromo-butyronitrile, K₂CO₃, Acetone; ii. 4-romo-butyronitrile, NaH, DMF; iii. a) NaBH₄, CoCl₂, MeOH; b) 1,3-Bis(tert-butoxycarbonyl)-2-methyl-2-thiopseudourea, HgCl₂, Et₃N, CH₂Cl₂; iv. TFA, 5% anisole in CH₂Cl₂.
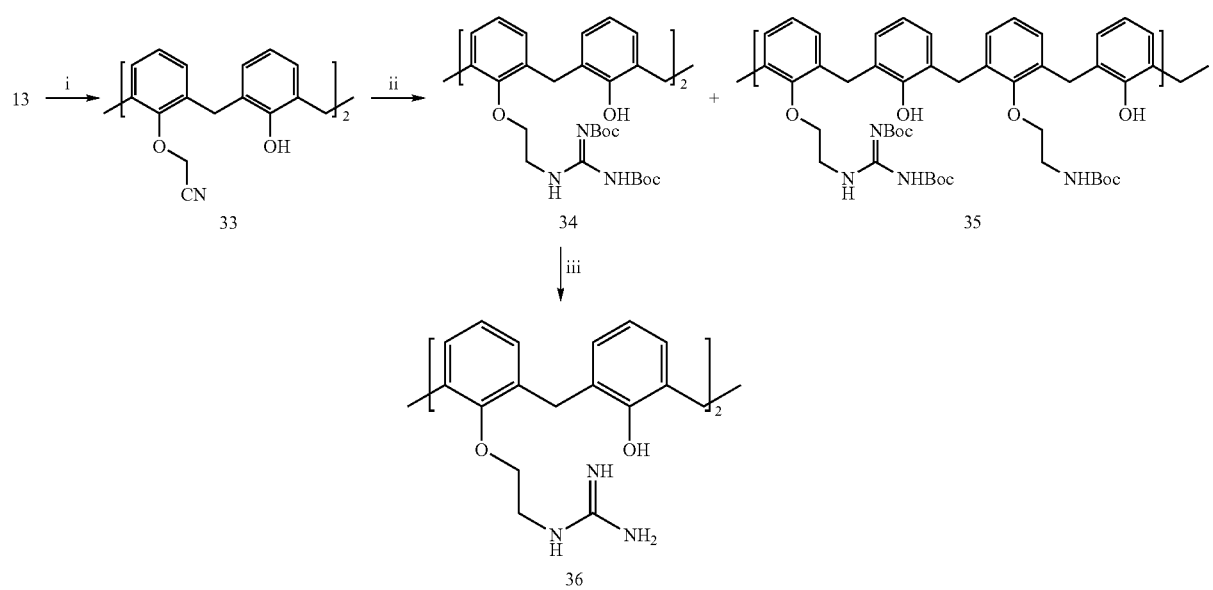
i. chloroacetonitrile, NaI, K₂CO₃, acetone, refluxed; ii. a) LiAlH₄, Et₂O, THF; b) 1,3- Bis(tert-butoxycarbonyl)-2-methyl-2-thiopseudourea, HgCl₂, Et₃N, CH₂Cl₂; iii. TFA. 5% anisole in CH₂Cl₂

Scheme 9

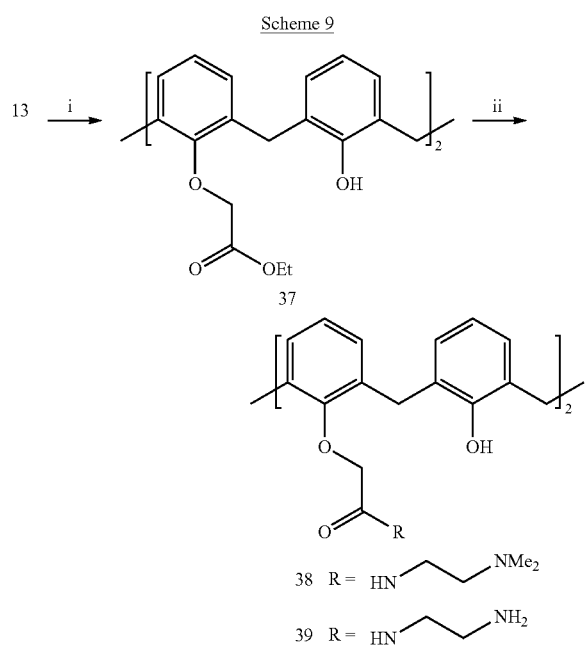

i. ethyl bromoacetate, K$_2$CO$_3$, acetone, refluxed; ii. for 40,
N,N-dimethylethylenediamine, toluene, refluxed; for 41, a) N-Boc ethylenediamine,
toluene, refluxed; b)TFA, 5% anisole in CH$_2$Cl$_2$.

Example 1

Tetra-ester 2,4-t-Butylcalix[4]arene 1 (3.2 g, 5.0 mmol) and K$_2$CO$_3$ (4.1 g, 30 mmol) were refluxed in acetone for one hour and then ethyl bromoacetate (4.4 mL, 40 mmol) was added. This reaction mixture was refluxed for 24 hours. After cooling, the reaction mixture was filtered through a pad of Celite and rinsed with CH$_2$Cl$_2$. The filtrate was concentrated under vacuo to give a yellow oil. The tetra-ester 2 (4.0 g, 81%) was obtained as white needle-like crystal by crystallization from a solution of CH$_2$Cl$_2$ and ethanol (~1:4). $^1$H NMR (300 MHz, CDCl$_3$) δ 6.78 (s, 8H), 4.86 (d, J=12.6 Hz, 4H), 4.80 (s, 8H), 4.21 (q, J=7.3 Hz, 8H), 3.19 (d, J=12.6 Hz, 4H), 1.29 (t, J=7.3 Hz, 12H), 1.07 (s, 36H).

Example 2

Tetra-amine 3. Tetra-ester-2 (198.6 mg, 0.2 mmol) and N,N-dimethylethylenediamine (0.88 mL, 40 mmol) were dissolved in toluene (0.2 mL) and the reaction was monitored by ESI. After being stirred at room temperature for 36 hours, volatile components were removed under vacuo. The residue was triturated in ether to give tetra-amine 3 (196.6 mg, 85%) as white solid. $^1$H NMR (500 MHz, CDCl$_3$) δ 7.67 (br t, J=6.0 Hz, 4H), 6.77 (s, 8H), 4.52 (s, 8H), 4.49 (d, J=13.0 Hz, 4H), 3.45 (br dt, J=6.5, 6.0 Hz, 8H), 3.23 (d, J=13.0 Hz, 4H), 2.47 (t, J=6.5 Hz, 8H), 2.23 (s, 24H), 1.07 (s, 36H); $^{13}$C NMR (125 MHz) δ 170.0 (4C), 153.2 (4C), 145.8 (4C), 132.9 (8C), 125.9 (8C), 74.8 (4C), 67.6 (4C), 58.3 (4C), 45.5 (8C), 37.3 (4C), 34.1 (4C), 31.5 (12C); HRMS (ESI) m/z calcd for C$_{68}$H$_{105}$N$_8$Na$_1$O$_8$ (M+H+Na)$^{2+}$ 592.3977. found 592.3992.

Example 3

Tetra-amine 4. Tetra-ester 2 (49.7 mg, 0.05 mmol) and N-Boc ethylenediamine (A. Eisenfuhr et al., *Bioorg. Med. Chem.* 2003, 11, 235-249) (320.2 mg, 2.0 mmol) was dissolved in toluene (0.4 mL). The light yellow clean solution was heated at 80° C. After two hours the reaction mixture turned cloudy. After 18 hours the reaction was complete as indicated by ESI. The reaction mixture was cooled and partitioned between CH$_2$Cl$_2$ and water. The organic phase was combined, dried (Na$_2$SO$_4$), and concentrated. The residue was dissolved in a minimum amount of CH$_2$Cl$_2$ and precipitated by ether to give the Boc-protected tetra-amine as a white solid.

This solid was dissolved in a solution of CH$_2$Cl$_2$ with 40% TFA and 5% anisole and the mixture was stirred at room temperature for 15 hours. The volatile components were removed under vacuo and the residue was triturated in ether to give the tetra-amine 4•TFA salt (52.5 mg, 70%) as a white solid. $^1$H NMR (300 MHz, CD$_3$OD, 55° C.) δ 6.95 (br s, 8H), 4.59 (s, 8H), 4.50 (d, J=12.9 Hz, 4H), 3.64 (t, J=5.9 Hz, 8H), 3.33 (d, J=12.9 Hz, 4H), 3.19 (t, J=6.0 Hz, 8H), 1.13 (s, 36H); HRMS (ESI) m/z calcd for C$_{60}$H$_{90}$N$_8$O$_8$ (M+2H)$^{2+}$ 525.3441. found 525.3446.

Example 4

O-Allyl calix[4]arene 5. To a suspension of t-butyl calix[4]arene 1 (3.2 g, 5.0 mmol) in toluene (30.0 mL) was added AlCl$_3$ (5.2 g, 40 mmol) and phenol (3.8 g, 40 mmol). The reaction mixture was stirred at room temperature for 4 hours and then 0.2 N HCl (50.0 mL) was added. After 5 min the reaction mixture was extracted by CH$_2$Cl$_2$, and the combined organic phase was concentrated. Methanol (50.0 mL) was added to the residues to create a slurry, from which de-t-butylated calix[4]arene (2.0 g, 94%) was collected as a white solid.

To a solution of this tetraphenol (746 mg, 1.8 mmol) in THF (45.0 mL) and DMF (4.5 mL) was added NaH (697 mg, 29 mmol). The reaction mixture was refluxed for 1 hour and allyl bromide (7.6 ml, 88 mmol) was added. Continuously heated for 5 hours, the reaction mixture was cooled and filtered through a pad of Celite. The filtrate was diluted with EtOAc and washed with brine. Organic phase was separated, dried (Na$_2$SO$_4$) and concentrated. O-Allyl calix[4]arene 5 (703.2 mg) was obtained by crystallization from ethanol as white needle-like crystals. After the mother liquor was further purified by flash chromatography (1% EtOAc in hexanes), more calix[4]arene 5 (277.9 mg) was collected to provide 95% total yield. The $^1$H NMR spectrum showed the sample to be a mixture of more than two (cone and partial cone) rotamers (C D Gutsche et al., *Tetrahedron* 1983, 39, 409). $^1$H NMR (300 MHz, CD$_3$Cl) δ 7.29-6.43 (m, 12H, ArH), 6.38-5.80 (m, 4H, C=CH—C), 5.44-4.74 (m, 8H, CH$_2$=C), 4.47-3.87 (m, 8H, OCH$_2$), 4.43-3.68 (many ds, J≈13 Hz, 4H, ArCH$_2$Ar), 3.62-3.05 (many ds, J≈13 Hz, 4H, ArCH$_2$Ar).

Example 5

O-Methallyl calix[4]arene 6. According to the procedure described for calix[4]arene 5, calix[4]arene (212.2 mg, 0.5 mmol) in THF (5.0 mL) and DMF (0.5 mL) was treated with NaH (200.0 mg, 8.2 mmol) and methylallylchloride (2.2 mL, 25 mmol). Standard workup and purification with flash chromatography (1% EtOAc in hexanes) gave O-methylallyl calix[4]arene 6 (320.3 mg, 100%) as colorless oil. $^1$H NMR (500 MHz. CD$_3$Cl) δ 7.30-6.21 (m, 12H, ArH), 5.24-4.68 (m, 8H, CH$_2$=C), 4.49-3.66 (many ds, J≈13 Hz, 4H, ArCH$_2$Ar), 4.41-4.03 (m, 8H, OCH$_2$), 3.61-3.07 (many ds, J≈13 Hz, 4H, ArCH$_2$Ar), 1.92-1.53 (m, 12H, C=CCH$_3$—C).

Example 6

4-Allyl calix[4]arene 7. O-Allyl calix[4]arene 5 (338.8 mg, 0.58 mmol) was dissolved in neat N,N-dimethylaniline (6 mL) and stirred at 210° C. for 2 hours. The reaction mixture was cooled and poured into ice-water (50.0 mL) with concentrated HCl (50.0 mL). The mixture was stirred for 10 min and extracted by $CHCl_3$. The organic phase was separated, dried ($Na_2SO_4$), and concentrated. Crystallization from ethanol provided 4-allyl calix[4]arene 7 (271.0 mg) as white fine crystals. The mother liquor was concentrated and crystallized to give more desired product (15.1 mg) to provide 84% total yield. $^1$H NMR (500 MHz, $CDCl_3$) δ 10.16 (s, 4H), 6.84 (s, 8H), 5.86 (ddt, J=17.0, 10.5, 6.8 Hz, 4H), 5.04 (br d, J=17.0 Hz, 4H), 5.03 (br d, J=10.5 Hz, 4H), 4.19 (br d, J=9.0 Hz, 4H), 3.45 (br d, J=9.0 Hz, 4H), 3.18 (d, J=6.8 Hz, 8H).

Example 7

4-methallyl calix[4]arene 8. According to the procedure described for 4-allyl calix[4]arene 7, O-methallyl calix[4]arene 6 (44.5 mg, 0.069 mmol) was subjected to Claisen rearrangement in neat N,N-dimethylaniline (1 mL). Standard workup and crystallization gave 4-methallyl calix[4]arene 8 (27.6 mg). Further purification of the mother liquor provided more desired product (2.4 mg) to provide 67% total yield. $^1$H NMR (500 MHz, $CDCl_3$) δ 10.19 (s, 4H), 6.88 (s, 8H), 4.77 (br s, 4H), 4.68 (br s, 4H), 4.21 (br d, J=12.5 Hz, 4H), 3.45 (br d, J=12.5 Hz, 4H), 3.10 (s, 8H), 1.63 (s, 12H); $^{13}$C NMR (125 MHz) δ 147.3 (4C), 145.4 (4C), 133.3 (8C), 129.5 (8C), 128.2 (4C), 112.0 (4C), 44.0 (4C), 32.0 (4C), 22.3 (4C); HRMS (ESI) m/z calcd for $C_{44}H_{48}Na_1O_4$ (M+Na)$^+$ 663.3450. found 663.3446.

Example 8

Tetra-ester 9a and 9b. According to the procedure described for tetra-ester 2,4-allyl calix[4]arene 7 (116.9 mg, 0.2 mmol) in acetone (4.0 mL) was treated with $K_2CO_3$ (221.1 mg, 1.6 mmol) and ethylbromoacetate (0.18 mL, 1.6 mmol). Standard workup gave the crude product as an oil, which was dissolved in EtOAc (4 mL). After addition of Pd on activated carbon (10%, 95.6 mg), the reaction mixture was stirred under one atmosphere of $H_2$ for 2 hour and then filtered through a pad of Celite. The filtrate was concentrated and crystallization from a solution of $CH_2Cl_2$ and methanol (~1:4) afforded tetra-ester 9a (111.9 mg) in the cone conformation as clear needle-like crystals. The mother liquor was further purified by MPLC (20% EtOAc in hexanes) to give more tetra-ester 9a (4.2 mg) and 9b (in partial cone conformation, 4.0 mg) to provide 62% total yield for cone rotamer and 2% yield for partial cone rotamer. Cone conformer 9a: $^1$H NMR (500 MHz, $CDCl_3$) δ6.48 (s, 8H), 4.80 (d, J=13.0 Hz, 4H), 4.73 (s, 8H), 4.20 (q, J=7.5 Hz, 8H), 3.13 (d, J=13.0 Hz, 4H), 2.24 (t, J=7.3 Hz, 8H), 1.40 (tq, J=7.3, 7.3 Hz, 8H), 1.28 (t, J=7.5 Hz, 12H), 0.81 (t, J=7.3 Hz, 12H); $^{13}$C NMR (125 MHz, $CDCl_3$) δ 170.6 (4C), 153.8 (4C), 136.8 (4C), 134.2 (8C), 128.6 (8C), 71.6 (4C), 60.6 (4C), 37.4 (4C), 31.7 (4C), 24.7 (4C), 14.4 (4C), 13.9 (4C); HRMS (ESI) m/z calcd for $C_{56}H_{72}Na_1O_{12}$ (M+Na)$^+$ 959.4921. found 959.4921. Partial cone conformer 9b: $^1$H NMR (500 MHz, $CDCl_3$) δ 7.23 (s, 2H), 6.83$^+$ (d, J≈2, 2H), 6.83$^-$ (s, 2H), 6.12 (d, J=2.1 Hz, 2H), 4.40 (d, J=14.0 Hz, 2H), 4.38 (s, 4H), 4.31-4.24 (m, 6H), 4.21 (s, 2H), 4.07 (s, 2H), 4.01 (q, J=7.0 Hz, 2H), 3.80 (d, J=13.4 Hz, 2H), 3.69 (d, J=13.4 Hz, 2H), 3.08 (d, J=14.0 Hz, 2H), 2.61 (t, J=7.8 Hz, 2H), 2.54 (t, J=7.3 Hz, 2H), 2.22 (ddd, J=14.0, 9.1, 7.2 Hz, 2H), 2.12 (ddd, J=14.0, 8.8, 6.9 Hz, 2H), 1.70 (tq, J=7.8, 7.4, 2H), 1.65 (tq, J=7.4, 7.3 Hz, 2H), 1.37-1.30 (m, 4H), 1.35 (t, J=7.0 Hz, 3H), 1.33 (t, J=6.7 Hz, 3H), 1.18 (t J=7.3 Hz, 3H), 1.01 (t, J=7.4 Hz, 3H), 0.94 (t, J=7.4 Hz, 3H), 0.82 (t, J=7.4 Hz, 6H).

Example 9

Tetra-ester 10. According to the procedure described for tetra-ester 2,4-methallyl calix[4]arene 8 (96.1 mg, 0.15 mmol) in acetone (3.0 mL) was treated with $K_2CO_3$ (165.8 mg, 1.2 mmol) and ethyl bromoacetate (0.13 mL, 1.2 mmol). Standard workup gave the crude product, which was subjected to hydrogenation with Pd on activated carbon (10%, 70 mg) in EtOAc (3 mL). Purification of the crude reduced product with flash chromatography (15% EtOAc in hexanes) provided oil-like tetra-ester 10 (148.0 mg, 100%) in the cone conformation. $^1$H NMR (500 MHz, $CDCl_3$) δ 6.47 (s, 8H), 4.80 (d, J=13.2 Hz, 4H), 4.75 (s, 8H), 4.20 (q, J=7.4 Hz, 8H), 3.14 (d, J=13.2 Hz, 4H), 2.11 (d, J=7.4 Hz, 8H), 1.59 (m, 4H), 1.28 (t, J=7.4 Hz, 12H), 0.75 (d, J=6.1 Hz, 24H); $^{13}$C NMR (75 MHz, $CDCl_3$) δ 170.7 (4C), 153.7 (4C), 135.8 (4C), 134.0 (8C), 129.4 (8C), 71.5 (4C), 60.5 (4C), 44.9 (4C), 31.6 (4C), 30.4 (4C), 22.4 (8C), 14.4 (4C); HRMS (ESI) m/z calcd for $C_{60}H_{80}Na_1O_{12}$ (M+Na)$^+$ 1015.5547. found 1015.5575.

Example 10

Tetra-amine 11a. N,N-Dimethylethylenediamine (0.22 mL, 2.0 mmol) in $CH_2Cl_2$ (0.5 mL) was treated with $AlMe_3$ (2.0 M in toluene, 1.0 mL) at 0° C. The reaction mixture was allowed to warm to room temperature and stirred for 15 min. Tetra-ester 9 (93.1 mg, 0.1 mmol) in $CH_2Cl_2$ (1.0 mL) was added through cannula, and the mixture was heated to 40° C. and stirred for overnight. The reaction was carefully quenched with 1N HCl. After the aqueous layer was adjusted to pH=8 by sat. $NaHCO_3$ aq, the mixture was extracted with $CHCl_3$. The combined organic phase was washed with brine, dried ($Na_2SO_4$), and concentrated to provide tetra-amine 11a as a light yellow foam solid (98.9 mg, 90%). $^1$H NMR (500 MHz, $CDCl_3$) δ 7.58 (br t, J=6.4 Hz, 4H), 6.42 (s, 8H), 4.46 (s, 8H), 4.41 (d, J=13.8 Hz, 4H), 3.42 (dt, J=6.9, 6.4 Hz, 8H), 3.15 (d, J=13.8 Hz, 4H), 2.44 (t, J=6.9 Hz, 8H), 2.24 (t, J=7.4 Hz, 8H), 2.20 (s, 24H), 1.44 (app sextet, J=7 Hz, 8H), 0.84 (t, J=7.2 Hz, 12H); $^{13}$C NMR (125 MHz, $CDCl_3$) δ 169.8 (4C), 153.8 (4C), 137.0 (4C), 133.6 (8C), 128.8 (8C), 74.4 (4C), 58.2 (4C), 45.5 (8C), 37.4 (4C), 37.2 (4C), 31.3 (4C), 24.6 (4C), 13.8 (4C); HRMS (ESI) m/z calcd for $C_{64}H_{97}N_8O_8$ (M+H)$^+$ 1105.7429. found 1105.7471.

Example 11

Tetra-amine 12. Tetra-ester 10 (146.8 mg, 0.15 mmol) in toluene (1.5 mL) and methanol (1.5 mL) was treated with N,N-dimethylethylenediamine (0.32 mL, 2.96 mmol) and stirred in a sealed tube at 80° C. for 24 hours. The volatile components were removed under vacuo (~60° C. bath temperature) to give a light brown sticky solid. The solid was dissolved in a minimum amount of $CH_2Cl_2$ and tera-amine 12 (103.6 mg, 60%) was obtained as a light yellow solid by the sequence of dropwise addition of ether (~10:1 $Et_2O$:$CH_2CF_2$ final ratio), centrifugation, decantation, and drying. $^1$H NMR (500 MHz, $CDCl_3$) δ 7.74 (br t, J=5.8 Hz, 4H), 6.39 (s, 8H), 4.48 (s, 8H), 4.44 (d, J=13.5 Hz, 4H), 3.46 (dt, J=6.2, 5.8 Hz, 8H), 3.16 (d, J=13.5 Hz, 4H), 2.50 (t, J=6.2 Hz, 8H), 2.25 (s, 24H), 2.10 (d, J=7.0 Hz, 8H), 1.65 (m, 4H), 0.80 (d, J=6.2 Hz, 24H); $^{13}$C NMR (125 MHz, $CDCl_3$) δ 170.0 (4C), 153.8 (4C), 136.2 (4C), 133.4 (8C), 129.7 (8C), 74.5 (4C), 58.2 (4C), 45.4 (8C), 45.0 (4C), 37.1 (4C), 31.3 (4C), 30.5 (4C), 22.4 (8C); HRMS (ESI) m/z calcd for $C_{68}H_{105}N_8O_8$ (M+H)$^+$ 1161.8055. found 1161.8091.

Example 12

25,27-Di-(2-methallyloxy)-26,28-dihydroxycalix[4]arene 14. To the suspension of calix[4]arene (42.4 mg, 0.1 mmol) in acetone (5 mL) was added $K_2CO_3$ (221.1 mg, 1.6 mmol) and the mixture was refluxed for 1 hour. After cooling, NaI (749.4 mg, 5.0 mmol) and 2-methyl-allylchloride (0.49 mL, 5.0 mmol) was added to the reaction mixture, which was then refluxed for overnight. The reaction mixture was filtered through a pad of Celite and rinsed with $CH_2Cl_2$. The combined filtrate was washed with brine, dried ($Na_2SO_4$), and concentrated. Crystallization of the residue from a solution of $CH_2Cl_2$ and ethanol (~1:4) gave 25,27-dimethallyloxy-26,28-dihydroxycalix[4]arene 14 as yellow needle crystal (40 mg, 75%). $^1$H NMR (500 MHz, $CDCl_3$) δ 8.03 (s, 2H), 7.06 (d, J=7.2 Hz, 4H), 6.90 (d, J=7.0 Hz, 4H), 6.74 (t, J=7.2 Hz, 2H), 6.65 (t, J=7.0 Hz, 2H), 5.46 (s, 2H), 5.12 (s, 2H), 4.38 (s, 4H), 4.32 (d, J=13.3 Hz, 4H), 3.38 (d, J=13.3 Hz, 4H), 2.07 (s, 6H); $^{13}$C NMR (75 MHz, $CDCl_3$) δ 153.6 (2C), 151.9 (2C), 140.9 (2C), 133.5 (2C), 129.2 (4C), 128.7 (4C), 128.1 (4C), 125.6 (4C), 119.1 (2C), 113.6 (2C), 80.4 (2C), 31.5 (4C), 20.1 (2C); HRMS (ESI) m/z calcd for $C_{36}H_{36}Na_1O_4$ (M+Na)$^+$ 555.2511. found 555.2520.

Example 13

5,17-Di-(2-methallyl)-11,23-diallylcalix[4]arene 15. According to the procedure described for calix[4]arene 5, calix[4]arene 14 (35.7 mg, 0.07 mmol) in THF (1.0 mL) and DMF (0.1 mL) was treated with NaH (26.5 mg, 1.1 mmol) and allylbromide (0.3 mL, 3.3 mmol). Standard workup and purification with flash chromatography (1% EtOAc in hexanes) gave 25,27-dimethallyloxy-26,28-diallyloxycalix[4]arene (40.1 mg, 98%) as colorless oil.

The above calix[4]arene derivative (122.6 mg, 0.2 mmol) and bis-(trimethylsilyl)-urea (327.1 mg, 1.6 mmol) in N,N-dimethylaniline (4 mL) was stirred at 210° C. for 4 hours. The reaction mixture was cooled and poured into ice-water (30.0 mL) with concentrated HCl (30.0 mL). The mixture was stirred for 10 min, extracted by $CHCl_3$, and concentrated. The resulting residue was dissolved in MeOH—$CH_2Cl_2$ (2 mL, 1:1). After addition of 3 N HCl (0.7 mL), the reaction mixture was stirred at room temperature for 10 hours. After removal of the volatile components, 5,17-Di-(2-methallyl)-11,23-diallylcalix[4]arene 15 (82.5 mg, 67%) was obtained as off-white solid by treating the concentrated residue with MeOH. $^1$H NMR (500 MHz, $CDCl_3$) δ 10.2 (s, 4H), 6.84 (s, 4H), 6.83 (s, 4H), 5.85 (ddt, J=17.1, 10.5, 6.9 Hz, 2H), 5.03 (br d, J=17.1 Hz, 2H), 5.02 (br d, J=10.5 Hz, 2H), 4.77 (s, 2H), 4.69 (s, 2H), 4.21 (br d, J=12.7 Hz, 4H), 3.45 (br d, J=12.7 Hz, 4H), 3.17 (d, J=6.9 Hz, 4H), 3.11 (s, 4H), 1.64 (s, 6H); $^{13}$C NMR (75 MHz, $CDCl_3$) δ 147.3 (2C), 147.2 (2C), 145.4 (2C), 137.8 (2C), 133.7 (2C), 133.3 (2C), 129.5 (4C), 129.2 (4C), 128.4 (4C), 128.2 (4C), 115.8 (2C), 112.0 (2C), 43.9 (2C), 39.6 (2C), 32.0 (4C), 22.3 (2C); HRMS (ESI) m/z calcd for $C_{42}H_{44}Na_1O_4$ (M+H)$^+$ 635.3137. found 635.3145.

Example 14

5,17-Di-(2-methallyl)-11,23-diallyl-25,26,27,28-tetrakis-N—(N,N-dimethyl-2-aminoethyl)carbamoylmethoxy calix[4]arene 16. According to the procedure described for tetraester 2, calix[4]arene 15 (61.3 mg, 0.1 mmol) in acetone (2.0 mL) was treated with $K_2CO_3$ (110.5 mg, 0.8 mmol) and ethyl bromoacetate (0.09 mL, 0.8 mmol). Standard workup and chromatography (20% EtOAc in hexanes) gave the desired tetraester (66.4 mg, 69%) as an oil.

The above tetraester (30.7 mg, 0.03 mmol) in MeOH (0.3 mL) and toluene (0.3 mL) was treated with N,N-dimethylethylenediamine (0.14 mL, 1.28 mmol) and stirred in a sealed tube at 80° C. for 48 hours. After removal of volatile components, the residue was triturated with ether to give tetraamine 16 (24.5 mg, 73%) as a pale yellow solid. $^1$H NMR (500 MHz, $CDCl_3$) δ 7.94 (br t, J=6.5 Hz, 2H), 7.33 (br t, J=6.5 Hz, 2H), 6.73 (s, 4H), 6.17 (s, 4H), 5.65 (ddt, J=17.1, 10.5, 6.8 Hz, 2H), 4.91 (dd, J=10.5, 1.4 Hz, 2H), 4.85 (dd, J=17.1, 1.4 Hz, 2H), 4.80 (s, 2H), 4.65 (s, 2H), 4.61 (s, 4H), 4.45 (d, J=13.5 Hz, 4H), 4.33 (s, 4H), 3.50 (dt, J≈6, 6 Hz, 4H), 3.37 (dt, J≈6, 6 Hz, 4H), 3.17 (d, J=14.7 Hz, 4H), 3.16 (s, 4H), 2.86 (d, J=6.8 Hz, 4H), 2.52 (t, J=6.4 Hz, 4H), 2.40 (t, J=6.4 Hz, 4H), 2.24 (s, 12H), 2.19 (s, 12H), 1.68 (s, 6H); $^{13}$C NMR (125 MHz, $CDCl_3$) δ 170.2 (2C), 169.5 (2C), 154.9 (2C), 153.4 (2C), 145.9 (2C), 137.8 (2C), 134.9 (4C), 134.4 (2C), 134.3 (2C), 132.9 (4C), 130.1 (4C), 128.5 (4C), 115.4 (2C), 111.6 (2C), 74.7 (2C), 74.2 (2C), 58.3 (2C), 58.1 (2C), 45.5 (4C), 45.4 (4C), 44.1 (2C), 39.6 (2C), 37.1 (2C), 37.1 (2C), 31.3 (4C), 22.3 (2C); HRMS (ESI) m/z calcd for $C_{66}H_{93}N_8O_8$ (M+H)$^+$ 1125.7116. found 1125.7213.

Example 15

5,17-Di-(2-methylpropyl)-11,23-dipropyl-25,26,27,28-tetrakis-N—(N,N-dimethyl-2-aminoethyl)carbamoylmethoxy calix[4]arene 17. The tetraester (35.1 mg, 0.04) described in the procedure for calix[4]arene 16 was dissolved in EtOAc (1 mL) and treated with Pd on activated carbon (10%, 20 mg) at one atmosphere of $H_2$. After 2 hours, the reaction mixture was filtered through a pad of Celite and rinsed with $CH_2Cl_2$. The combined filtrate was concentrated and purified by MPLC (15% EtOAc in hexanes) to give saturated tetraester (32.6 mg, 91%) as a colorless oil.

The above saturated tetraester (32.6 mg, 0.03 mmol) was stirred in neat N,N-dimethylethylenediamine (0.15 mL, 1.37 mmol) at room temperature for 24 hours. After being concentrated, the residue was triturated with ether to give tetraamine 17 (21.4 mg, 56%) as a pale yellow solid. $^1$H NMR (500 MHz, $CDCl_3$) δ 7.87 (t, J=6.0 Hz, 2H), 7.36 (t, J=5.9 Hz, 2H), 6.63 (s, 4H), 6.20 (s, 4H), 4.58 (s, 4H), 4.43 (d, J=13.9 Hz, 4H), 4.36 (s, 4H), 3.48 (td, J≈7, 6 Hz, 4H), 3.38 (td, J≈6, 6 Hz, 4H), 3.15 (d, J=13.9 Hz, 4H), 2.49 (t, J=6.6 Hz, 4H), 2.39 (t, J=6.2 Hz, 4H), 2.28 (d, J=2.7 Hz, 4H), 2.23 (s, 12H), 2.18 (s, 12H), 2.06 (t, J=7.0 Hz, 4H), 1.78 (m, 2H), 1.30 (tq, J=7.5, 7.0 Hz, 4H), 0.87 (d, J=6.8 Hz, 12H), 0.78 (t, J=7.5 Hz, 6H); $^{13}$C NMR (125 MHz, $CDCl_3$) δ 70.3 (2C), 169.7 (2C), 154.4 (2C), 153.1 (2C), 137.1 (2C), 136.2 (2C), 134.4 (4C), 132.7 (4C), 130.1 (4C), 128.4 (4C), 74.7 (2C), 74.2 (2C), 58.3 (2C), 58.1 (2C), 45.4 (4C), 45.4 (4C), 44.9 (2C), 37.4 (2C), 37.1 (2C), 37.1 (2C), 31.3 (4C), 30.7 (2C), 24.5 (2C), 22.4 (4C), 14.0 (2C): HRMS (ESI) m/z calcd for $C_{66}H_{101}N_8O_8$ (M+H)$^+$ 1133.7742. found 1133.7813.

Example 16

5,11,17,23-Tetraiodo-25,26,27,28-tetra(3-methylbutoxy) calix[4]arene (18a and 18b). Calix[4]arene 13 (424.5 mg, 1.0 mmol) in THF (25 mL) and DMF (2.5 mL) was treated with NaH (384.0 mg, 16.0 mmol). The reaction mixture was refluxed for 1 hour followed with addition of 1-bromo-3-methylbutane (6.0 mL, 50.0 mmol), and the reaction continued for additional 18 hours under reflux. After cooling, the reaction mixture was filtered through a pad of Celite, and the filtrate was washed with brine, dried ($Na_2SO_4$), and concentrated. The residue was purified with flash chromatography (2% EtOAc in hexanes) to give tetra-iso-amyloxycalix[4]arene (690.6 mg, 98%) as a colorless oil.

To the suspension of $Ag_2CO_3$ (711.4 mg, 2.6 mmol) and TFA (0.4 mL, 5.2 mmol) in $CHCl_3$ (40 mL, reagent grade, stabilizing ethanol not removed) was added the tetra-isoamyloxycalix[4]arene (672.2 mg, 0.9 mmol) and the reaction mixture was refluxed for 3 hours. After cooling, $I_2$ (3324.9 mg, 13.1 mmol) was added and the reaction mixture was refluxed for additional 18 hours. After cooling, AgI was removed by filtration through Celite and the violet filtrate was bleached by washing with 10% (w/v) sodium hydrogensulfite (50 mL). The organic extract was collected, dried ($Na_2SO_4$) and concentrated. 4-Iodo-3-methylbutoxycalix[4]arene 18a and 18b (881.9 mg, 77%) was collected as a pale pink solid after flash chromatography (2% EtOAc in hexanes). $^1$H NMR indicated that it is a mixture of cone conformer 18b and partial cone conformer 18a in a ratio of 1.8 to 1. For cone conformer 18b: $^1$H NMR (500 MHz, $CDCl_3$) δ 7.0 (s, 8H), 4.27 (d, J=13.0 Hz, 4H), 3.89 (br t, J=7.6 Hz, 8H), 3.06 (d, J=13.0 Hz, 4H), 1.7 (m, 12H), 0.94 (d, J=6.3 Hz, 24H); For partial cone conformer: $^1$H NMR (500 MHz, $CDCl_3$) δ 7.54 (s, 2H), 7.38 (s, 2H), 7.28 (d, J=2.2 Hz, 2H), 6.64 (d, J=2.2 Hz, 2H), 3.97 (d, J=13.4 Hz, 2H), 3.81 (t, J=6.7 Hz, 2H), 3.75 (m, 2H), 3.63-3.45 (m, 4H), 3.53 (d, J=13.0 Hz, 2H), 3.48 (d, J=13.0 Hz, 2H), 2.98 (d, J=13.4 Hz, 2H), 1.94 (nonet, 1H), 1.85 (td, J=6,6 Hz, 2H), 1.78-1.70 (m, 6H), 1.31-1.26 (m, 3H), 1.12 (d, J=6.9 Hz, 6H), 1.03 (d, J=6.6 Hz, 6H), 0.99 (d, J=6.1 Hz, 6H), 0.88 (d, J=6.3 Hz, 6H); HRMS (ESI) m/z, calcd for $C_{48}H_{60}Na_1O_4$ $(M+Na)^+$ 1231.0568. found 1231.0641.

Example 17

Unsaturated tetra-ester 19a and 19b. A sealable tube with 4-iodo calix[4]arenes 18a and 18b (241.7 mg, 0.2 mmol), $Pd(OAc)_2$ (27.0 mg, 0.12 mmol), and tri-o-tolylphosphine (121.8 mg, 0.4 mmol) was treated with vacuum and refilled with Ar three times. DMF (2.0 mL), $Et_3N$ (0.66 mL, 4.8 mmol), and ethyl acrylate (0.52 mL, 4.8 mmol) were added. The reaction mixture was stirred at 80° C. and monitored by ESI mass spectrometry. After 6 hours more $Pd(OAc)_2$ (13.5 mg, 0.12 mmol) and tri-o-tolylphosphine (30.5 mg, 0.1 mmol) were added. After reaction was finished as indicated by ESI, the reaction mixture was cooled and filtered through Celite. The filtrate was washed with brine, dried ($Na_2SO_4$), and concentrated. Flash chromatography (20% EtOAc in hexanes) of the residue provided unsaturated tetra-ester 19a in partial cone conformation (64.6 mg, 29%) and 19b in cone conformation (111.5 mg, 51%). For partial cone conformer 19a: $^1$H NMR (500 MHz, $CDCl_3$) δ 7.73 (d, J=15.8 Hz, 1H), 7.65 (d, J=16.0 Hz, 1H), 7.46 (s, 2H), 7.30 (s, 2H), 7.16 (d, J=15.6 Hz, 2H), 7.13 (d, J=2.0 Hz, 2H), 6.43 (d, J=15.8 Hz, 1H), 6.38 (d, J=16.0 Hz, 1H), 6.32 (d, J=2.0 Hz, 2H), 5.97 (d, J=15.6 Hz, 2H), 4.31 (q, J=7.2 Hz, 2H), 4.26 (q, J=7.4 Hz, 2H), 4.23-4.15 (m, 4H), 4.05 (d, J=13.5 Hz, 2H), 3.92 (t, J=6.9 Hz, 2H), 3.80 (m, 2H), 3.64 (m, 6H), 3.38 (m, 2H), 3.08 (d, J=13.5 Hz, 2H), 2.03 (m, 1H), 1.92 (m, 4H), 1.80 (m, 4H), 1.37 (t, J=7.2 Hz, 3H), 1.33 (t, J=7.2 Hz, 3H), 1.30 (t, J=7.1 Hz, 6H), 1.26 (m, 3H), 1.14 (d, J=7.0 Hz, 6H), 1.04 (d, J=5.9 Hz, 6H), 1.01 (d, J=6.7 Hz, 6H), 0.76 (d, J=6.5 Hz, 6H); for cone conformer 19b: $^1$H NMR (500 MHz, $CDCl_3$) δ 7.35 (d, J=16.0 Hz, 4H), 6.80 (s, 8H), 6.08 (d, J=16.0 Hz, 4H), 4.41 (d, J=13.3 Hz, 4H), 4.22 (q, J=7.1 Hz, 8H), 3.95 (t, J=6.9 Hz, 8H), 3.17 (d, J=13.3 Hz, 4H), 1.77 (m, 12H), 1.32 (t, J=7.1 Hz, 12H), 0.96 (d, J=6.7 Hz, 24H); $^{13}$C NMR (125 MHz, $CDCl_3$) δ 167.3 (4C), 158.6 (4C), 144.7 (4C), 135.5 (8C), 129.1 (4C), 128.5 (8C), 116.4 (4C), 74.0 (4C), 60.4 (4C), 39.0 (4C), 31.2 (4C), 25.5 (4C), 23.0 (8C), 14.5 (4C); HRMS (ESI) m/z calcd for $C_{68}H_{88}Na_1O_{12}$ $(M+Na)^+$ 1119.6173. found 1119.6274.

Example 18

Tetra-ester 20. The unsaturated tetra-ester 19b in cone conformation (86.5 mg, 0.08 mmol) in THF (0.6 mL) and EtOH (0.6 mL) under $N_2$ was treated with Pd on activated carbon (10%, 20 mg) and ammonium formate (200 mg, 3.17 mmol). The reaction mixture in a sealed tube was stirred at 60° C. and monitored by ESI. After hydrogenation was complete (~10 hours), the reaction mixture was cooled and filter through Celite. The filtrate was concentrated and purified by MPLC (20% EtOAc in hexanes) to give tetra-ester 20 (67.9 mg, 78%) as a colorless oil. $^1$H NMR (500 MHz, $CDCl_3$) δ 6.44 (s, 8H), 4.35 (d, J=13.0 Hz, 4H), 4.11 (q, J=7.4 Hz, 8H), 3.88 (t, J=7.5 Hz, 8H), 3.04 (d, J=13.0, 4H), 2.62 (br t, J=8.2 Hz, 8H), 2.39 (br t, J=8.2 Hz, 8H), 1.77 (m, 2H), 1.24 (t, J=7.4 Hz, 12H), 0.95 (d, J=6.1 Hz, 24H); $^{13}$C NMR (75 MHz, $CDCl_3$) δ 173.3 (4C), 155.0 (4C), 134.9 (8C), 133.8 (4C), 128.0 (8C), 73.7 (4C), 60.4 (4C), 39.0 (4C), 36.5 (4C), 31.2 (4C), 30.6 (4C), 25.6 (4C), 23.0 (8C), 14.5 (4C); HRMS (ESI) m/z calcd for $C_{68}H_{96}Na_1O_{12}$ $(M+Na)^+$ 127.6799. found 1127.6825.

Example 19

Tetra-amine 21. Tetra-ester 20 (112.8 mg, 0.1 mmol) and N,N-dimethyl ethylenediamine (0.44 mL, 4.0 mmol) in a sealed tube was stirred at 140° C. for 20 hours. After cooling, the reaction mixture was partitioned between $CH_2Cl_2$ and water. The organic phase was separated, dried ($Na_2SO_4$), and concentrated under vacuo to give the tetra-amine 21 (115.8 mg, 91%) as a light yellow solid. $^1$H NMR (300 MHz, $CDCl_3$) δ 6.56 (t, J=5.5 Hz, 4H), 6.45 (s, 8H), 4.35 (d, J=13.2 Hz, 4H), 3.87 (t, J=7.2 Hz, 8H), 3.32 (td, J=6, 6 Hz, 8H), 3.40 (d, J=13.2 Hz, 4H), 5.27 (br t, J=7.8 Hz, 8H), 2.41 (t, J=6.1 Hz, 8H), 2.27 (br t, J=7.8 Hz, 8H), 2.22 (s, 24H), 1.79 (m, 12H), 0.95 (d, J=7.0 Hz, 24H); $^{13}$C NMR (75 MHz, $CDCl_3$) δ 173.0 (4C), 154.9 (4C), 134.9 (8C), 134.3 (4C), 128.0 (8C), 73.8 (4C), 58.3 (4C), 45.4 (8C), 39.1 (4C), 38.8 (4C), 37.2 (4C), 31.3 (4C), 31.2 (4C), 25.6 (4C), 23.0 (8C); HRMS (ESI) m/z calcd for $C_{76}H_{122}N_8O_8$ $(M+2H)^{2+}$ 637.4693. found 637.4686.

Example 20

Tetra-acid 22. Tetra-ester 2 (2.0 g, 2.0 mmol) in ethanol (30 mL) and water (20 mL) was treated with NaOH (2.0 g, 50 mmol). The reaction mixture was refluxed for 24 hours. After cooling, the reaction mixture was acidified with 50% $H_2SO_4$ to pH=1. The precipitate was collected after filtration, washed with water, and dried under vacuo to provide the tetra-acid 21 (1.8 g, 100%) as a white solid. $^1$H NMR (300 MHz, DMSO) δ 12.2 (s, 4H), 6.93 (s, 8H), 4.77 (d, J=12.5 Hz, 4H), 4.59 (s, 8H), 3.21 (d, J=12.5 Hz, 4H), 1.06 (s, 36H); HRMS (ESI) m/z calcd for $C_{52}H_{64}Na_1O_{12}$ $(M+Na)^+$ 903.4295. found 903.4314.

Example 21

Tetra-triazole 23. The suspension of tetra-acid 23 (264.3 mg, 0.3 mmol) in benzene was treated with thionyl chloride (1.3 mL, 18.0 mmol). The reaction mixture was refluxed for 3 hours. After removal of volatile components under vacuo, the residue was coevaporated with benzene. The residue was dissolved in $CH_2Cl_2$, filtered through cotton, and concentrated. Without further purification, the crude acylchloride in THF (5.0 mL) was treated with 1H, 1,2,4-triazole-1-propanamine (Wright, Jr. et al., J. Med. Chem. 29, 523-530 (1986)) (227.1 mg, 1.8 mmol) and $Et_3N$ (0.33 mL, 2.4 mmol) at 0° C. and allowed warm to room temperature. The reaction was monitored by ESI. After 18 hours the reaction mixture was diluted with $CH_2Cl_2$ and filtered through Celite. The filtrate was concentrated, and then partitioned between $CH_2Cl_2$ and NH$_4$Cl aqueous solution. The aqueous layer was adjusted to pH=1 with 1N HCl. The organic phase was collected and washed with brine. Then the organic phase was washed with NaHCO$_3$ saturated aqueous solution and brine, dried (Na$_2$SO$_4$), and concentrated to give the tetra-triazole 23 (233.0 mg, 59%) as a white solid. HRMS (ESI) m/z calcd for C$_{72}$H$_{96}$N$_{16}$Na$_2$O$_8$ (M+2Na)$^{2+}$ 679.3696. found 679.3747.

Example 22

Dinitrile 24. To a suspension of 4-t-butylcalix[4]arene 1 (649.0 mg, 1.0 mmol) in acetone (20 mL) was added K$_2$CO$_3$ (552.8 mg, 4.0 mmol). After the reaction mixture was refluxed for 1 hour, chloroacetonitrile (0.25 mL, 4.0 mmol) and NaI (599.6 mg, 4.0 mmol) were added, and the mixture was heated under reflux for another 15 hours. After cooling, the reaction mixture was filtered through Celite and the filtrate was washed by brine, dried (Na$_2$SO$_4$), and concentrated. Dinitrile 24 (418.8 mg) was obtained as white crystal by crystallization from a solution of CH$_2$Cl$_2$ and ethanol (~1:4). More dinitrile 24 (62.3 mg) was collected from mother liquor by flash chromatography (20% EtOAc in hexanes) to provide 66% total yield. $^1$H NMR (500 MHz, CDCl$_3$) δ 7.12 (s, 4H), 6.72 (s, 4H), 5.55 (s, 2H), 4.80 (s, 4H), 4.22 (d, J=13.1 Hz, 4H), 3.44 (d, J=13.1 Hz, 4H), 1.33 (s, 18H), 0.88 (s, 18H); $^{13}$C NMR (125 MHz, CDCl$_3$) δ 150.1 (2C), 148.9 (2C), 148.7 (2C), 142.7 (2C), 132.0 (4C), 128.0 (4C), 126.3 (4C), 125.5 (4C), 115.3 (2C), 60.6 (2C), 34.1 (2C), 34.1 (2C), 31.9 (6C), 31.8 (4C), 31.0 (6C); HRMS (ESI) m/z calcd for C$_{48}$H$_{58}$N$_2$Na$_1$O$_4$ (M+Na)$^+$ 749.4294. found 749.4264.

Example 23

Boc protected diguanidine 25 and Boc protected mono-guanidine-mono-amine 26. To a solution of dinitrile 24 (746.3 mg, 1.0 mmol) in ether (10 mL) and THF (5.0 mL) at 0° C. was added LiAlH$_4$ (0.8 M in ether, 3.8 mL). The reaction mixture was allowed warm to room temperature and stirred for 6 hours. The reaction was carefully quenched with water (360 μL) and 15% NaOH (120 μL) sequentially, the reaction mixture was filtered through filter paper, and the filtrate was washed with brine, dried (Na$_2$SO$_4$), and concentrated to give the diamine as a white solid.

The above diamine, 1,3-bis(tert-butoxycarbonyl)-2-methyl-2-thiopseudourea (656.2 mg, 2.3 mmol) were dissolved in CH$_2$Cl$_2$ (5 mL) followed with addition of HgCl$_2$ (613.6 mg, 2.3 mmol) and Et$_3$N (0.9 mL, 6.8 mmol). After being stirred for 15 hours, the reaction mixture was filtered through Celite. The filtrate was washed with brine, dried (Na$_2$SO$_4$), and concentrated. The residue was purified by MPLC (14% EtOAc in hexanes) to give Boc protected diguanidine 25 (476.4 mg, 40%) and Boc protected mono-guanidine-mono-amine 26 (152.9 mg, 14%). Compound 25: $^1$H NMR (500 MHz, CDCl$_3$) δ 11.45 (s, 2H), 8.94 (t, J=6.3 Hz, 2H), 7.00 (s, 4H), 6.98 (s, 2H), 6.74 (s, 4H), 4.23 (d, J=12.9 Hz, 4H), 4.15 (t, J=5.1 Hz, 4H), 4.04 (dt, J=6.3, 5.1 Hz, 4H), 3.28 (d, J=12.9 Hz, 4H), 1.50 (s, 18H), 1.37 (s, 18H), 1.28 (s, 18H), 0.93 (s, 18H); $^{13}$C NMR (75 MHz, CDCl$_3$) δ 163.7 (2C), 156.6 (2C), 152.8 (2C), 150.9 (2C), 149.8 (2C), 147.0 (2C), 141.3 (2C), 132.5 (4C), 127.8 (4C), 125.7 (4C), 125.2 (4C), 83.0 (2C), 79.4 (2C), 74.6 (2C), 41.1 (2C), 34.1 (2C), 34.0 (2C), 31.9 (6C), 31.8 (4C), 31.2 (6C), 28.5 (6C), 28.1 (6C); HRMS (ESI) m/z calcd for C$_{70}$H$_{104}$N$_6$O$_{12}$ (M+2H)$^{2+}$ 610.3856. found 610.3785.

Compound 26: $^1$H NMR (500 MHz, CDCl$_3$) δ11.46 (s, 1H), 8.99 (t, J=5.5 Hz, 1H), 7.80 (s, 2H), 7.01 (m, 4H), 6.91 (s, 2H), 6.87 (s, 2H), 6.48 (t, J=5.0 Hz, 1H), 4.23 (d, J=13.0 Hz, 2H), 4.23 (d, J=13.3, 2H), 4.16 (t, J=5.0 Hz, 2H), 4.09 (t, J=5.0 Hz, 2H), 4.04 (dt, J=5.5, 5.0 Hz, 2H), 3.79 (dt, J=5.0, 5.0 Hz, 2H), 3.33 (d, J=13.0 Hz, 2H), 3.32 (d, J=13.3 Hz, 2H), 1.50 (s, 9H), 1.43 (s, 9H), 1.34 (s, 9H), 1.25 (s, 8H), 1.06 (s, 9H), 1.03 (s, 9H); HRMS (ESI) m/z calcd for C$_{64}$H$_{93}$N$_4$O$_{10}$ (M+H)$^+$ 1077.6892. found 1077.6906.

Example 24

5,11,17,23-Tetra-tert-butyl-25,27-bis(2-guanidinoethoxy)-26,28-dihydroxy calix[4]arene trifluoroacetic acid salt 27. Diguanidine 25 (476.4 mg, 0.39 mmol) was dissolved in a solution of CH$_2$Cl$_2$ with 40% TFA and 5% anisole (5.0 mL) and the mixture was stirred at room temperature for 15 hours. The volatile components were removed under vacuo. The residue was partitioned between CH$_2$Cl$_2$ and water and the aqueous phase was adjusted to pH=8. The organic phase was separated, dried (Na$_2$SO$_4$), and concentrated to give the calixarene 27•2TFA salt (407.8 mg, 100%) as an off-white solid. $^1$H NMR (500 MHz, CD$_3$OD) δ 7.19 (s, 4H), 7.02 (s, 4H), 4.26 (d, J=13.2 Hz, 4H), 4.22 (t, J=5.2 Hz, 4H), 3.81 (t, J=5.2 Hz, 4H), 3.48 (d, J=13.2 Hz, 4H), 1.27 (s, 18H), 1.03 (s, 18H); $^{13}$C NMR (125 MHz, CDCl$_3$ and CD$_3$OD) δ 157.6 (2C), 148.9 (2C), 128.4 (2C), 148.1 (2C), 143.9 (2C), 132.5 (4C), 127.9 (4C), 126.1 (4C), 125.5 (4C), 74.0 (2C), 41.5 (2C), 34.1 (2C), 33.8 (2C), 31.5 (4C), 31.3 (6C), 30.8 (6C); HRMS (ESI) m/z calcd for C$_{50}$H$_{72}$N$_6$O$_4$ (M+2H)$^{2+}$ 410.2808. found 410.2787.

Example 25

5,11,17,23-Tetra-tert-butyl-25-(2-aminoethoxy)-27-(2-guanidinoethoxy)-26,28-dihydroxy Calix[4]arene trifluoroacetic acid salt 28. According to the procedure described for calixarene 27, mono-guanidine-mono-amine 26 (152.9 mg, 0.14 mmol) was treated with a CH$_2$Cl$_2$ solution (2.0 mL) of TFA (40%) and anisole (5%). Standard workup and purification give the calixarene 28•2TFA salt (139.6 mg, 99%) as an off-white solid. $^1$H NMR (500 MHz, CD$_3$OD) δ 7.21 (s, 4H), 6.98 (m, 4H), 4.26 (m, 4H), 4.22 (d, J=13.2 Hz, 2H), 4.18 (d, J=13.2 Hz, 2H), 3.80 (m, 2H), 3.61 (m, 2H), 3.50 (d, J=13.2 Hz, 2H), 3.49 (d, J=13.2 Hz, 2H), 1.29 (s, 18H), 1.00 (m, 18H); HRMS (ESI) m/z calcd for C$_{49}$H$_{70}$N$_4$O$_4$ (M+2H)$^{2+}$ 389.2698. found 389.2686.

Example 26

5,11,17,23-Tetra-tert-butyl-25,27-bis(3-cyanopropyloxy)-26,28-dihydroxy calix[4]arene 29. 4-tert-Butylcalixarene 1 (1.3 g, 2.0 mmol) in acetone (20 mL) was treated with K$_2$CO$_3$ (1.6 g, 12.0 mmol). The reaction mixture was refluxed for 1 hour followed by addition of 4-bromo-butyronitrile (1.6 mL, 16.0 mmol). After 16 hours the reaction mixture was cooled and filtered through Celite. The filtrate was washed with brine, dried (Na$_2$SO$_4$), and concentrated. Crystallization from ethanol gave dinitrile 29 (1.3 g) as a white crystal. More desired product (158.6 mg, 91% in total) was collected from the mother liquor by flash chromatography (20% EtOAc in hexanes). $^1$H NMR (500 MHz, CDCl$_3$) δ 7.44 (s, 2H), 7.06 (s, 4H), 6.86 (s, 4H), 4.17 (d, J=13.2 Hz, 4H), 4.09 (t, J=5.5 Hz, 4H), 3.38 (d, J=13.2 Hz, 4H), 3.05 (t, J=7.0 Hz, 4H), 2.34 (tt, J=7.0, 5.5 Hz, 4H), 1.28 (s, 18H), 1.00 (s, 18H); HRMS (ESI) m/z calcd for C$_{52}$H$_{66}$N$_2$Na$_1$O$_4$ (M+Na)$^+$ 805.4920. found 805.4908.

Example 27

5,11,17,23-Tetra-tert-butyl-25,26,27,28-tetrakis(3-cyanopropyloxy)calix[4]arene 30. Dinitrile (1.4 g, 1.8 mmol) in DMF (20 mL) was treated with NaH (432 mg, 18.0 mmol) at room temperature for 1 hour followed with addition of 4-bromo-butyronitrile (9.0 mL, 90.0 mmol). The reaction mixture was stirred at 75° C. for 20 hours, and then was partitioned between $CH_2Cl_2$ and $NH_4Cl$ sat. aqueous solution. The organic layer was washed with $NH_4Cl$ sat. aqueous solution (3×100 mL), dried ($Na_2SO_4$), and concentrated. After removal of remained 4-bromo-butyronitrile at 68° C. under vacuo, the residue was purified by flash chromatography (35% EtOAc in hexanes) to give the tetra-nitrile 30 (1.3 g, 81%) as a white solid. $^1$H NMR (500 MHz, $CDCl_3$) δ 6.80 (s, 8H), 4.26 (d, J=12.3 Hz, 4H), 4.02 (t, J=7.5 Hz, 8H), 3.22 (d, J=12.3 Hz, 4H), 2.62 (t, J=7.5 Hz, 8H), 2.28 (tt, J=7.5, 7.5 Hz, 8H), 1.08 (s, 36H); $^{13}$C NMR (75 MHz, $CDCl_3$) δ 152.6 (4C), 145.6 (4C), 133.4 (8C), 125.6 (8C), 119.6 (4C), 73.1 (4C), 34.1 (4C), 31.5 (12C), 31.2 (4C), 26.0 (4C), 14.4 (4C); HRMS (ESI) m/z calcd for $C_{60}H_{76}N_4Na_1O_4$ $(M+Na)^+$ 939.5764. found 939.5776.

Example 28

Boc protected tetra-guanidine 31. To the solution of tetranitrile (458.5 mg, 0.5 mmol) and $CoCl_2$ (519.4 mg, 4.0 mmol) in methanol (10 mL) was added batchwise $NaBH_4$ (756.6 mg, 20 mmol). After being stirred at room temperature for 26 hours, the reaction mixture was diluted with $CH_2Cl_2$. 3N HCl (~30 mL) was added and vigorously stirred until the black precipitate was completely dissolved. The aqueous layer was adjusted to pH=10 with 15% NaOH, and then extracted with $CH_2Cl_2$. The combined $CH_2Cl_2$ phase was dried ($Na_2SO_4$) and concentrated to provide the crude tetraamine (438.2 mg) as a dark pink solid.

To a solution of above tetra-amine (166.5 mg, ~0.19 mmol) was added in sequence 1,3-bis(tert-butoxycarbonyl)-2-methyl-2-thiopseudourea (227.4 mg, 0.8 mmol), $HgCl_2$ (212.6 mg, 0.8 mmol), and $Et_3N$ (0.33 mL, 2.3 mmol). After being stirred for 15 hours the reaction mixture was filtered through Celite, and the filtrate was partitioned between $CH_2Cl_2$ and $NaHCO_3$ aqueous solution. The organic phase was dried ($Na_2SO_4$) and concentrated. Purification with MPLC (15% EtOAc in hexanes) provided Boc protected tetra-guanidine 31 (103.6 mg, 29%). 1H NMR (500 MHz, $CDCl_3$) δ 11.51 (s, 4H), 8.38 (t, J=5.0 Hz, 4H), 6.75 (s, 8H), 4.33 (d, J=12.6 Hz, 4H), 3.90 (t, J=7.6 Hz, 8H), 3.48 (td, J=7.3, 5.0 Hz, 8H), 3.12 (d, J=12.6 Hz, 4H), 2.00 (m, 8H), 1.68 (m, 8H), 1.48$^+$ (s, 36H), 1.48$^-$ (s, 36H), 1.07 (s, 36H); $^{13}$C NMR (75 MHz, $CDCl_3$) δ 163.8 (4C), 156.3 (4C), 153.5 (4C), 153.4 (4C), 144.6 (4C), 133.9 (8C), 125.1 (8C), 83.0 (4C), 79.2 (4C), 74.6 (4C), 41.1 (4C), 34.0 (4C), 31.6 (12C), 31.4 (4C), 28.5 (12C), 28.3 (12C), 27.7 (4C), 25.9 (4C); HRMS (ESI) m/z calcd for $C_{104}H_{165}N_{12}NaO_{20}$ $(M+H+Na)^{2+}$ 962.6080. found 962.6090.

Example 29

5,11,17,23-Tetra-tert-butyl-25,26,27-tris(4-guanidinobutyroxy)-28-hydroxy calix[4]arene trifloroacetic acid salt 32. According to the procedure described for calixarene 27, tetra-guanidine 31 (80.6 mg, 0.04 mmol) was treated with a $CH_2Cl_2$ solution (1.0 mL) of TFA (40%) and anisole (5%). Standard workup and purification give the calixarene 32·3TFA salt (54.5 mg, 98%) as an off-white solid. $^1$N NMR (500 MHz, $CD_3OD$) δ 7.22 (s, 2H), 7.14 (s, 2H), 6.61 (d, J=2.0 Hz, 2H), 6.56 (d, J=2.0 Hz, 2H), 4.38 (d, J=12.5 Hz, 2H), 4.31 (d, J=13.0 Hz, 2H), 3.98 (m, 2H), 3.88 (m, 2H), 3.35 (m, 2H), 3.28 (m, 4H), 3.28 (d, J=12.5 Hz, 2H), 3.24 (d, J=13.0 Hz, 2H), 2.34 (m, 2H), 2.05 (m, 2H), 1.80 (m, 2H), 1.75 (m, 2H), 1.66 (m, 2H), 1.59 (m, 2H), 1.35 (s, 9H), 1.33 (s, 9H), 0.84 (s, 18H); HRMS (ESI) m/z calcd for $C_{59}H_{91}N_9O_4$ $(M+2H)^{2+}$ 494.8597. found 494.8576.

Example 30

Dinitrile 33. According to the procedure described for dinitrile 24, calix[4]arene 13 in acetone (5.0 mL) was treated with $K_2CO_3$ (138.2, 1.0 mmol), chloroacetonitrile (0.13 mL, 2.0 mmol), and NaI (299.8 mg, 2.0 mmol). Standard workup and purification by crystallization gave dinitrile 33 (106.8 mg, 43%) and the trisubstituted analog (74.1 mg, 27.4%). For dinitrile 33: $^1$H NMR δ 7.13 (d, J=7.5 Hz, 4H), 6.82 (d, J=7.5 Hz, 4H), 6.77 (t, J=7.5 Hz, 2H), 6.75 (t, J=7.5 Hz, 2H), 6.02 (s, 2H), 4.85 (s, 4H), 4.25 (d, J=13.6 Hz, 4H), 3.52 (d, J=13.6 Hz, 4H).

Example 31

Boc protected diguanidine 34 and Boc protected monoguanidine-mono-amine 35. According to the procedure described for the preparation of diguanidine 25 and monoguanidine-mono-amine 26, dinitrile 33 (106.8 mg, 0.21 mmol) in THF (4.0 mL) was treated with $LiAlH_4$ (0.8 M in ether, 0.8 mL). After standard workup, the corresponding diamine was obtained as white solid. Without further purification, the diamine was dissolved in $CH_2Cl_2$ (5 mL) and treated with 1,3-Bis(tert-butoxycarbonyl)-2-methyl-2-thiopseudourea (133.6 mg, 0.46 mmol), $HgCl_2$ (124.9 mg, 0.46 mmol), and $Et_3N$ (0.19 mL, 1.39 mmol). Standard workup and chromatography (20% EtOAc in hexanes) gave diguanidine 34 (54.1 mg, 26%) and mono-guanidine-mono-amine 35 (23.6 mg, 13%). For diguanidine 34: $^1$H NMR (300 MHz, $CDCl_3$) δ 11.48 (s, 2H), 9.00 (br t, J≈5 Hz, 2H), 7.58 (s, 2H), 7.02 (d, J=7.9 Hz, 4H), 6.83 (d, J=7.5 Hz, 4H), 6.68 (dd, J=7.8, 6.9 Hz, 2H), 6.62 (t, J=7.5 Hz, 2H), 4.24 (d, J=13.2 Hz, 4H), 4.14 (m, 8H), 3.35 (d, J=13.2 Hz, 4H), 1.50 (s, 18H), 1.35 (s, 18H); $^{13}$C NMR (75 MHz, $CDCl_3$) δ 163.7 (2C), 156.6 (2C), 153.6 (2C), 152.8 (2C), 151.7 (2C), 133.1 (4C), 129.2 (4C), 128.6 (4C), 127.9 (4C), 125.6 (2C), 118.8 (2C), 83.0 (2C), 79.4 (2C), 75.0 (2C), 41.0 (2C), 31.5 (4C), 28.5 (6C), 28.0 (6C); HRMS (ESI) m/z calcd for $C_{54}H_{70}N_6Na_1O_{12}$ $(M+Na)^+$ 1017.4949. found 1017.5015.

For mono-guanidine-mono-amine 35: $^1$H NMR (300 MHz, $CDCl_3$) δ 11.49 (s, 1H), 9.02 (br t, J=5.4 Hz, 1H), 8.07 (s, 2H), 7.04 (d, J=7.2 Hz, 2H), 7.03 (d, J=7.2 Hz, 2H), 6.93 (d, J=7.3 Hz, 2H), 6.91 (d, J=7.1 Hz, 2H), 6.76 (dd, J=7.3, 7.1 Hz, 1H), 6.75 (dd, J=17.3, 7.1 Hz, 1H), 6.64 (t, J=7.4 Hz, 2H), 6.44 (br t, J≈5 Hz, 1H), 4.26 (d, J=12.9 Hz, 2H), 4.24 (d, J=12.9 Hz, 2H), 4.17 (m, 2H), 4.12 (m, 4H), 3.84 (br dt, J≈5, 5 Hz, 2H), 3.39 (d, J=12.9 Hz, 4H), 1.50 (s, 9H), 1.42 (s, 9H), 1.33 (s, 9H); $^{13}$C NMR (75 MHz, $CDCl_3$) δ 163.7, 156.6, 153.3, 152.8, 151.3, 151.2, 133.5 (2C), 133.4 (2C), 129.4 (4C), 128.7 (4C), 128.2 (2C), 127.7 (2C), 126.0 (2C), 125.9 (2C), 119.4 (2C), 83.0 (2C), 79.4, 75.6, 75.2, 41.1, 40.9, 31.7 (2C), 31.6 (2C), 28.6 (3C), 28.5 (3C), 28.0 (3C); HRMS (ESI) m/z calcd for $C_{48}H_{60}N_4Na_1O_{10}$ $(M+Na)^+$ 875.4207. found 875.4196.

Example 32

25,27-Bis(2-guanidinoethoxy)-26,28-dihydroxy calix[4] arene trifluoroacetic acid salt 36. According to the procedure described for the preparation of calixarene derivative 27, diguanidine 34 (53.0 mg, 0.05 mmol) was treated with a $CH_2Cl_2$ solution (1.0 mL) of TFA (40%) and anisole (5%). Standard workup and purification give the calixarene 36•2TFA salt (139.6 mg, 99%) as a white solid (40.3 mg, 92%). $^1$H NMR (300 MHz, CD$_3$OD) δ 7.14 (d, J=7.3 Hz, 4H), 6.79 (d, J=7.3 Hz, 4H), 6.74 (t, J=7.3 Hz, 2H), 6.60 (t, J=7.3 Hz, 2H), 4.28 (d, J=12.0 Hz, 4H), 4.18 (t, J=4.9 Hz, 4H), 3.81 (t, J=4.9 Hz, 4H), 3.47 (d, J=13.0 Hz, 4H); $^{13}$C NMR (75 MHz, CD$_3$OD) δ 159.4 (2C), 153.8 (2C), 152.8 (2C), 134.3 (4C), 130.5 (4C), 130.1 (4C), 129.6 (4C), 126.7 (2C), 121.1 (2C), 75.6 (2C), 42.9 (2C), 32.0 (4C); HRMS (ESI) m/z calcd for C$_{34}$H$_{39}$N$_6$O$_4$ (M+H)$^+$ 595.3033. found 595.2967.

Example 33

25,27-Bis[(ethoxycarbonyl)methoxy]-26,28-dihydroxy calix[4]arene 37. According to the procedure described for the preparation of tetra-ester 2, calix[4]arene 13 (339.6 mg, 0.8 mmol) in acetone (10 mL) was treated with K$_2$CO$_3$ (221.1 mg, 1.6 mmol) and ethyl bromoacetate (0.35 mL, 3.2 mmol). Standard workup and chromatography (3% EtOAc in CH$_2$Cl$_2$) provided the diester calixarene derivative 37 (254.5 mg, 53%). $^1$H NMR (300 MHz, CDCl$_3$) δ 7.61 (s, 2H), 7.04 (d, J=7.5 Hz, 4H), 6.90 (d, J=7.5 Hz, 4H), 6.74 (t, J=7.5 Hz, 2H), 6.65 (t, J=7.5 Hz, 2H), 4.72 (s, 4H), 4.48 (d, J=13.2 Hz, 4H), 4.33 (t, J=7.1 Hz, 4H), 3.39 (d, J=13.2 Hz, 4H), 1.35 (t, J=7.1 Hz, 6H); HRMS (ESI) m/z calcd for C$_{36}$H$_{36}$Na$_1$O$_8$ (M+H)$^+$ 619.2308. found 619.2306.

Example 34

25,27-Bis[N—(N,N-diethyl-2-aminoethyl)carbamoyl-methoxy]-26,28-dihydroxy calix[4]arene 38. According to the procedure described for the preparation of the tetra-amine 3, diester 37 (29.8 mg, 0.05 mmol) in toluene (0.2 mL) was treated with N,N-dimethyl ethylenediamine (0.11 mL, 1.0 mmol) at 80° C. for 36 hours. After standard purification, diamine 38 (24.0 mg, 70%) was obtained as a light brown solid. $^1$H NMR (500 MHz, CD$_3$OD) δ 7.14 (d, J=7.5 Hz, 4H), 6.93 (d, J=7.5 Hz, 4H), 6.73 (t, J=7.5 Hz, 4H), 4.62 (s, 4H), 4.23 (d, J=13.0 Hz, 4H), 3.61 (t, J=6.6 Hz, 4H), 3.51 (d, J=13.0 Hz, 4H), 2.65 (t, J=6.6 Hz, 4H), 2.29 (s, 12H); $^{13}$C NMR (75 MHz, CD$_3$OD) δ 170.6 (2C), 153.2 (2C), 152.4 (2C), 134.3 (4C), 130.6 (4C), 130.1 (4C), 128.9 (4C), 127.4 (2C), 121.4 (2C), 75.4 (2C), 59.2 (2C), 45.5 (4C), 37.7 (2C), 32.3 (4C); HRMS (ESI) m/z calcd for C$_{40}$H$_{49}$N$_4$O$_6$ (M+H)$^+$ 681.3652. found 681.3628.

Example 35

25,27-Bis[N-(2-aminoethyl)carbamoylmethoxy]-26,28-dihydroxy calix[4]arene 39. Diester 37 (29.8 mg, 0.05 mmol) in toluene (0.2 mL) was treated with N-Boc ethylenediamine (320.2 mg, 2.0 mmol) at 80° C. for 24 hours. After removal of the volatile component, the residue was dissolved in ether. The precipitate was removed by centrifugation and the ether solution was combined and concentrated. The residue was dissolved in a solution of CH$_2$Cl$_2$ (0.6 mL) with 40% TFA and 5% anisole and stirred at room temperature for 18 hours. After removal of the volatile components, the residue was partitioned between water and CH$_2$Cl$_2$. The aqueous phase was adjusted to pH=10, and extracted with CH$_2$Cl$_2$. The combined organic phase was dried (Na$_2$SO$_4$) and concentrated. The residue was dissolved in a minimum amount of CH$_2$Cl$_2$ and diamine 39 (42.5 mg, 100%) was precipitated with ether and collected as a white solid. $^1$H NMR (300 MHz, CDCl$_3$) δ 9.00 (br t, J=4.8 Hz, 2H), 8.16 (s, 2H), 7.10 (t, J=7.5 Hz, 4H), 6.97 (d, J=7.5 Hz, 4H), 6.83 (t, J=7.5 Hz, 2H), 6.75 (t, J=7.5 Hz, 2H), 4.60 (s, 4H), 4.18 (d, J=13.2 Hz, 4H), 3.48 (m, 8H), 2.93 (t, J=6.0 Hz, 4H), 1.82 (br s, 4H); $^{13}$C NMR (75 MHz, CDCl$_3$) δ 168.7 (2C), 152.0 (2C), 151.2 (2C), 133.0 (4C), 129.9 (4C), 129.2 (4C), 127.8 (4C), 126.9 (2C), 120.9 (2C), 75.2 (2C), 42.7 (2C), 41.8 (2C), 31.8 (4C); HRMS (ESI) m/z calcd for C$_{36}$H$_{41}$N$_4$O$_6$ (M+H)$^+$ 625.3026. found 625.2997.

Example 36

Antibacterial and Other Effects of Calixarene-Based Peptide Mimetics

Experimental
Bacterial Strains

*Pseudomonas aeruginosa* type 1 is a clinical, smooth strain isolate stereotyped by using the scheme of Homma et al., Japan. *J. Exp. Med.* 46, 329-336 (1976) and maintained in the lab by monthly transfer on blood agar plates. *E. coli* J96, IA2, and H5 are smooth strain, uropathogenic clinical isolates kindly maintained and provided by J. R. Johnson and described in Johnson et al., *J. Infect. Disease* 173, 920-926 (1996) for J96 and IA2 and in Johnson et al., *J. Infect. Disease* 173, 746-749 (1996) for H5. J5 is an *E. coli* rough strain initially referenced by G. R. Siber and discussed in Warren et al., *Infect. Immunity* 55, 1668-1673 (1987) and is analogous to the smooth strain *E. coli* 0111:B4 used in the BioWhittaker LAL endotoxin detection and quantitation kit described below. Gram-positive MN8 and MNHO are two patient isolates of *Staphylococcus aureus*, which were kindly provided by P. M. Schlievert and described in Bohach et al., *Rev. Infect. Diseases* 11, 75-82 (1989) for MNHO and in Schlievert et al., *J. Infect. Diseases* 147, 236-242 (1983) for MN8. All cultures are maintained on nutrient agar plates.

Bactericidal Assay

Pyrogen-free solutions were used throughout the assay. Log phase bacteria were obtained by transferring an overnight culture or scraping crystals off –85° C. glycerol stocks of overnight cultures. Bacteria were washed and resuspended in 0.9% sodium chloride with adjustment to an optical density at 650 nm which yields 3×10$^8$ CFU/ml. Bacteria were then diluted 1:10 in 0.08 M citrate phosphate buffer, pH 7.0 (prepared by mixing 0.08 M citric acid with 0.08 M dibasic sodium phosphate). Bacteria (0.15 ml) were incubated with the test compound in a final volume of 1.0 ml of buffer. The assay was done in 17×100 polypropylene tubes in a reciprocal water bath shaker at 37° C. for 30 minutes. Following this 30 minute (min) incubation, 10-fold dilutions were made in 0.9% sodium chloride. Dilutions were done to 10$^{-4}$ and 20 μl of each dilution was streaked across an agar plate. Gram-positive organisms were plated on nutrient agar plates containing 2% agar and Gram-negative organisms were plated on MacConkey agar (2%). Plates were incubated overnight at 37° C. and counted the next morning. The dilution containing 10-100 bacteria was counted and the number multiplied by 50 to adjust all counts to the number bacteria killed per milliliter. Compound concentrations were converted to logarithm base ten and graphed. Bactericidal activity was determined by dose response where LD50 values were determined by best fits of a sigmoidal curve to the dose response data.

Cells, Cultures, and Reagents

Human umbilical vein derived EC (HUVEC) were harvested from normal human umbilical cords by perfusion with 0.125% trypsin/EDTA as described in Groenewegen et al., *J. Exp. Med.* 164, 131-143 (1986). For determination of quiescent EC phenotype isolated ECs were immediately fixed in 1% paraformaldehyde. Human microvascular ECs (MVECs) were isolated. ECs were cultured in fibronectin coated tissue culture flasks in culture medium (RPMI-1640 with 20% human serum (HS), supplemented with 2 mM glutamine and 100 U/ml penicillin and 0.1 mg/ml streptomycin).

EC Proliferation Assay

EC proliferation was measured using a [$^3$H]thymidine incorporation assay. ECs were seeded at 5000 cells/well in flatbottomed tissue culture plates and grown for 3 days, in the absence or presence of regulators, in culture medium. During the last 6 hours of the assay, the culture was pulsed with 0.5 μCi [methyl-$^3$H]thymidine/well.

Tumor Model Studies

Female athymic nude mice (nu/nu, 5-6 weeks old) were used. These mice were purchased from the National Cancer Institute and allowed to acclimatize to local conditions for at least one week. Animals were given water and standard chow ad libitum, and were kept on a 12-hour light/dark cycle. All experiments were approved by the University of Minnesota Research Animal Resources ethical committee. Mice were randomized and split into three groups: 1) human serum albumin (10 mg/kg/day), 2) βpep-25 (10 mg/kg/day) and 3) peptide mimetic agent (5 mg or 10 mg/kg/day). Test compounds were diluted in DMSO and administered using osmotic mini-pumps (Durect, Cupertino, Calif.). Exponentially growing MA148 human ovarian carcinoma cells, kindly provided by Prof. Ramakrishnan (R. P. Dings et al., *Cancer Res.*, 63, 382-385 (2003)) or B16 mouse melanoma cells were cultured in RPMI 1640 medium (Life Technologies, Grand island, N.Y.). This medium was supplemented with 10% fetal bovine serum and 1% penicillin/streptomycin (Cellgro, Mediatech, Washington, D.C.) at 37° C. and 5% $CO_2$. One hundred microliters (100 μL) of this tumor cell suspension ($2 \times 10^7$ cells/ml) was then injected subcutaneously into the right flank of each mouse. Pumps were implanted into the left flank of mice for subcutaneous administration of compound over a 28-day treatment span.

Two variants of this model were used: prevention and intervention. For the prevention variant, treatment was initiated at the time of inoculation with MA148 cells. For the intervention variant, tumors were allowed to grow to an average size of 50 mm$^3$ (usually day 7 post inoculation) before treatment was initiated. With either variant, animals were randomized prior to the initiation of treatment. Treatment was administered via osmotic mini-pumps (Durect, Cupertino, Calif.), which were implanted subcutaneously in the left flank of mice. Concentrated solutions of βpep-25 or DBF analogs were formulated such that the 28-day treatment period would be covered by implantation of a single pump. In each study, control groups of animals were administered either PBS or PBS containing human serum albumin.

Immunohistochemistry.

Similar size tumors without apparent widespread necrosis were embedded in tissue freezing medium (Miles Inc.; Elkart, Ind.) and snap frozen in liquid nitrogen. Preparation and procedures were done as described earlier (17). Samples were subsequently incubated in a 1:50 dilution with phycoerythrin (PE)-conjugated monoclonal antibody to mouse CD-31 (PE-CAM-1) (Pharmingen; San Diego, Calif.) or a fluorescein isothiocyanate (FITC)-conjugated PCNA (Ab-1) (Oncogene; San Diego, Calif.) to stain for microvessel density (MVD) or proliferation, respectively. At the same time the sections were also stained for cell death using a TUNEL (terminal deoxyribonucleotidyl transferase-mediated dUTP-nick-end labeling) assay carried out according to the manufacturer's instructions (in situ cell death detection kit, fluorescein; TUNEL, Roche). The vessel density and architecture was quantified as described earlier [Griffioen et al., Biochemical Journal 354, 233-242 (2001)]. For leukocyte infiltration, a similar procedure was used with anti-CD45 and anti-CD8 antibodies.

Results

Currently, approximately 12 calixarene-based peptide mimetics have been synthesized and the chemical structures of some of these are illustrated in FIG. 2. In vitro activities were assessed using the bactericidal and endothelial cell proliferation assays described above. From this small library, two of these compounds were found to have reasonably good bactericidal activity (Compound 3 and Compound 11a) in the micromolar range (Table 1), and a different two were found to display excellent antiangiogenic activity (Compound 27 and KM0118 (40)) (FIG. 3 and Table 1), which is about 5- to 10-fold better than βpep-25.

The effectivity of these peptide mimetics as leukocyte infiltration enhancing agents in vivo is exemplified by the effects of KM0118 (40) and Compound 27 on infiltration of leukocytes into tumors of tumor bearing mice during studies described above. In cross-sections of tumors stained with fluorescently labeled anti-CD45 (general for leukocytes) and anti-CD8 (specific for helper T-cells, a sub-population of leukocytes) antibodies, leukocytes can be identified (FIG. 4). These agents are clearly more effective at increasing leukocyte infiltration into tumors than βpep-25 (i.e. "Anginex") (FIG. 4).

Examples 37-47

Preparation of Additional Compounds

Further exemplary calixarene derivatives can be made according to the following schemes and examples.

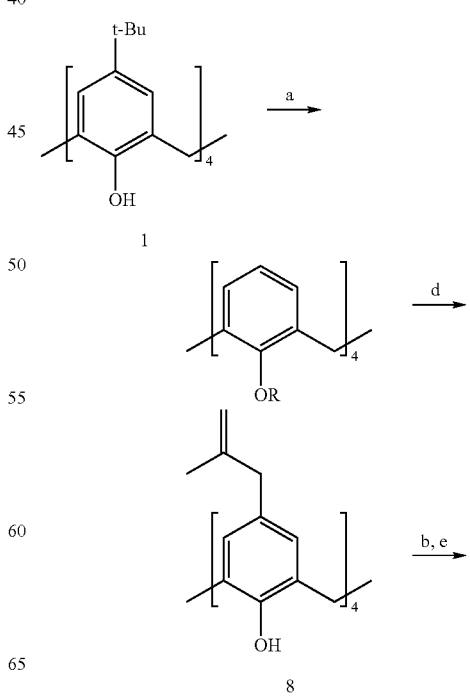

Scheme 7a

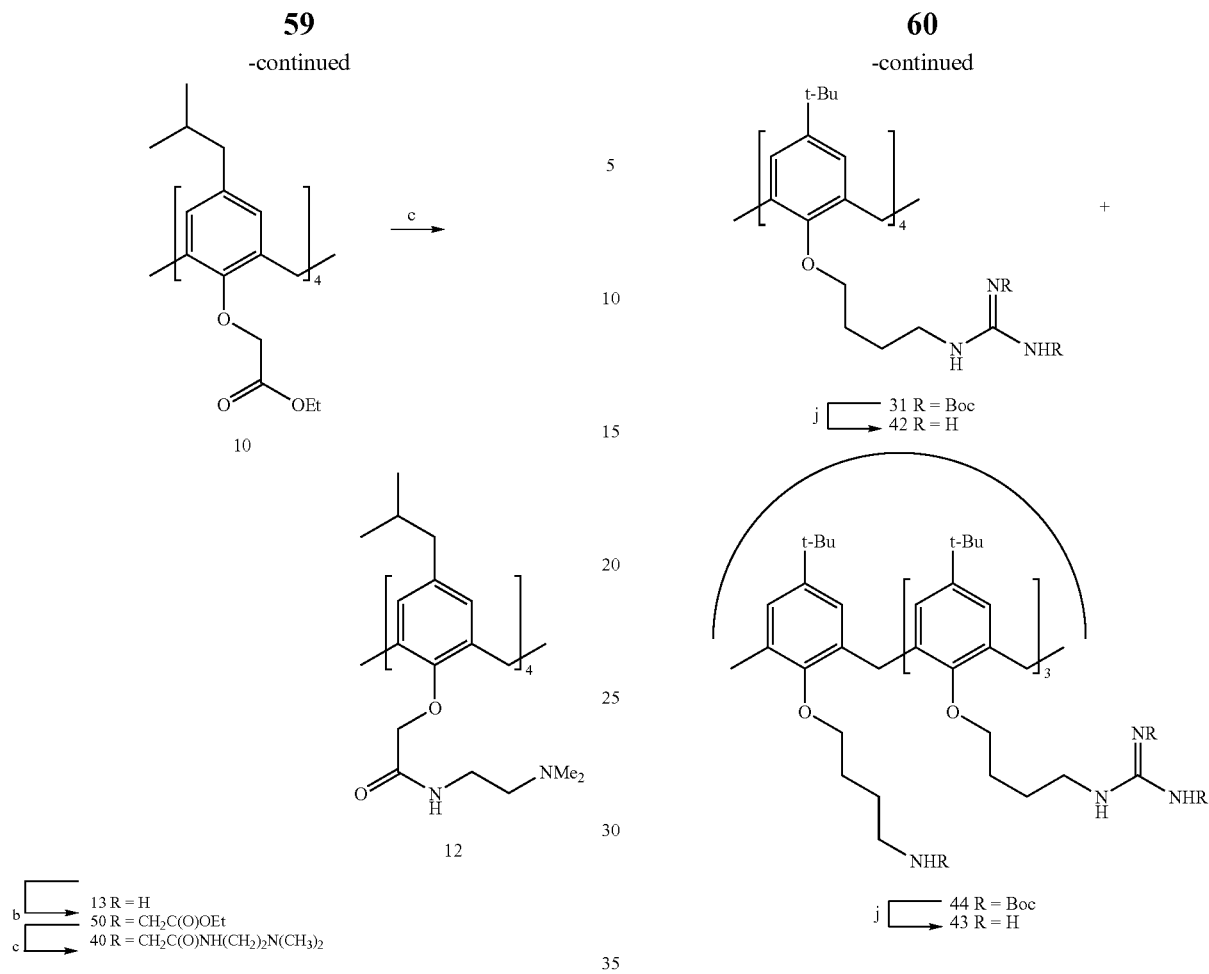
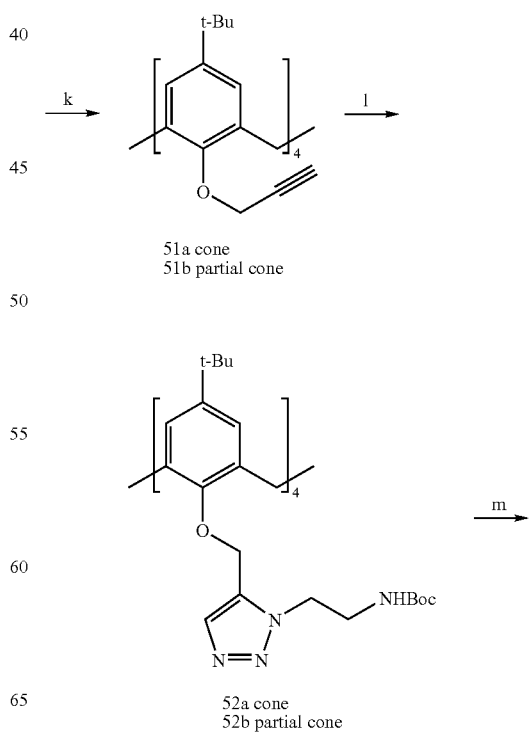
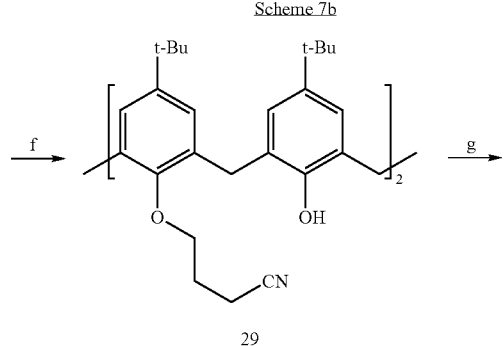
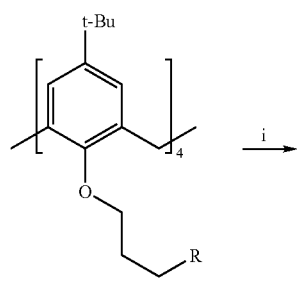

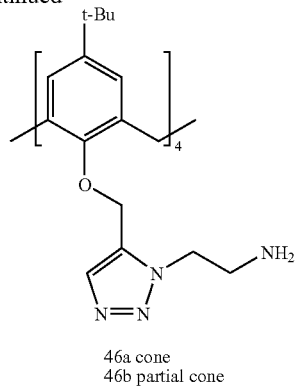

46a cone
46b partial cone

Example 37

Synthesis of Starting Materials

Calix[4]arene 13 (Gutsche et al., J. Am. Chem. Soc. 104, 2652-2653 (1982)), tetraethyl calix[4]arenetetraacetate 50 (Arnaud-Neu, et al. J. Am. Chem. Soc. 111, 8681-8691 (1989)), and calix[4]arenetetraamide 40 (Bryant, Jr. et al, Angew. Chem. Int. Ed. 39, 1641-1643 (2000)) were prepared according to literature procedures.

Example 38

Tetra-amine 45. According to the literature procedure (Wu et al., Angew. Chem. Int. Ed. 43, 3928-3932 (2004)), $NaBH_4$ (227.0 mg, 6.0 mmol) was added batchwise to the solution of tetranitrile (137.5 mg, 0.15 mmol) and $CoCl_2$ (155.8 mg, 1.2 mmol) in methanol (10 mL). After being stirred at room temperature for 26 hours, the reaction mixture was diluted with $CH_2Cl_2$. 3N HCl (~30 mL) was added and vigorously stirred until the black precipitate was completely dissolved. The aqueous layer was adjusted to pH=10 with concentrated $NH_4OH$, and then extracted with $CH_2Cl_2$. The combined $CH_2Cl_2$ phase was washed with brine, dried ($Na_2SO_4$), and concentrated to provide the known crude tetra-amine 45 (140.0 mg, 100%) as an off-white solid. Without further purification, this solid was brought to next step. $^1H$ NMR (500 MHz, $CDCl_3$) δ 6.77 (s, 8H), 4.37 (d, J=12.5 Hz, 4H), 3.87 (t, J=7.7 Hz, 8H), 3.12 (d, J=12.5 Hz, 4H), 2.79 (t, J=7.4 Hz, 8H), 2.02 (tt, J≈7.5, 7.5 Hz, 8H), 1.55 (tt, J=7.5, 7.5 Hz, 8H), 1.07 (s, 36H).

Example 39

Boc protected tetra-guanidine 31 and Boc protected tri-guanidine-mono-amine 44. To a solution of tetra-amine 45 (140.0 mg, 0.15 mmol) was added in sequence 1,3-bis(tert-butoxycarbonyl)-2-methyl-2-thiopseudourea (191.6 mg, 0.66 mmol), $HgCl_2$ (179.2 mg, 0.66 mmol), and $Et_3N$ (0.26 ml, 2.0 mmol). After being stirred for 15 hours the reaction mixture was filtered through Celite, and the filtrate was partitioned between $CH_2Cl_2$ and $NaHCO_3$ aqueous solution. The organic phase was dried ($Na_2SO_4$) and concentrated. Purification with MPLC (15% EtOAc in hexanes) provided Boc protected tetra-guanidine 31 (101.9 mg, 36%) and Boc protected tri-guanidine-mono-amine 44 (35.4 mg, 13%). For 31: $^1H$ NMR (500 MHz, $CDCl_3$) δ 11.51 (s, 4H), 8.38 (t, J=5.0 Hz, 4H), 6.75 (s, 8H), 4.33 (d, J=12.6 Hz, 4H), 3.90 (t, J=7.6 Hz, 8H), 3.48 (td, J=7.3, 5.0 Hz, 8H), 3.12 (d, J=12.6 Hz, 4H), 2.00 (m, 8H), 1.68 (m, 8H), 1.48$^+$ (s, 36H), 1.48$^-$ (s, 36H), 1.07 (s, 36H); $^{13}C$ NMR (75 MHz, $CDCl_3$) δ 163.8 (4C), 156.3 (4C), 153.5 (4C), 153.4 (4C), 144.6 (4C), 133.9 (8C), 125.1 (8C), 83.0 (4C), 79.2 (4C), 74.6 (4C), 41.1 (4C), 34.0 (4C), 31.6 (12C), 31.4 (4C), 28.5 (12C), 28.3 (12C), 27.7 (4C), 25.9 (4C); HRMS (ESI) m/z calcd for $C_{104}H_{165}N_{12}NaO_{20}$ $(M+H+Na)^{2+}$ 962.6080. found 962.6090. For 44: $^1H$ NMR (500 MHz, $CDCl_3$) δ 11.52 (s, 3H), 8.39 (m, 3H), 6.79 (s, 4H), 6.74 (s, 4H), 5.25 (m, 1H), 4.34 (d, J=12.5 Hz, 2H), 4.33 (d, J=12.5 Hz, 2H), 3.88 (m, 8H), 3.48 (m, 6H), 3.21 (m, 2H), 3.12$^+$ (d, J=12.5 Hz, 2H), 3.12$^-$ (d, J=12.5 Hz, 2H), 2.01 (m, 8H), 1.69 (m, 8H), 1.48 (s, 54H), 1.41 (s, 9H), 1.09 (s, 18H), 1.05 (s, 18H); $^{13}C$ NMR (75 MHz, $CDCl_3$) 163.8 (3C), 156.3 (4C), 153.7 (1C), 153.4$^+$ (4C), 153.4$^-$ (2C), 144.6$^+$ (1C), 144.6 (1C), 144.5 (2C), 134.0 (4C), 133.8 (2C), 133.7 (2C), 125.1 (8C), 83.1 (4C), 79.3 (3C), 74.7 (4C), 41.2 (1C), 41.1 (3C), 34.0$^+$ (2C), 34.0$^-$ (2C), 31.7 (6C), 31.6 (6C), 31.5 (2C), 31.4 (2C), 28.6 (3C), 28.5 (9C), 28.3 (9C), 27.8 (4C), 26.0 (3C), 25.9 (1C); HRMS (ESI) m/z calcd for $C_{98}H_{154}N_{10}O_{18}Na_2$ $(M+2Na)^{2+}$ 902.5619. found 902.5723.

Example 40

5,11,17,23-Tetra-tert-butyl-25,26,27,28-tetrakis(4-guanidinobutoxy)calix[4]arene trifloroacetic acid salt 42. Tetra-guanidine 31 (101.9 mg, 0.05 mmol) was dissolved in a solution of $CH_2Cl_2$ with 40% TFA and 5% anisole (1.0 mL) and the mixture was stirred at room temperature for 3 hours. The volatile components were removed under vacuo. The residue was partitioned between $CH_2Cl_2$ and water and the aqueous phase was adjusted to pH=8 with $NaHCO_3$ aqueous solution. The organic phase was separated, dried ($Na_2SO_4$), and concentrated to give the calixarene 42•TFA salt (104.5 mg, 98% assuming an octatrifluoroacetate salt) as an off-white solid. $^1H$ NMR (500 MHz, $CD_3OD$) δ 6.81 (s, 8H), 4.42 (d, J=12.8 Hz, 4H), 3.96 (t, J=7.2 Hz, 8H), 3.29 (m, 8H), 3.15 (d, J=12.8 Hz, 4H), 2.08 (m, 8H), 1.79 (m, 8H), 1.08 (s, 36H); HRMS (ESI) m/z calcd for $C_{64}H_{102}N_{12}O_4$ $(M+2H)^{2+}$ 551.4073. found 551.4107.

Example 41

5,11,17,23-Tetra-tert-butyl-25,26,27-tris(4-guanidinobutyroxy)-28-(4-aminobutyroxy)calix[4]arene trifloroacetic acid salt 43. According to the procedure described for tetra-guanidine 42, the Boc protected mono-amino-tri-guanidine 44 (34.5 mg, 0.02 mmol) in 5% anisole $CH_2Cl_2$ solution (0.6 mL) was treated TFA (0.4 mL) at room temperature. Standard workup and purification gave rise to the calixarene 43•TFA salt (30.4 mg, 82% assuming an heptatrifluoroacetate salt). $^1H$ NMR (500 MHz, $CD_3OD$) δ 6.97 (s, 4H), 6.67 (s, 4H), 4.42$^+$ (d, J=12.4 Hz, 2H), 4.42$^-$ (d, J=12.4 Hz, 2H), 4.07 (t, J=8.0 Hz, 2H), 3.91 (m, 6H), 3.28 (m, 8H), 3.15 (d, J=12.4 Hz, 2H), 3.13 (d, J=12.4 Hz, 2H), 2.17 (m, 2H), 2.02 (m, 6H), 1.77 (m, 6H), 1.66 (m, 2H), 1.20$^+$ (s, 9H), 1.20$^-$ (s, 9H), 0.97 (s, 18H); $^{13}C$ NMR (75 MHz, $CDCl_3$ and $CD_3OD$) 157.4 (3C), 153.5 (2C), 153.3 (1C), 153.2 (1C), 144.6$^+$ (3C), 144.6$^-$ (1C), 133.7$^+$ (2C), 133.7$^-$ (2C), 133.4 (4C), 125.1 (4C), 125.0 (4C), 74.6 (4C), 41.8 (1C), 41.5 (3C), 33.8$^+$ (2C), 33.8$^-$ (2C), 31.4$^+$ (6C), 31.4$^-$ (6C), 31.2 (4C), 27.8$^+$ (2C), 27.8$^-$ (2C), 25.9 (4C); HRMS (ESI) m/z calcd for $C_{63}H_{100}N_{10}O_4$ $(M+2H)^{2+}$ 530.3964. found 530.4001.

Example 42

O-Propargyl-4-tert-butyl calix[4]arene 51a and 51b. A suspension of 4-tert-butyl calix[4]arene (649.0 mg, 1.0 mmol) in THF and DMF (15 mL, 10:1) was treated with NaH (192.0 mg, 8.0 mmol) and propargyl bromide (80% in toluene, 2.23 mL, 20 mmol). The reaction mixture was refluxed for 18 hours and cooled to room temperature. After filtration through Celite, the filtrate was diluted with $CH_2Cl_2$, washed with brine, dried ($Na_2SO_4$) and concentrated. The residue was first purified by flash chromatography (3% EtOAc in hexanes) to give cone conformer 51a (255.9 mg). The components with cone conformer 51a and partial cone analog 51b as a mixture was further purified by MPLC to give more compound 51a (146.3 mg, 50% in total) and compound 51b (297.3 mg, 37%). For 51a, $^1$H NMR (300 MHz, $CDCl_3$) δ 6.79 (s, 8H), 4.80 (d, J=2.3 Hz, 8H), 4.60 (d, J=12.9 Hz, 4H), 3.16 (d, J=12.9 Hz, 4H), 2.47 (t, J=2.3 Hz, 4H), 1.07 (s, 36H); $^{13}$C NMR (75 MHz) δ 152.6 (4C), 145.7 (4C), 134.5 (8C), 125.2 (8C), 81.4 (4C), 74.5 (4C), 61.2 (4C), 34.1 (4C), 32.6 (4C), 31.6 (12C); HRMS (ESI) m/z calcd for $C_{56}H_{64}Na_1O_4$ $(M+Na)^+$ 823.4702. found 823.4725. For 51b, $^1$H NMR (300 MHz, $CDCl_3$) δ 7.43 (s, 2H), 7.06 (s, 2H), 6.99 (d, J=2.5 Hz, 2H), 6.52 (d, J=2.5 Hz, 2H), 4.48 (dd, J=15.3, 2.5 Hz, 2H), 4.44 (dd, J=15.3, 2.5 Hz, 2H), 4.35 (d, J=2.5 Hz, 2H), 4.31 (d, J=13.0 Hz, 2H), 4.24 (d, J=2.5 Hz, 2H), 3.85 (d, J=14.0 Hz, 2H), 3.73 (d, J=14.0 Hz, 2H), 3.08 (d, J=13.0 Hz, 2H), 2.50 (t, J=2.3, 2H), 2.44 (t, J=2.5 Hz, 1H), 2.24 (t, J=2.5 Hz, 1H), 1.45 (s, 9H), 1.33 (s, 9H), 1.04 (s, 18H); $^{13}$C NMR (75 MHz) δ 154.3 (1C), 153.3 (2C), 151.8 (1C), 146.1 (1C), 145.2 (2C), 144.3 (1C), 136.5 (2C), 133.1 (2C), 132.5 (2C), 132.1 (2C), 128.8 (2C), 126.3 (2C), 125.7 (2C), 125.6 (2C), 82.2 (1C), 81.2 (2C), 80.9 (1C), 74.7 (2C), 74.5 (1C), 73.9 (1C), 61.0 (2C), 59.3 (1C), 58.8 (1C), 37.9 (2C), 34.3 (2C), 34.0 (2C), 32.6 (2C), 32.0 (3C), 31.8 (3C), 31.6 (6C).

Example 43

1,2,3-Triazole derivative of calix[4]arene 52a. Water (0.4 mL) was added to the solution of alkyne 52a (80.1 mg, 0.1 mmol) and N-Boc-2-azido-ethylamine (149.0 mg, 0.8 mmol) in tBuOH (0.4 mL) and THF (0.2 mL). The reaction mixture turned cloudy, and then ascorbic acid (7.0 mg, 0.04 mmol), NaOAc (6.6 mg, 0.08 mmol), and $CuSO_4 \cdot 5H_2O$ (5.0 mg, 0.02 mmol) was added to the suspension. The reaction mixture was stirred at room temperature for 36 hrs. $NH_4Cl$ aqueous solution (3 mL) was added to stop the reaction. After stirred for 5 min, the reaction mixture was extracted by $CH_2Cl_2$. The combined organic phase was dried ($Na_2SO_4$) and concentrated. The residue was purified by flash chromatography (4% MeOH in $CH_2Cl_2$) to give the tetra-triazole 52a (75.7 mg, 50%) as a light yellow solid. $^1$H NMR (300 MHz, $CDCl_3$, 55° C.) δ 7.81 (br s, 4H), 6.77 (s, 8H), 5.68 (br s, 4H), 5.00 (br s, 8H), 4.45 (br m, 8H), 4.32 (d, J=12.8 Hz, 4H), 3.55 (br m, 8H), 3.09 (d, J=12.8 Hz, 4H), 1.42 (s, 36H), 1.08 (br s, 36H) $^{13}$C NMR (75 MHz, $CDCl_3$) δ 156.3 (4C), 152.6 (4C), 145.4 (4C), 144.7 (4C), 134.0 (8C), 125.3 (8C), 124.8 (4C), 79.7 (4C), 67.2 (4C), 49.9 (4C), 40.9 (4C), 34.0 (4C), 31.5 (16C), 28.6 (12C); HRMS (ESI) m/z calcd for $C_{84}H_{120}N_{16}Na_2O_{12}$ $(M+2Na)^{2+}$ 795.4534. found 795.4567.

Example 44

1,2,3-Triazole derivative of calix[4]arene 52b. According to the procedure described for tetra-triazole 52b, alkyne 52a (58.6 mg, 0.07 mmol) and N-Boc-2-azido-ethylamine (114.3 mg, 0.58 mmol) in tBuOH (0.3 mL), THF (0.2 mL), and water (0.4 mL) were treated with ascorbic acid (5.1 mg, 0.03 mmol), NaOAc (4.8 mg, 0.06 mmol), and $CuSO_4 \cdot 5H_2O$ (3.6 mg, 0.01 mmol). The reaction mixture was stirred for 36 hrs. Standard workup and purification as described for tetra-triazole 52a gave the tetra-triazole 52b (80.0 mg, 88%) in partial cone conformation as a light yellow solid. $^1$H NMR (300 MHz, $CD_3Cl$) 8.04 (br s, 2H), 7.49 (br s, 2H), 7.13 (s, 2H), 6.92 (s, 2H), 6.86 (d, J=2.0 Hz, 2H), 6.42 (d, J=2.0 Hz, 2H), 5.19 (br s, 2H), 4.99$^+$ (d, J=11.0 Hz, 2H), 4.99$^-$ (br s, 1H), 4.93 (br s, 1H), 4.88 (s, 2H), 4.74 (d, J=11.0 Hz, 2H), 4.73 (s, 2H), 4.44 (m, 6H), 4.35 (br m, 2H), 4.09 (d, J=13.2 Hz, 2H), 3.79 (d, J=13.8 Hz, 2H), 3.72 (d. J=13.8 Hz, 2H), 3.67 (br m, 2H), 3.59 (m, 4H), 3.35 (br m, 2H), 2.95 (d, J=13.2 Hz, 2H), 1.45+ (s, 9H), 1.45− (s, 9H), 1.43 (s, 18H), 1.25 (s, 9H), 0.95 (s, 9H), 0.92 (s, 18H); $^{13}$C NMR (75 MHz) δ 156.1 (1C), 156.0 (3C), 154.3 (1C), 153.4 (2C), 151.0 (1C), 145.3 (1C), 144.7 (3C), 144.6 (2C), 144.2 (1C), 143.4 (1C), 136.6 (2C), 133.0 (2C), 132.2 (2C), 132.1 (2C), 128.6 (2C), 126.2 (2C), 125.3 (3C), 125.0 (1C), 124.8 (2C), 124.2 (2C), 80.2 (1C), 80.0 (2C), 79.9 (1C), 67.0 (2C), 65.1 (1C), 62.3 (1C), 50.2 (3C), 49.9 (1C), 41.1 (1C), 40.6 (2C), 40.5 (1C), 37.4 (2C), 34.2 (1C), 33.8 (2C), 33.7 (1C), 32.2 (2C), 31.7 (3C), 31.4 (6C), 31.3 (3C), 28.6 (3C), 28.5 (9C); HRMS (ESI) m/z calcd for $C_{84}H_{120}N_{16}Na_2O_{12}$ $(M+2Na)^{2+}$ 795.4534. found 795.4547.

Example 45

Aminoethyl triazole derivative of calix[4]arene 46a. Tetra-triazole 52a (30.9 mg, 0.02 mmol) was dissolved in a solution of $CH_2Cl_2$ with 5% anisole (0.6 mL), and then cooled to 0° C. TFA (0.4 mL) was added dropwise and the reaction mixture was allowed warm to room temperature. After 3 hours, the reaction mixture was concentrated under vacuo. The residue was triturated in ether to give aminoethyl triazole 46a•TFA salt (24.8 mg, 77% assuming an tetratrifluoroacetate) as a white solid. $^1$H NMR (500 MHz, $CD_3OD$) 8.08 (s, 4H), 6.83 (s, 8H), 5.05 (s, 8H), 4.81 (t, J=6.0 Hz, 8H), 4.15 (d, J=12.7 Hz, 4H), 3.58 (t, J=6.0 Hz, 8H), 2.97 (d, J=12.7 Hz, 4H), 1.09 (s, 36H); $^{13}$C NMR (75 MHz) δ 153.7 (4C), 146.7 (4C), 146.3 (4C), 135.4 (8C), 127.0 (4C), 126.6 (8C), 67.8 (4C), 48.6 (4C), 40.5 (4C), 35.0 (4C), 32.7 (4C), 32.1 (12C); HRMS (ESI) m/z calcd for $C_{64}H_{89}N_{16}O_4$ $(M+H)^+$ 1145.7247. found 1145.7275.

Example 46

Aminoethyl triazole derivative of calix[4]arene 46b. According to the procedure described for aminoethyl triazole 46a, tetra-triazole 52b (50.8 mg, 0.03 mmol) in a solution of $CH_2Cl_2$ with 5% anisole (0.6 mL) was treated with TFA (0.4 mL). After 3 hour, the reaction mixture was concentrated under vacuo. The residue was triturated in ether to give aminoethyl triazole 46b•TFA salt (55.8 mg, 100% assuming an tetratrifluoroacetate) in partial cone conformation as a white solid. $^1$H NMR (300 MHz, $CD_3OD$) 8.28 (s, 2H), 8.22 (s, 1H), 8.16 (s, 1H), 7.18 (s, 2H), 6.95 (s, 2H), 6.94 (d. J=2.4 Hz, 2H), 6.42 (d, J=2.4 Hz, 2H), 4.93 (d, J=11.6 Hz, 2H), 4.90 (s, 4H), 4.84 (d, J=11.6 Hz, 2H), 4.74 (m, 8H), 3.96 (d, J=12.9 Hz, 2H), 3.81 (br s, 4H), 3.54 (m, 8H), 2.85 (d, J=12.9 Hz, 2H), 1.27 (s, 9H), 1.01 (s, 9H), 0.91 (s, 18H); $^{13}$C NMR (75 MHz) δ 156.0 (1C), 154.7 (2C), 152.3 (1C), 146.6 (1C), 146.1 (2C), 146.0 (2C), 145.8 (2C), 144.5 (1C), 137.7 (2C), 134.3 (2C), 133.4 (4C), 129.8 (2C), 127.8 (2C), 127.5 (1C), 127.2 (2C), 127.1 (1C), 126.8 (2C), 126.4 (2C), 67.5 (2C), 65.9 (1C), 63.5 (1C), 48.9 (1C), 48.4 (2C), 48.2 (1C), 40.4 (4C), 38.0 (2C), 35.0 (1C), 34.8+ (2C), 34.8− (1C), 33.2 (2C), 32.2 (3C), 32.1 (6C), 32.0 (3C); HRMS (ESI) m/z calcd for $C_{64}H_{90}N_{16}O_4$ $(M+2H)^{2+}$ 573.3660. found 573.3675.

Example 47

NMR Data from Spectroscopic Characterization of Additional Calixarene Derivatives Tetra-amine 41: $^1$NMR (500 MHz, CDCl$_3$) δ 7.94 (br t, J=6.5 Hz, 2H), 7.33 (br t, J=6.5 Hz, 2H), 6.73 (s, 4H), 6.17 (s, 4H), 5.65 (ddt, J=17.1, 10.5, 6.8 Hz, 2H), 4.91 (dd, J=10.5, 1.4 Hz, 2H), 4.85 (dd, J=17.1, 1.4 Hz, 2H), 4.80 (s, 2H), 4.65 (s, 2H), 4.61 (s, 4H), 4.45 (d, J=13.5 Hz, 4H), 4.33 (s, 4H), 3.50 (dt, J≈6, 6 Hz, 4H), 3.37 (dt, J≈6, 6 Hz, 4H), 3.17 (d, J=14.7 Hz, 4H), 3.16 (s, 4H), 2.86 (d, J=6.8 Hz, 4H), 2.52 (t, J=6.4 Hz, 4H), 2.40 (t, J=6.4 Hz, 4H), 2.24 (s, 12H), 2.19 (s, 12H), 1.68 (s, 6H); $^{13}$C NMR (125 MHz, CDCl$_3$) δ 170.2 (2C), 169.5 (2C), 154.9 (2C), 153.4 (2C), 145.9 (2C), 137.8 (2C), 134.9 (4C), 134.4 (2C), 134.3 (2C), 132.9 (4C), 130.1 (4C), 128.5 (4C), 115.4 (2C), 111.6 (2C), 74.7 (2C), 74.2 (2C), 58.3 (2C), 58.1 (2C), 45.5 (4C), 45.4 (4C), 44.1 (2C), 39.6 (2C), 37.1 (2C), 37.1 (2C), 31.3 (4C), 22.3 (2C); HRMS (ESI) m/z calcd for C$_{66}$H$_{93}$N$_8$O$_8$ (M+H)$^+$ 1125.7116. found 1125.7213.

5,17-Di-(hydroxycarbonyl)ethyl-25,27-di-(3-methylbutoxy)-26,28-dihydroxycalix[4]arene 47: $^1$H NMR (300 MHz, CD$_3$OD) δ 6.96 (d, J=7.2 Hz, 4H), 6.95 (s, 4H), 6.75 (t, J=7.2 Hz, 2H), 4.27 (d, J=13.0 Hz, 4H), 4.01 (t, J=6.7 Hz, 4H), 3.37 (d, J=13.0, 4H), 2.77 (t, J=7.6 Hz, 4H), 2.52 (t, J=7.6 Hz, 4H), 2.18 (tqq, J≈7, 7, 7 Hz, 2H), 1.97 (dt, J≈7, 7 Hz, 4H), 1.11 (d, J=6.6 Hz, 12H); $^{13}$C NMR (125 MHz, CD$_3$OD) δ 177.3 (2C), 153.6 (2C), 152.7 (2C), 135.1 (4C), 132.7 (2C), 130.1 (4C), 129.6 (4C), 129.5 (4C), 126.3 (2C), 76.5 (2C), 40.3 (2C), 37.5 (2C), 32.3 (4C), 31.5 (2C), 26.1 (2C), 23.4 (4C); HRMS (ESI) m/z calcd for C$_{44}$H$_{51}$O$_8$ (M−H)$^-$ 707.3589. found 707.3568.

Di-phosphonic acid 48: $^1$H NMR (500 MHz, CD$_3$OD) δ 6.96 (d, J=7.8 Hz, 4H), 6.93 (s, 4H), 6.76 (t, J=7.8 Hz, 2H), 4.29 (d, J=12.6 Hz, 4H), 4.03 (t, J=6.9 Hz, 4H), 3.38 (d, J=12.6 Hz, 4H), 2.57 (t, J=7.0 Hz, 4H), 2.19 (tqq, J≈7, 6, 6 Hz, 2H), 1.98 (dt, J≈7, 7 Hz, 4H), 1.84 (nfom, 4H), 1.61 (nfom including JPH=18.0 Hz, 4H), 1.12 (d, J=6.5 Hz, 12H); $^{13}$C NMR (125 MHz, CD$_3$OD) δ 153.4 (2C), 152.4 (2C), 135.0 (4C), 133.1 (2C), 129.9 (4C), 129.6 (4C), 129.4 (2C), 126.2 (2C), 76.4 (2C), 40.1 (2C), 36.6 (d, JCP=17.1 Hz, 2C), 32.2 (6C), 27.3 (d, JCP=137.9 Hz, 2C), 26.0 (2C), 23.4 (4C); $^{31}$P (121 MHz, CD$_3$OD) δ 31.0; HRMS (ESI) m/z calcd for C$_{44}$H$_{56}$O$_{10}$P$_2$ (M−2H)$^{2-}$ 403.1680. found 403.1682.

Bis-sulfonate 49: $^1$H NMR (500 MHz, CD$_3$OD) δ 6.96 (d, J=7.5 Hz, 4H), 6.95 (s, 4H), 6.76 (t, J=7.5 Hz, 2H), 4.27 (d, J=12.8 Hz, 4H), 4.02 (t, J=6.8 Hz, 4H), 3.98 (t, J=6.4 Hz, 4H), 3.36 (d, J=12.8 Hz, 4H), 2.58 (t, J=7.6 Hz, 4H), 2.18 (tqq, J≈7, 6, 6 Hz, 2H), 1.97 (td, J≈7, 7 Hz, 4H), 1.89 (tt, J≈7, 6 Hz, 4H), 1.11 (d, J=6.2 Hz, 12H); $^{13}$C NMR (75 MHz, CDCl$_3$) δ 153.6 (2C), 152.5 (2C), 135.2 (4C), 133.4 (2C), 130.1 (4C), 129.8 (4C), 129.5 (4C), 126.3 (2C), 76.4 (2C), 68.5 (2C), 40.4 (2C), 32.8 (2C), 32.3 (4C), 32.2 (2C), 26.1 (2C), 23.5 (4C); HRMS (ESI) m/z calcd for C$_{44}$H$_{54}$O$_{12}$S$_2$ (M−2Na)$^{2-}$ 419.1534. found 419.1524.

Example 48

Antitumor and Other Effects of Calixarene-Based Peptide Mimetics

This example demonstrates that non-peptidic, calixarene-scaffolded compounds that capture the amphipathic surface topology common to bactericidal, LPS binding are biologically active in vitro and in vivo. Members of the library of prepared compounds were shown to neutralize LPS from multiple species of Gram negative bacteria and promote survival of mice challenged with LPS and inhibit angiogeniesis and tumor growth in mice.

Experimental

Peptide Synthesis.

βpep-25 peptide was synthesized using a Milligen/Biosearch 9600 peptide solid-phase synthesizer using fluorenylmethoxycarbonyl (Fmoc) chemistry and purified as previously reported (Mayo et al., Journal of Biological Chemistry 278, 45746-52 (2003)). The amino acid sequences of peptides were confirmed by N-terminal sequencing and mass spectrometry.

LPS Neutralization Assay.

The ability of compounds to neutralize endotoxin was detected in vitro by using the chromogenic QCL-1000 kit from BioWhittaker, Inc. (Walkersville, Md.), and as described in their protocol. This *Limulus* amoebocyte lysate (LAL) assay is quantitative for Gram negative bacterial endotoxin (lipopolysaccharide, LPS). In this assay compounds that are active inhibit the LPS-mediated activation of a proenzyme whose active form would release p-nitroaniline (pNA) from a colorless synthetic substrate, producing a yellow color (pNA) whose absorption is monitored spectrophotometrically at 405-410 nm. The initial rate of enzyme activation is proportional to the concentration of endotoxin present.

Variants of LPS from six Gram negative bacteria were used: *E. coli* serotypes 0111:B4 (Combrex, Walkersville, Md.) and 055:B5 (Sigma, St. Louis, Mo.); *Klebsiella pneumoniae* (List Biologics, San Jose, Calif.); *Pseudomonas aeruginosa* (List Biologics, San Jose, Calif.); *Salmonella typhimurium* (List Biologics, San Jose, Calif.), and *Serratia marcascens* (List Biologics, San Jose, Calif.). The concentration of compound required to neutralize a given LPS and therefore to inhibit the *Limulus* amoebocyte lysate driven by 0.04 units of any given LPS was determined by dose response curves fit by using a standard sigmoidal function to determined the IC$_{50}$ value for each topomimetic compound. The 0.04 units corresponds to 0.01 ng LPS from *E. coli* serotype 055:B5, 0.01 ng LPS from *E. coli* serotype 0111:B4, 0.003 ng LPS from *K. pneumoniae*, 0.01 ng LPS from *P. aeruginosa*, 0.03 ng LPS from *S. typhimurium*, and 0.03 ng LPS from *S. marcascens*.

In three separate studies, these compounds were tested against LPS derived from *E. coli* serotype 0111:B4, *E. coli* serotype 055:B5 LPS, and *Salmonella*. The compounds (in a final concentration of 2% DMSO v/v), were first mixed individually with LPS, and incubated for 30 minutes prior to i.p. injection into C57/BL6 mice (n=4-8/group). The control mice were treated with DMSO (2% v/v) alone. Each mouse received a lethal dose of LPS, with or without one of the compounds.

Endotoxemia Studies in Mice.

C57 male black mice were injected i.p. with a solution that contained a lethal close of LPS [600 μg of LPS from *E. coli* 055:B5 and *Salmonella*, and 500 μg of LPS from *E. coli* 011:B4] and 1.25 mg of the topomimetic compound (a dose of 50 mg/kg) (Rifkind, D. J Bacteriol 93, 1463-4 (1967)). Mice were provided food and water as usual ad libitum, and monitored for several days. When it was observed that mice were in distress and death was imminent, animals were sacrificed; in some cases, mice expired during the night and were found dead the following morning. Data are plotted as the number of surviving mice versus time in hours. Statistical analysis was performed on the average amount of survival time per group with a maximum of 120 hours (surviving mice) by using the Student's t-test.

Cell Proliferation.

EC proliferation was measured using a [$^3$H]-thymidine incorporation assay. Proliferation of bFGF-stimulated (10 ng/ml) human umbilical vascular EC (HUVEC) cultures was measured by quantification of $^3$H-thymidine incorporation. Proliferation is expressed as mean counts per minute (cpm) of quadruplicate cultures in three independent experiments (±SEM). EC were seeded at 5000 cells/well in flat-bottomed tissue culture plates and grown for 3 days in the absence or presence of regulators, in culture medium. During the last 6 hours of the assay, the culture was pulsed with 0.5 μCi [methyl-$^3$H]-thymidine/well. Human umbilical vein derived EC (HUVEC) were harvested from normal human umbilical cords by perfusion with 0.125% trypsin/EDTA. Harvested HUVECs were cultured in gelatin coated tissue culture flasks and subcultured 1:3 once a week in culture medium (RPMI-1640 with 20% human serum (HS), supplemented with 2 mM glutamine and 100 U/mL penicillin and 0.1 mg/mL streptomycin). Statistical analysis was performed by using the Student's t-test.

Endothelial Cell Migration.

EC migration was measured in the wound healing assay. HUVEC were cultured in triplicate on a 1-mg/ml fibronectin coat in a 24-well tissue culture plate. Cells were grown for 3 days until confluence. When confluent, a wound was made in the well, using a blunt glass pipette. The medium was replaced with medium containing 10 ng/ml bFGF with or without 25 μM compound and at 0, 2, 4, 6, and 8 hours, the wound width was measured at four different predefined places. Photographs were made using an inverted microscope and a Contax 167 MT 35 mm camera.

Chorioallantoic Membrane (CAM) Assay.

Fertilized Lohman-selected white leghorn eggs were incubated for 3 days at 37° C. and 55% relative humidity and rotated once every hour. On day 3 a rectangular window (1 cm×2 cm) was made in the eggshell. The window was covered with tape to prevent dehydration. The window allowed undisturbed observation of the developing vasculature of the CAM. On day 7 a silicon ring (10 mm diameter) was placed on the CAM to allow local drug administration within the ring. Compounds were applied daily in aliquots of 65 μl (25 μM) from day 10 to day 13. On day 14 the CAMs were photographed.

Tumor Model Studies in Mice.

Female athymic nude mice (nu/nu, 5-6 weeks old) or C57BL/6 male mice were purchased from the National Cancer Institute and allowed to acclimatize to local conditions for at least one week. Animals were provided water and standard chow ad libitum, and were kept on a 12 hour light/dark cycle. All experiments followed protocols approved by the University of Minnesota Research Animal Resources Ethical Committee. Exponentially growing MA148 human ovarian carcinoma cells, kindly provided by Prof. Ramakrishnan (Dings et al., Cancer Res 63, 382-385 (2003)), and B16F10 murine melanoma cells, kindly provided by Prof. Fidler, were cultured in RPMI 1640 medium (Life Technologies, Grand Island, N.Y.) (van der Schaft, et al., Faseb J 16, 1991-1993 (2002)). This medium was supplemented with 10% fetal bovine serum and 1% penicillin/streptomycin (Cellgro, Mediatech, Washington, D.C.) at 37° C. and 5% $CO_2$. 100 μL of this tumor cell suspension (2×10$^7$ MA148 cells/ml and 2×10$^6$ B16F10 cells/ml) was then injected subcutaneously into the right hind flank of each mouse (athymic or C57BL/6, respectively).

Tumors were allowed to grow to an average size of at least 50 mm$^3$ before treatment was initiated, and animals were randomized prior to the initiation of treatment. Treatment was administered in one of two ways: s.c. from osmotic mini-pumps, and i.p. injection. Osmotic mini-pumps (Durect, Cupertino, Calif.) were implanted subcutaneously in the left flank of mice, and concentrated solutions of calixarene analogs or βpep-25 were formulated in PBS containing 30% (v/v) DMSO such that the 14-day or 28-day treatment period would be covered by implantation of a single pump. In each study, control groups of animals were administered either PBS (30% DMSO v/v) or PBS containing human serum albumin to control for protein content. Tumor growth curves were found to be identical in either of these control cases.

Tumor volume was determined by measuring the diameters of tumors using calipers (Scienceware, Pequannock, N.J.) using the equation for the volume of a spheroid: ($a^2$×b× II)/6, where 'a' is the width and 'b' the length of the tumor. Measurements were performed two or three times per week. At the conclusion of an experiment, tumor weights were also taken following excision of the tumors from euthanized animals. Tumor weights correlated well with tumor volumes calculated in this way. Statistical differences in tumor growth curves were analyzed using the two-way ANOVA test.

Immunohistochemistry.

Immunohistochemistry was used to assess microvessel density and the extent of total cell apoptosis. Approximately, tumors of the same size and with no apparent necrosis were selected for processing. On the last day of treatment mice were sacrificed and tumors were excised. Tumor tissue was embedded in tissue freezing medium (Miles Inc, Elkart, Ind.) and shock frozen in liquid nitrogen. Sections of tissue (10 μm thickness) were prepared for immunohistochemical analysis. For this, tissue sections were brought to room temperature, air dried overnight, and then fixed in acetone for 10 minutes. Slides were allowed to air dry for at least 30 minutes and were washed three times for 5 minutes each in phosphate-buffered saline (PBS, pH 7.4). Samples were then blocked with PBS containing 0.1% bovine serum albumin and 3% human serum albumin for at least 30 minutes at room temperature in a humidified box. Samples were subsequently incubated with phycoerythrin (PE)-conjugated monoclonal antibody to CD31 (PECAM-1) in a 1:50 dilution (Pharmigen, San Diego, Calif.) to stain for microvessel density.

To assess the extent of total cell apoptosis, tumor tissue sections were stained by using the TUNEL (terminal deoxyribonucleotidyl transferase-mediated dUTP-nick-end labeling) assay, which was performed according to the manufacturer's instructions (In situ cell death detection kit, fluorescein; TUNEL, Roche). After 1-hour incubation at room temperature, slides were washed with PBS and immediately imaged using an Olympus BX-60 fluorescence microscope at 200× magnification.

Digital images were stored and processed using Adobe Photoshop (Adobe Inc., Mountain View Calif.). Quantification of microvessel density, were determined as described previously (Dings et al., Cancer Res 63, 382-385 (2003)). Statistical analysis was performed using the Student's t-test.

Toxicity Assays.

As an indirect measurement of general toxicity, body weights of mice were monitored twice weekly, using a digital balance (Ohaus Florham, N.J.). To determine hematocrit levels, blood samples were extracted by tail veil bleedings one day after terminating treatment, and blood was collected in heparinized micro-hematocrit capillary tubes (Fisher; Pittsburgh, Pa.). Samples were spun down for 10 minutes in a micro-hematocrit centrifuge (Clay-Adams; N.Y.), and the amount of hematocrit was determined using an international microcapillary reader (IEC; Needham. Mass.).

Results

Design of Helix/Sheet Topomimetics.

The design of helix/sheet topomimetics was based on the folded structures of two peptides: SC4 (Mayo et al. Biochem J 349 Pt 3, 717-28. (2000)) and βpep-25 (Griffioen et al, Biochem J 354, 233-42 (2001)). SC4 is a helix-forming peptide 12 mer that primarily is bactericidal and binds to and neutralizes LPS and βpep-25 is a β-sheet forming peptide 33 mer that is antiangiogenic and specifically targets an adhesion/migration receptor on angiogenically-activated endothelial cells (EC). In mouse models, βpep-25 effectively inhibits tumor angiogenesis and tumor growth. Like most anti-angiogenic agents, βpep-25 is also bactericidal and can bind to and neutralize LPS. SC4, which is derived from βpep-25, captures most of βpep-25's bactericidal and LPS binding activities.

Representative structures of both SC4 and βpep-25 are illustrated in FIG. 1, with their hydrophobic and hydrophilic surfaces highlighted. Functionally key amino acids in βpep-25 are contained within the mid-segment of its sheet, about 4 residues long on each β-strand (Mayo et al., Journal of Biological Chemistry 278, 45746-52 (2003)). This translates dimensionally into a unit about 9 Å from $C_\alpha(i)$ to $C_\alpha(i+3)$ along the β-strand, and about 5 Å cross-strand from $C_\beta$ to $C_\beta$. The thickness of a β-strand from one $C_\beta(i)$ to the next $C_\beta(i+1)$ is also about 5 Å. These dimensions are approximately the same for about two turns of the SC4 α-helix, i.e. a cylinder about 5 Å in backbone diameter and 8 Å along the axis. In either case, these backbone dimensions are well approximated by the calix[4]arene scaffold, as illustrated to scale in the upper middle of FIG. 1.

Adding various chemical groups (hydrophobic aliphatic groups and hydrophilic cationic groups) onto this calixarene scaffold produces compounds that approximate the molecular dimensions, surface topology and polarity of segments of β-sheet and α-helix as in βpep-25 and SC4, respectively. A library of 23 calixarene-based compounds was synthesized, and their structures are provided in FIG. 2. Exemplary chemical reactions used to synthesize these calix[4]arene analogs are illustrated in Schemes 7a-c, which provide representative methods for preparation of several of the most active calixarene derivatives. Scheme 7(a) shows the synthesis of tertiary amine calixarene derivatives 40 and 12. Scheme 7(b) synthesis of guanidine calixarene derivatives 42 and 43 and primary amine calixarene derivative 45. Scheme 7(c) shows the synthesis of triazole linked primary amine calixarene derivatives 46a and 46b. The reaction conditions referred to by letters in the scheme are: a) $AlCl_3$, PhOH, toluene, room temperature (rt); b) ethyl bromoacetate, $K_2CO_3$, acetone, reflux; c) N,N-dimethylethylenediamine, toluene, reflux; d) i. NaH, methylallylchloride, THF, DMF, 80° C.; ii. N,N-dimethylaniline, 200° C.; e) Pd/C, $H_2$, 1 atmosphere (atm), EtOAc, rt; f) 4-bromobutyronitrile, $K_2CO_3$, acetone, reflux; g) 4-bromobutyronitrile, NaH, DMF, 75° C.; h) $NaBH_4$, $CoCl_2$, MeOH; i) 1,3-bis(tert-butoxycarbonyl)-2-methyl-2-thiopseudourea, $HgCl_2$, $Et_3N$, $CH_2Cl_2$; j) TFA, 5% anisole in $CH_2Cl_2$, rt; k) NaH, propargyl bromide, THF, DMF, reflux; l) ascorbic acid, NaOAc, $CuSO_4$, t-BuOH, $H_2O$, THF; m) TFA, 5% anisole in $CH_2Cl_2$, 0° C. to rt.

Most compounds shown in FIG. 2 have short chain aliphatic (primarily iso-butyl and tert-butyl) groups on their hydrophobic face, and a more varied hydrophilic face displaying primary and tertiary amines, triazole and guanidinium groups, or in some cases negatively charged groups as negative controls.

Helix/Sheet Topomimetics Neutralize LPS.

Initially, the library was screened for bactericidal activity against *Pseudomonas aeruginosa*, the Gram negative bacterium against which SC4 and βpep-25 were most effective, but found that only a few compounds had merely modest activity ($LD_{50}$ values) in the 10 micromolar range. However, using the LPS neutralization assay, it was demonstrated that several members from the topomimetic library were highly effective at binding to and neutralizing LPS from six species of bacteria. $IC_{50}$ values determined from dose response curves for all analogs are listed in Table 3. Although many compounds have $IC_{50}$ values in the single-digit micromolar range, several fall in the sub-micromolar range, and a few are active in the 5 to 50 nanomolar range. The best LPS neutralizing compounds are 12, 42, 43, 15, 46a, and 19. $IC_{50}$ values in the 5 nM to 50 nM range are exceptional, not only because this level of activity is better than that for SC4 and βpep-25, but because it is on par with the 55 kiloDalton LPS binding protein bactericidal/permeability increasing factor and polymyxin B (see Table 3).

TABLE 3

Calixarene Derivatives. $IC_{50}$ values (μM) for LPS binding*

| Compound | E. coli 055:B5 | E. coli 0111:B4 | P.a. | Klebsiella | Salmonella | Serratia |
|---|---|---|---|---|---|---|
| Tertiary Amine Derivatives | | | | | | |
| 40 | 3.4 | >5 | ND | 1.5 | ND | >5 |
| 3 | ND | ND | ND | ND | ND | ND |
| 11a | 4.4 | >5 | ND | 0.08 | 4.1 | ND |
| 11b | 0.05 | 2.7 | ND | 0.4 | 0.8 | ND |
| 12 | 0.006 | 3.1 | 4.2 | 1 | 0.4 | ND |
| 41 | 3.6 | 4.7 | >5 | ND | >5 | ND |
| 17 | 3.8 | 3.7 | >5 | 2.1 | 3.1 | ND |
| 21 | >5 | >5 | ND | 2.4 | 3.2 | ND |
| 38 | >5 | >5 | ND | ND | >5 | ND |
| Guanidine Derivatives | | | | | | |
| 27 | >5 | ND | ND | ND | 4.4 | ND |
| 36 | 4.1 | 3.9 | ND | ND | >5 | ND |
| 28 | 4.1 | >5 | ND | ND | 2.6 | ND |
| 42 | 0.04 | 0.7 | 1.5 | 1 | 0.6 | ND |
| 43 | 0.1 | 0.4 | 0.8 | 0.5 | 0.6 | 3.2 |
| Triazole Derivative | | | | | | |
| 45 | ND | ND | ND | ND | ND | ND |
| Primary Amine Derivatives | | | | | | |
| 23 | 1.3 | 0.1 | 0.5 | 0.5 | 0.2 | 4.5 |
| 46a | 0.05 | 2.2 | 2.6 | 1 | 1.1 | >5 |
| 46b | 0.6 | 1.5 | 1 | 0.9 | ND | ND |
| 4 | 0.9 | 1.6 | 0.8 | 0.3 | 0.6 | 1.5 |
| 39 | >5 | ND | ND | ND | >5 | ND |
| Negatively Charged Derivatives | | | | | | |
| 47 | >5 | >5 | ND | ND | ND | ND |
| 48 | >5 | ND | ND | ND | ND | ND |
| 49 | 5 | 5 | ND | 2.1 | ND | 4.2 |
| Peptides | | | | | | |
| SC4 | 4.2 | >5 | 4 | ND | 4 | >5 |
| βpep-25 | 2.5 | 2 | 1.2 | 2 | 2.5 | 4.1 |
| PmxB | 0.03 | 0.03 | 0.003 | 0.01 | 0.3 | ND |

ND = no detectable activity at $5 \times 10^{-6}$ M
>5 = minimal activity at $5 \times 10^{-6}$ M; no $IC_{50}$ determined.
*errors are estimated to be ±30% of the value indicated in the table.
Values in sub-micro molar range are shown in bold.

Helix/Sheet Topomimetics Protect Mice from LPS Endotoxin.

Figure 5A:
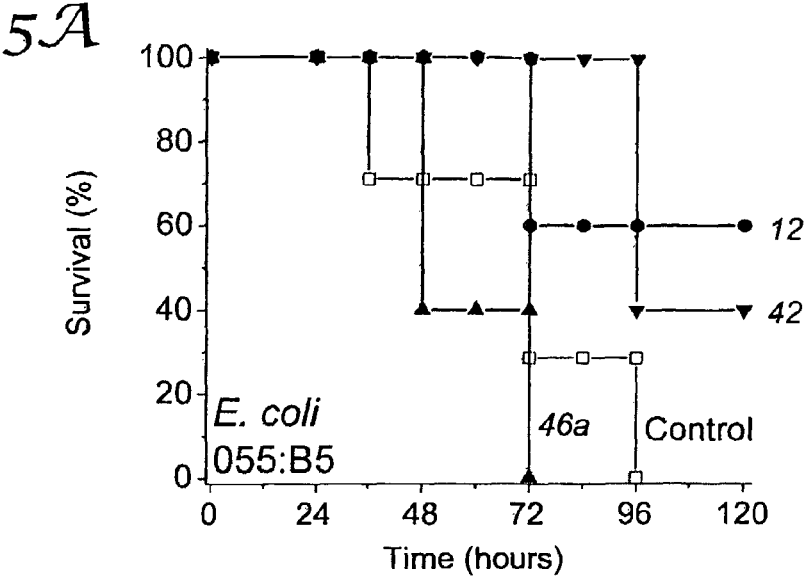
FIG. 5 provides graphs showing that helix/sheet topomimetics protect mice from LPS. Three helix/sheet topomimetics (12, 42 and 46a) were used in mouse endotoxemia models to assess in vivo efficacy. (A) Survival of mice after being challenged with 600 μl LPS form E. coli serotype 055:B5 with or without one of the compounds. The survival percentage of treatment with compound 12 and 42 are significantly improved (p=0.03 and 0.006 respectively). (B) Survival of mice after being challenged with 500 μl LPS form E. coli serotype 0111:B4 with or without one of the compounds. The survival percentage of treatment with compound 42 is significantly increased (p=1.3 $10^{-5}$). (C) Survival of mice after being challenged with 600 μl LPS form Salmonella with or without one of the compounds. The survival percentage of treatment with compound 46a, 12 and 42 are significantly increased (p=9×$10^{-8}$, 0.008 and 0.002 respectively). In all panels, symbols are defined as: control (□), 12 (●), 46a (▲), 42 (▼).
Figure 5B:
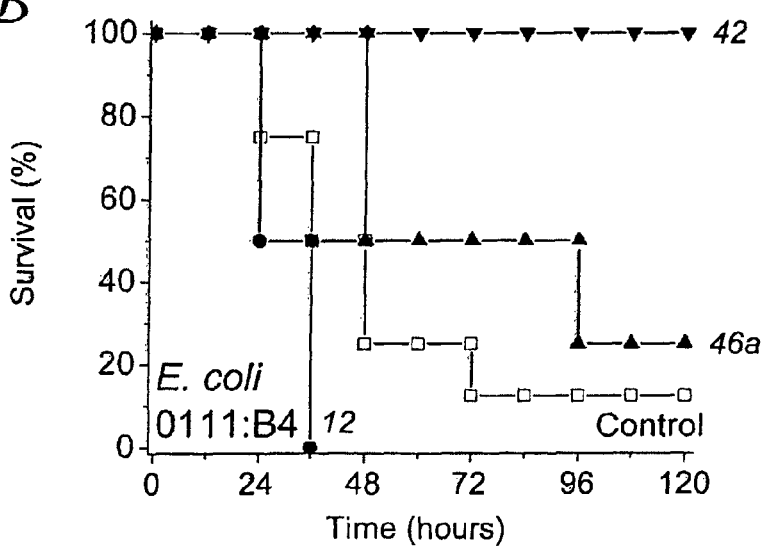
Figure 5C:
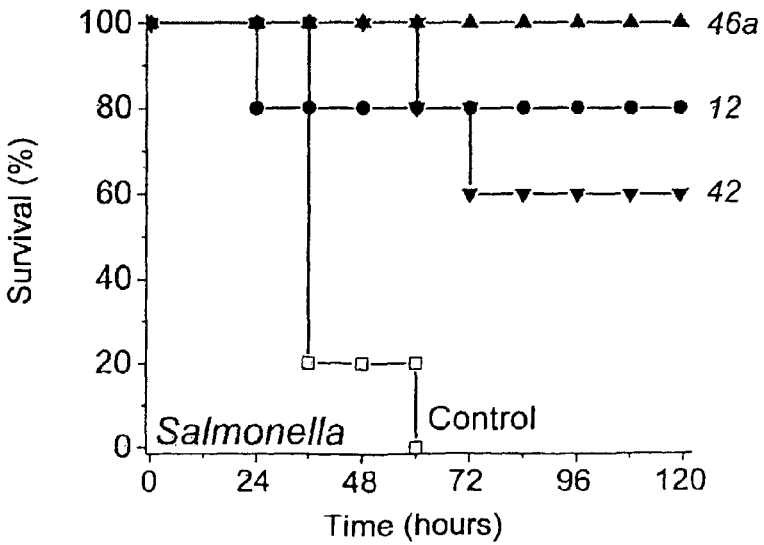

To demonstrate in vivo efficacy, one compound from each derivative subset (primary amine, tertiary amine, and guanidinium group, see Table 3 and FIG. 2) was selected to treat LPS-challenged mice. Selection was based on which compounds were most active in vitro against LPS from *E. coli* serotype 055:B5, namely 12, 42, and 46a. For this in vivo study, mice were administered a lethal dose of *E. coli* 055:B5 LPS (600 µg) and treated with each compound at doses of 5 mg/kg and 50 mg/kg. Although the 5 mg/kg dose was ineffective, the 50 mg/kg dose of 12 and 42 demonstrated protection from LPS challenge, with 60% and 40% survival, respectively, compared to 0% for controls (FIG. 5A). This encouraging result prompted testing of these compounds against LPS from the other *E. coli* strain 0111:B4, where in vitro activities were significantly less (see Table 3). Once again, mice were administered a lethal dose of *E. coli* 0111:B4 LPS (500 µg), and treated (50 mg/kg) with each of these three compounds. In this study mice treated with 42 and 46a had a 100% and 25% survival, respectively, compared to 0% for controls (FIG. 5B). Lastly, these compounds were tested in mice challenged with a lethal dose of *Salmonella* LPS (600 µg). In this case, all three compounds were effective, with 46a showing 100% survival, and 5 and 42 showing 80% and 60% survival, respectively, compared to 0% for controls (FIG. 5C). Compound 42 was the best overall.

Helix/Sheet Topomimetics Retain Anti-Angiogenic Activity.

The $^3$H-thymidine endothelial cell (EC) proliferation assay is generally used to assess angiogenic potential (Griffioen et al., Pharmacol Rev 52, 237-68 (2000)). Using this assay, it was demonstrated that two members from the 23 compound library (40 and 27) were effective at inhibiting EC growth. The dose response curves for these two compounds are shown in FIG. 6A, along with those for βpep-25 as a positive control and 11a as a negative control. Although compound 11a is inactive in this in vitro assay, at least up to the highest dose tested (25 µM), some of the other compounds do show minimal activity at the 25 µM dose. Concerning the two most active compounds, 40 ($IC_52$ µM) is slightly more active than βpep-25 ($IC_{50}$ 4 µM), and considerably more active than 27 ($IC_{50}$ 8 µM). As an initial check of general cell toxicity, similar proliferation experiments were performed using fibroblasts, MA148 human ovarian carcinoma, and murine B16 melanoma tumor cell lines. Against fibroblasts, 40 and βpep-25 showed no detectable effects, whereas 11a and 27 showed 50% growth inhibition at about 20 µM. βpep-25 and 40 were also both effective against MA148 tumor cells ($IC_{50}$ of 10 µM and 1 µM, respectively), whereas neither demonstrated activity against B16F10 tumor cells. On the other hand, 11a and 27 were effective against both MA148 ($IC_{50}$ of 8 µM and 3 µM, respectively), and B16F10 ($IC_{50}$ of 15 µM and 10 µM, respectively) tumor cell lines.

FIG. 6B shows the results of these compounds in the wound assay, where the effect on EC migration, another prognosticator of angiogenesis, is assessed. In this assay compound 27 is as effective as βpep-25 and more effective than 40, while 11a and the other calixarene analogs were ineffective.

Because either of these in vitro assays provides only limited information in terms of angiogenic potential, these compounds were also tested in the chorioallantoic membrane (CAM) assay in fertilized chicken eggs. In FIG. 6C it is apparent that angiogenesis is inhibited in embryos treated with 40 and 27, but not with 11a, compared to that in untreated, control embryos. Note that while some vessels are still apparent in these treated groups, vessel architecture is clearly affected as seen by the appearance of shorter and finer vessels. Similar angiostatic effects in the CAM assay were observed with βpep-25.

Compounds 40 and 27 Inhibit Tumor Angiogenesis and Tumor Growth in Mice.

Because 40 and 27 are effective anti-angiogenic compounds in vitro, their ill vivo efficacy was assessed using two tumor growth models in mice. In the MA148 human ovarian carcinoma tumor model in athymic mice (FIGS. 5A and 5B), therapy was initiated when tumors were approximately 70 mm$^3$ in size. Treatment with 40, 27, and βpep-25 was administered subcutaneously (s.c.) for 28 days via implanted osmotic mini-pumps. βpep-25 was given at 10 mg/kg/day, a dose shown previously in this mouse model to inhibit MA148 tumor by about 60 to 70% (Dings et al., Cancer Lett 194, 55-66 (2003)). Agents 40 and 27 were administered at two doses: the pharmacologically equivalent dose (10 mg/kg/day) and the molar equivalent dose (2.4 mg/kg/day for 40 and 2.7 mg/kg/day for 27). At the end of 28 days of treatment, 40 at 10 mg/kg and 2.4 mg/kg inhibited tumor growth on average by 81% and about 65%, respectively. The levels of growth inhibition for 40 and βpep-25 on a molar equivalent basis are very similar (FIG. 7A). After 28 days of treatment, the rate of tumor growth began to increase, but even two weeks post-treatment, tumor growth inhibition remained at similar levels to that observed at the end of treatment. In the same MA148 model, 27 inhibited tumor growth by about 65% at either dose tested (FIG. 7B). This level of inhibition was also the same as that for βpep-25 at 10 mg/kg.

To assess efficacy in another tumor model, 40 and 17 were tested against the more aggressive B16 melanoma, a syngeneic model in immunocompetent mice. Tumors were allowed to grow to approximately 80 mm$^3$, and treatment with 40, 27, and βpep-25 was initiated by s.c. administration via implanted osmotic mini-pumps (FIG. 7C), and, in another study, by interperitoneal (i.p.) injection twice daily for 7 days (FIG. 7D). All three compounds (βpep-25, 40, and 27) were given at a close of 10 mg/kg/day. In this tumor model 40 inhibited tumor growth on average by 80% when administered s.c. and 75% when administered i.p., whereas 27 inhibited tumor growth by 55% and 75%, respectively. βpep-25 was comparably effective at 45% and 60% when administered s.c. and i.p., respectively.

Figure 8:
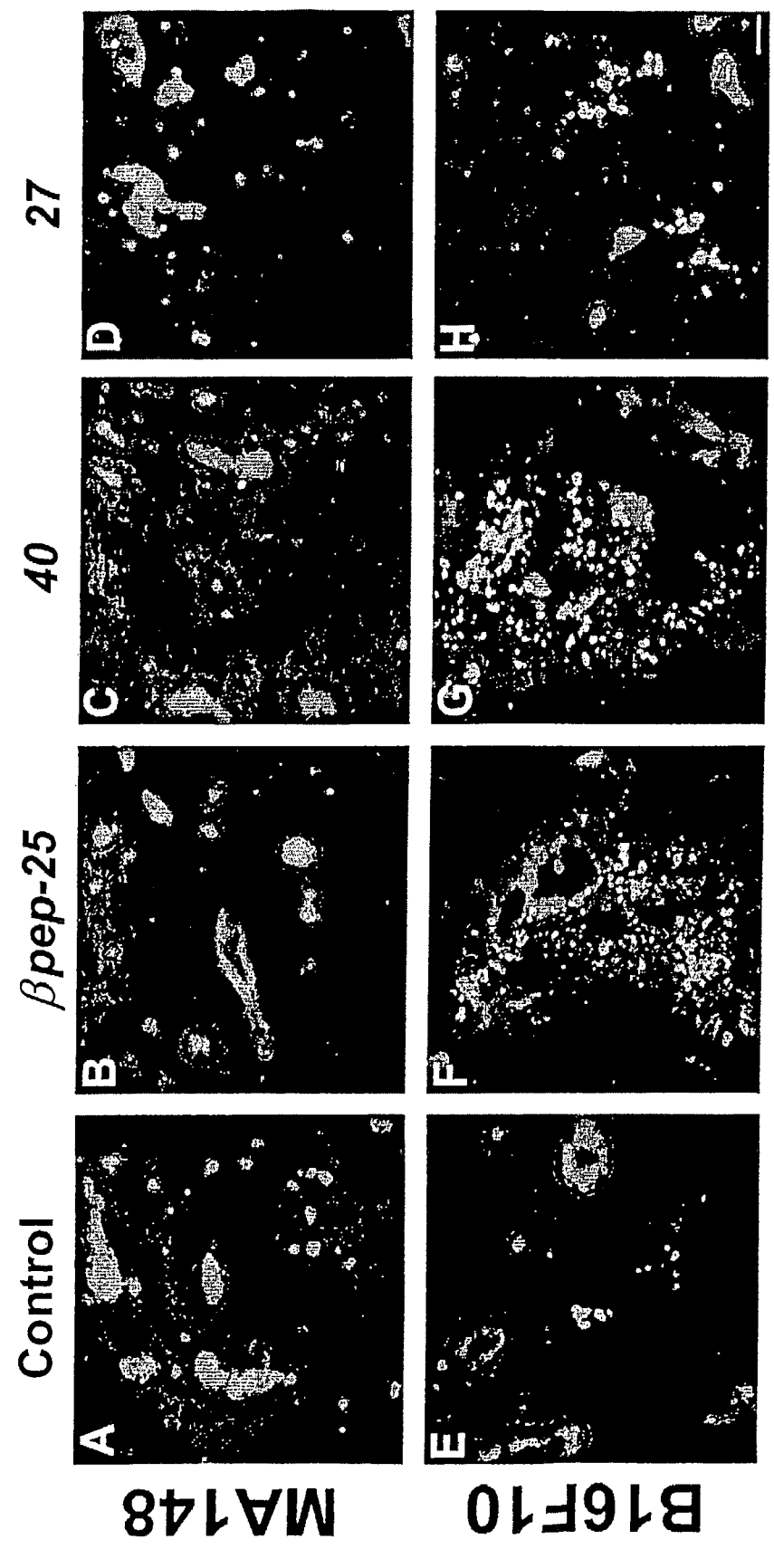
FIG. 8 provides pictures showing that topomimetics inhibit tumor angiogenesis. For histochemical analysis, tumor cross-sections were stained for microvessel density (MVD) using PE-labeled anti-CD31 antibody staining and for total cell apoptosis using TUNEL (FITC labeled) analysis. MA148 tumor section staining (A-D), and B16F10 tumor section staining (E-H) are shown for vehicle treated (A and E), βpep-25 treated (B and F), 40 treated (C and G), and 27 treated (D and H). Images are representatives of the means for the 10 mg/kg dose. Original magnification X200; scale bar=50 μm. Quantification of microvessel density and apoptosis are provided in Table 3.

Anti-angiogenic potential in vivo was demonstrated immunohistochemically by staining MA148 and B16F10 tumor cross-sections from animals treated with 40 and 27 with fluorescently-labeled anti-CD31 antibody to identify blood vessels. As shown and quantified in FIG. 2 and Table 3, respectively, vessel density in treated tumors relative to that in control tumors (FIGS. 8A and 8E) was significantly decreased by treatment with βpep-25 (FIGS. 8B and 8F), 40 (FIGS. 8C and 8G), and 27 (FIGS. 8D and 8H). These compounds had a significant effect as well on vessel architecture, demonstrating a drop in the number of end points, branch points, and vessel length (Table 3). In addition, anti-angiogenic treatment also increased the rate of apoptosis of tumor cells, as determined using immunohistochemical staining by TUNEL in cryosections of tumors (Table 3).

TABLE 3

Histological analysis of microvessel density[a]

| MA148 | Vessel Density[b] | End Points[c] | Branch Points[d] | Vessel Length[e] | Apoptosis[f] |
| --- | --- | --- | --- | --- | --- |
| Control | 9157 ± 787 | 48.3 ± 7.4 | 3.6 ± 0.7 | 7.5 ± 0.6 | 1604 ± 258 |
| βpep-25 (10 mg/kg) | 7415 ± 686* | 16.6 ± 1.8* | 2.0 ± 0.5* | 4.9 ± 0.6* | 2418 ± 77* |

TABLE 3-continued

Histological analysis of microvessel density[a]

| | | | | | |
|---|---|---|---|---|---|
| 40 (2.4 mg/kg) | 7148 ± 844* | 15.7 ± 2.1* | 1.6 ± 0.3* | 5.3 ± 0.7* | 2919 ± 144* |
| 40 (10 mg/kg) | 5112 ± 439* | 23.0 ± 2.9* | 1.0 ± 0.2* | 3.3 ± 0.5* | 2323 ± 171* |
| 27 (2.7 mg/kg) | 6046 ± 533* | 32.7 ± 6.0* | 1.1 ± 0.3* | 4.2 ± 0.6* | 2418 ± 72* |
| 27 (10 mg/kg) | 7402 ± 763 | 14.7 ± 2.2* | 2.3 ± 0.6 | 5.0 ± 0.7* | 2333 ± 173* |

| B16F10 | Vessel Density | End Points | Branch Points | Vessel Length | Apoptosis |
|---|---|---|---|---|---|
| Control | 18193 ± 1683 | 34.4 ± 6.0 | 6.6 ± 1.0 | 13.4 ± 1.2 | 2216 ± 133 |
| βpep-25 (10 mg/kg) | 14050 ± 1826* | 31.9 ± 3.8 | 4.5 ± 0.6* | 10.2 ± 1.2* | 3303 ± 606* |
| 40 (10 mg/kg) | 10231 ± 1330* | 21.9 ± 2.6* | 5.2 ± 0.7* | 8.6 ± 1.2* | 2807 ± 140* |
| 27 (10 mg/kg) | 10743 ± 764* | 35.2 ± 4.0 | 3.5 ± 0.5* | 75 ± 0.6* | 2357 ± 103 |

[a]On the last day of treatment, tumors were excised. Similar size tumors without apparent widespread necrosis were embedded in tissue freezing medium (Miles Inc.; Elkart, IN) and snap frozen in liquid nitrogen. Preparation and procedures are as described in the Methods section.
[b]After binarization of the images from CD31-staining, microvessel density was estimated by scoring the total number of white pixels per field.
[c]Mean number of vessel end points as determined after skeletonization of the images.
[d]Mean number of vessel branch points/nodes per image.
[e]Mean total vessel length per image.
[f]After binarization of the images from TUNEL-staining, apoptosis was estimated by scoring the total number of white pixels per field.
All results are expressed as mean pixel counts per image standard error from 20 images.
*p ≤ 0.05; Student's t-test.

Absence of Toxicity from Topomimetic Compounds.

In all in vivo experiments treatment with 40, 27, and βpep-25, did not generally show signs of toxicity, as assessed by unaltered behavior, normal weight gain during experiments, and hematocrit levels in the blood. Percent changes in body weights are given as inserts in FIG. 7. In general body weights increased for animals in all groups, with one exception. In the B16 model i.p. administration of 27 caused weights to drop by about 5% on average during the course of treatment (insert to FIG. 7D). On the last day of treatment with either model, blood was drawn and hematocrit levels were determined as a measure of bone marrow toxicity. Hematocrit levels, reported as a percentage of red blood cells ±SD, were: vehicle 47±5.7, βpep-25 47±2.8, 40 (2.4 mg/kg) 50±1.4, 40 (10 mg/kg) 49.5±2.1, 27 (2.7 mg/kg) 46.5±0.7, and 27 (10 mg/kg) 47±4.2). The study with B16 tumors in immune competent mice showed similar hematocrit levels (vehicle 51±1.4, βpep-25 52.5±3.5, 40 53±0, and 27 49±1.4 in percentage red blood cells ±SD). Upon autopsy, macro- and microscopic morphology of internal organs were also observed to be normal within all experimental groups of animals.

In the endotoxemia model experiments mice did not demonstrate any sign of acute toxicity upon i.p. administration of compounds 12, 42, or 46a at a single dose of 50 ng/kg. Although these mice were treated simultaneously with LPS, which by itself induced a lethargic effect, more mice generally survived when treated with the topomimetic compounds. Moreover, 12, 42, and 46a belong to the same class of calixarene-based compounds, making them likely to be as nontoxic as 40 and 27.

Discussion

Although all of the calixarene-based peptide mimetics prepared are both amphipathic and have similar overall molecular dimensions as a segment of β-sheet-folded βpep-25 or helix-forming SC4, none exactly matches the surface topology of either peptide. For example, the key side chains in βpep-25 (valine, leucine and isoleucine on the hydrophobic surface and lysine (mostly) and arginine on the hydrophilic side) are mixed and heterogeneous within the context of the amphipathic surface. The calixarene-based peptide mimetics, on the other hand, mostly display the same chemical groups on each respective surface of the calixarene scaffold. Moreover, because calixarene-based compounds are not as internally flexible as peptides, the smaller negative conformational entropy change that occurs upon binding their target, may in fact contribute to their biological activity.

Topomimetics 40 and 27 are highly effective antiangiogenic agents and are capable of inhibiting tumor growth in vivo. Even though these two compounds share a net positive charge and amphipathic character, they have obvious structural and functional differences. Based on similar responses of cells in culture, it appears that compound 40 targets the same receptor as βpep-25, whereas 27 does not.

Other of the topomimetic compounds prepared clearly target LPS. These calixarene-based compounds present hydrophobic and positively charged groups in a manner that allows them to effectively bind to and to neutralize the bacterial endotoxin better than parent peptides SC4 and βpep-25. Although the LPS binding activity of a given topomimetic depends on the bacterial source of LPS, the presence of alkyl chains on the hydrophobic face of the calix[4]arene scaffold is important. Overall, the best LPS binding topomimetics have tert-butyl groups on the hydrophobic face of the calixarene scaffold and primary amines or guanidinium groups on the hydrophilic face.

At least when comparing these compounds with their limited variability of aliphatic groups, LPS binding activity differences are generally minimal and appear to depend more on which positively charged groups are on the hydrophilic face. In fact, selection of positively charged groups appears to be much more important for LPS binding than does the choice of which short chain alkyl groups are on the hydrophobic face. This may imply that the topomimetics interact with the phosphate groups on lipid A, which would be consistent with structural studies of peptides that complex with LPS from *E. coli*. Japelj et al (2005) reported that two of the arginine guanidino groups in peptide LF11 are positioned close to the two phosphate groups of the lipid A moiety (Japelj et al., J Biol Chem 280, 16955-61 (2005)). The distance of about 13 Å separating the two phosphate groups on LPS matches that between these two guanidinium groups in the LF11, as well as between guanidinium groups in topomimetic 42. On the other hand although charge separations are similar, primary amines from lysine residues of peptide FhuA dominate the interaction with the lipid A moiety of LPS from *E. coli* serotype K-12 (Ferguson et al., Science 282, 2215-20 (1998)). A similar statement can be made for PmxB in complex with LPS from *E. coli* serotype O55:B5, where four α,γ-diaminobutyric acid groups correspond to the arginine and lysines cationic groups in LF11 and in FhuA.

Unfortunately, all complexes of peptides and LPS done to date have only used LPS from *E. coli* serotypes (O55:B5 or K-12). Most of the topomimetic compounds prepared demonstrate their best activities against LPS from the two strains of *E. coli* that were tested. For LPS derived from other Gram negative bacteria, binding of the compounds to LPS is generally decreased and perhaps is more selective, possibly because the complexity of their LPS is greater than that found in *E. coli* (Rietschel et al., Curr Top Microbiol Immunol 216, 39-81 (1996)). On the other hand, the three compounds (12, 42, 46a) tested in the endotoxemia model in mice did demonstrate overall better activity against *Salmonella* LPS than against either *E. coli* LPS.

The example demonstrates that a simple non-peptidic compound can be designed to mimic the molecular dimensions and amphipathic surface topology of helix and β-sheet peptides that bind LPS and inhibit angiogenesis and tumor growth. These agents may be clinically useful by providing a means to prevent septic shock upon bacterial infection and/or to stem cancerous growth. As antiangiogenic agents, these topomimetics may also have utility against other pathological disorders that involve angiogenesis, namely arthritis, restenosis, atherosclerosis, endometriosis and diabetic retinopathy. Furthermore, because helix and β-sheet structural motifs are common to many other peptides (Laskowski et al., Nucleic Acids Research 33, D266-268 (2005)), the topomimetic compounds could be viewed as comprising a generic library of protein surface topomimetics and may prove useful in the study of additional biological effects beyond those exhibited by LPS neutralizing and antiangiogenic proteins.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A method for inhibiting endothelial cell proliferation, the method comprising contacting cells with an amount of a composition effective to inhibit endothelial cell proliferation, wherein the composition comprises a calixarene-based peptide mimetic selected from the group consisting of

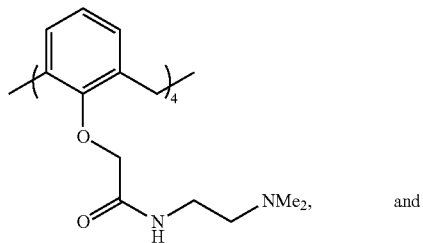
(compound 40)

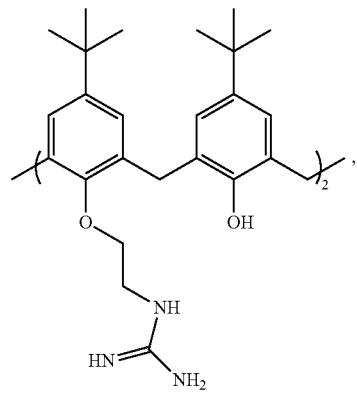
(compound 27)

and isomers, tautomers, and salts thereof,
wherein the calixarene-based peptide mimetic demonstrates inhibition in an in vitro endothelial cell proliferation assay monitoring uptake of tritiated thymidine at an IC50 value of less than 25 μM.

2. A method for inhibiting angiogenesis, the method comprising contacting cells with an amount of a composition effective to inhibit angiogenesis, the composition comprising a calixarene-based peptide mimetic selected from the group consisting of

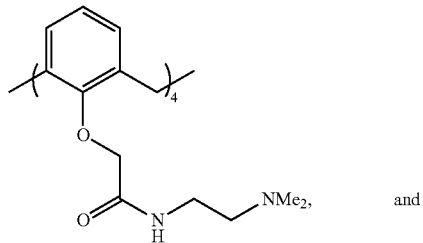
(compound 40)

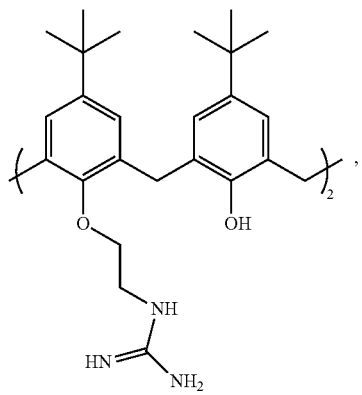
(compound 27)

and isomers, tautomers, and salts thereof, wherein the calixarene-based peptide mimetic demonstrates inhibition in an in vitro endothelial cell proliferation assay monitoring uptake of tritiated thymidine at an IC50 value of less than 25 µM.

3. The method of claim 1, wherein the calixarene-based peptide mimetic is provided as a pharmaceutically acceptable salt.

4. The method of claim 1, wherein the calixarene-based peptide mimetic comprises an ionic form that is positively charged.

5. The method of claim 1, wherein the contacting step occurs in vitro.

6. The method of claim 1, wherein the contacting step occurs in vivo.

7. The method of claim 1, wherein the cells are present in a cell culture, a tissue, an organ, or an organism.

8. The method of claim 1, wherein the cells are mammalian cells.

9. The method of claim 8 wherein the cells are human cells.

10. A method for inhibiting tumorigenesis in a patient, the method comprising administering to the patient a therapeutically effective amount of a composition comprising a calixarene-based peptide mimetic selected from the group consisting of

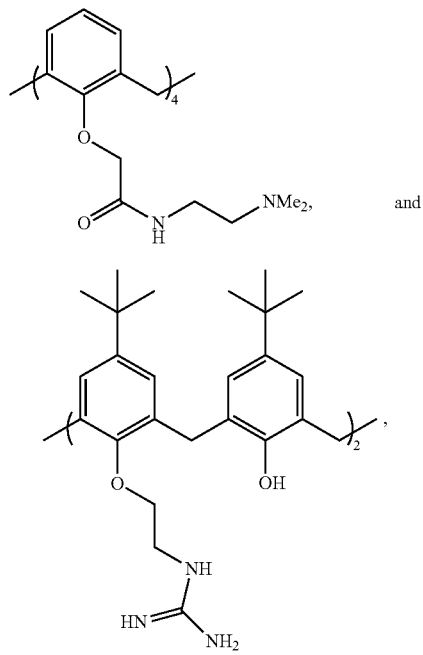

and isomers, tautomers, and salts thereof,
wherein the calixarene-based peptide mimetic demonstrates inhibition in an in vitro endothelial cell proliferation assay monitoring uptake of tritiated thymidine at an IC50 value of less than 25 µM.

11. A method for increasing the infiltration of leukocytes into tumor tissue in a patient, the method comprising administering to the patient a therapeutically effective amount of a composition comprising a calixarene-based peptide mimetic selected from the group consisting of

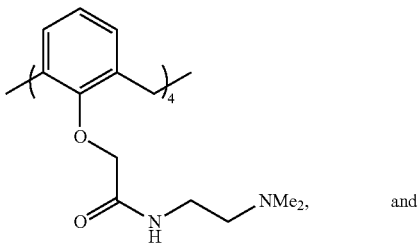

and isomers, tautomers, and salts thereof,
wherein the calixarene-based peptide mimetic demonstrates inhibition in an in vitro endothelial cell proliferation assay monitoring uptake of tritiated thymidine at an IC50 value of less than 25 µM.

12. The method of claim 10, wherein the calixarene-based peptide mimetic is provided as a pharmaceutically acceptable salt.

13. The method of claim 2, wherein the calixarene-based peptide mimetic is provided as a pharmaceutically acceptable salt.

14. The method of claim 2, wherein the calixarene-based peptide mimetic comprises an ionic form that is positively charged.

15. The method of claim 10, wherein the calixarene-based peptide mimetic comprises an ionic form that is positively charged.

16. The method of claim 1, wherein the isomer is a diastereomer or enantiomer.

17. The method of claim 2, wherein the isomer is a diastereomer or enantiomer.

18. The method of claim 10, wherein the isomer is a diastereomer or enantiomer.

19. The method of claim 2, wherein the contacting step occurs in vitro.

20. The method of claim 2, wherein the contacting step occurs in vivo.

21. The method of claim 2, wherein the cells are present in a cell culture, a tissue, an organ, or an organism.

22. The method of claim 2, wherein the cells are mammalian cells.

23. The method of claim 22 wherein the cells are human cells.

24. The method of claim 11, wherein the calixarene-based peptide mimetic is provided as a pharmaceutically acceptable salt.

25. The method of claim 11, wherein the calixarene-based peptide mimetic comprises an ionic form that is positively charged.

26. The method of claim 11, wherein the isomer is a diastereomer or enantiomer.

27. A method of treating ovarian cancer in a patient in need thereof, the method comprising contacting ovarian cancer cells in the patient with a therapeutically effective amount of a composition to treat ovarian cancer, wherein the composition comprises a calixarene-based peptide mimetic selected from the group consisting of

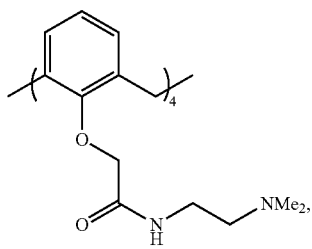
(compound 40)

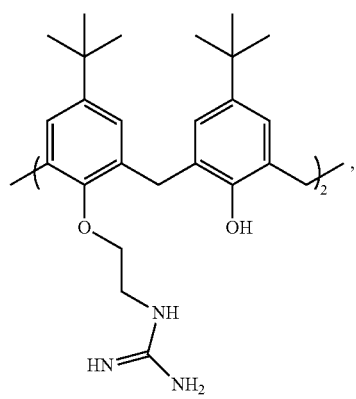
(compound 27)

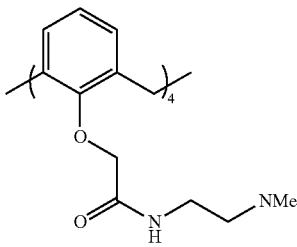
(compound 40)

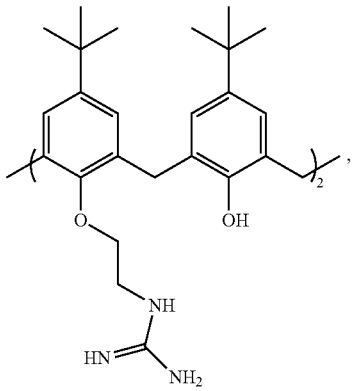
(compound 27)

and isomers, tautomers, and salts thereof,
wherein the calixarene-based peptide mimetic demonstrates inhibition in an in vitro endothelial cell proliferation assay monitoring uptake of tritiated thymidine at an IC50 value of less than 25 μM.

28. A method of treating melanoma in a patient in need thereof, the method comprising contacting melanoma cells in the patient with a therapeutically effective amount of a composition to treat melanoma, wherein the composition comprises a calixarene-based peptide mimetic selected from the group consisting of and isomers, tautomers, and salts thereof,
wherein the calixarene-based peptide mimetic demonstrates inhibition in an in vitro endothelial cell proliferation assay monitoring uptake of tritiated thymidine at an IC50 value of less than 25 μM.

29. The method of claim 27, wherein the calixarene-based peptide mimetic is provided as a pharmaceutically acceptable salt.

30. The method of claim 27, wherein the calixarene-based peptide mimetic comprises an ionic form that is positively charged.

31. The method of claim 27, wherein the isomer is a diastereomer or enantiomer.

32. The method of claim 28, wherein the calixarene-based peptide mimetic is provided as a pharmaceutically acceptable salt.

33. The method of claim 28, wherein the calixarene-based peptide mimetic comprises an ionic form that is positively charged.

34. The method of claim 28, wherein the isomer is a diastereomer or enantiomer.

* * * * *

UNITED STATES PATENT AND TRADEMARK OFFICE
CERTIFICATE OF CORRECTION

PATENT NO. : 8,207,228 B2  
APPLICATION NO. : 11/664641  
DATED : June 26, 2012  
INVENTOR(S) : Mayo et al.

Page 1 of 1

It is certified that error appears in the above-identified patent and that said Letters Patent is hereby corrected as shown below:

Cover page, item (75) Inventors
Delete "Xuemei Cheri" and insert --Xuemei Chen--

Column 1, Line 15
delete "The present invention was made with government support under Grant No. R0 01 CA-96090, awarded by the National Cancer Institute, and Grant No. U54 AI-57153, awarded by the National Institute of Allergy and Infectious Diseases. The Government may have certain rights in this invention."

and insert

--This invention was made with government support under CA096090 and AI057153 awarded by the National Institutes of Health and DAMD17-99-1-9564 awarded by the Army. The government has certain rights in this invention.--

Signed and Sealed this
Twenty-eighth Day of August, 2012

David J. Kappos
*Director of the United States Patent and Trademark Office*